(12) United States Patent
Hutchinson et al.

(10) Patent No.: US 9,714,240 B2
(45) Date of Patent: Jul. 25, 2017

(54) VINYL AUTOTAXIN INHIBITOR COMPOUNDS

(71) Applicant: PharmAkea, Inc., San Diego, CA (US)

(72) Inventors: John Howard Hutchinson, San Diego, CA (US); Timothy Andrew Parr, Menifee, CA (US); David Lonergan, San Marcos, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

(21) Appl. No.: 15/022,167

(22) PCT Filed: Sep. 16, 2014

(86) PCT No.: PCT/US2014/055901
§ 371 (c)(1),
(2) Date: Mar. 15, 2016

(87) PCT Pub. No.: WO2015/042053
PCT Pub. Date: Mar. 26, 2015

(65) Prior Publication Data
US 2016/0222000 A1 Aug. 4, 2016

Related U.S. Application Data

(60) Provisional application No. 61/878,922, filed on Sep. 17, 2013.

(51) Int. Cl.

| | |
|---|---|
| C07D 209/18 | (2006.01) |
| C07D 401/06 | (2006.01) |
| C07D 403/04 | (2006.01) |
| C07D 413/06 | (2006.01) |
| A61K 31/4245 | (2006.01) |
| A61K 31/427 | (2006.01) |
| A61K 31/4439 | (2006.01) |
| C07D 417/06 | (2006.01) |
| C07D 403/06 | (2006.01) |
| A61K 45/06 | (2006.01) |
| A61K 9/00 | (2006.01) |
| A61K 47/10 | (2017.01) |
| A61K 47/14 | (2017.01) |
| A61K 9/06 | (2006.01) |
| A61K 47/38 | (2006.01) |
| A61K 9/20 | (2006.01) |
| A61K 9/48 | (2006.01) |
| A61K 31/404 | (2006.01) |
| A61K 31/4155 | (2006.01) |
| C07D 209/24 | (2006.01) |

(52) U.S. Cl.
CPC .......... *C07D 417/06* (2013.01); *A61K 9/0014* (2013.01); *A61K 9/0019* (2013.01); *A61K 9/0095* (2013.01); *A61K 9/06* (2013.01); *A61K 9/2054* (2013.01); *A61K 9/2095* (2013.01); *A61K 9/4866* (2013.01); *A61K 31/404* (2013.01); *A61K 31/4155* (2013.01); *A61K 31/427* (2013.01); *A61K 31/4245* (2013.01); *A61K 31/4439* (2013.01); *A61K 45/06* (2013.01); *A61K 47/10* (2013.01); *A61K 47/14* (2013.01); *A61K 47/38* (2013.01); *C07D 209/18* (2013.01); *C07D 209/24* (2013.01); *C07D 401/06* (2013.01); *C07D 403/04* (2013.01); *C07D 403/06* (2013.01); *C07D 413/06* (2013.01)

(58) Field of Classification Search
None
See application file for complete search history.

(56) References Cited

U.S. PATENT DOCUMENTS

| | | | |
|---|---|---|---|
| 4,271,263 | A | 6/1981 | Goettert |
| 7,060,697 | B2 | 6/2006 | Marsilje et al. |
| 8,022,239 | B2 | 9/2011 | Parrill-Baker et al. |
| 8,268,891 | B1 | 9/2012 | Parrill-Baker et al. |
| 8,329,907 | B2 | 12/2012 | Schultz et al. |
| 8,343,934 | B2 | 1/2013 | Parrill-Baker et al. |
| 8,378,100 | B2 | 2/2013 | Lynch et al. |
| 8,497,371 | B2 | 7/2013 | Parrill-Baker et al. |
| 8,673,882 | B2 | 3/2014 | Gupte et al. |
| 9,000,025 | B2 | 4/2015 | Roppe et al. |
| 9,051,320 | B1 | 6/2015 | Evans |
| 2006/0270634 | A1 | 11/2006 | Miller et al. |
| 2009/0118503 | A1 | 5/2009 | Sprott et al. |
| 2010/0016258 | A1 | 1/2010 | Lynch et al. |
| 2010/0069360 | A1 | 3/2010 | Revesz et al. |

(Continued)

FOREIGN PATENT DOCUMENTS

| | | |
|---|---|---|
| JP | 2000336075 A | 12/2000 |
| WO | WO-0130343 A1 | 5/2001 |

(Continued)

OTHER PUBLICATIONS

Hörig et al., J. Translational Med. 2:44 (2004).*

(Continued)

*Primary Examiner* — Michael Barker
(74) *Attorney, Agent, or Firm* — Wilson Sonsini Goodrich & Rosati

(57) ABSTRACT

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

22 Claims, No Drawings

(56) References Cited

U.S. PATENT DOCUMENTS

| | | |
|---|---|---|
| 2010/0136650 A1 | 6/2010 | Parrill-Baker et al. |
| 2010/0197708 A1 | 8/2010 | Talley et al. |
| 2010/0222341 A1 | 9/2010 | Schiemann et al. |
| 2011/0065703 A1 | 3/2011 | Wu |
| 2011/0110886 A1 | 5/2011 | Braddock |
| 2011/0160148 A1 | 6/2011 | Parrill-Baker et al. |
| 2011/0230471 A1 | 9/2011 | Staehle et al. |
| 2011/0237583 A1 | 9/2011 | Schiemann et al. |
| 2012/0015959 A1 | 1/2012 | Staehle et al. |
| 2012/0015976 A1 | 1/2012 | Schultz et al. |
| 2012/0059016 A1 | 3/2012 | Schiemann et al. |
| 2012/0100592 A1 | 4/2012 | Parrill-Baker et al. |
| 2012/0115852 A1 | 5/2012 | Schultz et al. |
| 2012/0190650 A1 | 7/2012 | Gupte et al. |
| 2012/0202827 A1 | 8/2012 | Schiemann et al. |
| 2012/0270863 A1 | 10/2012 | Williams et al. |
| 2012/0316162 A1 | 12/2012 | Schiemann et al. |
| 2013/0012505 A1 | 1/2013 | Staehle et al. |
| 2013/0023556 A1 | 1/2013 | Schultz et al. |
| 2013/0029948 A1 | 1/2013 | Roppe et al. |
| 2013/0150326 A1 | 6/2013 | Roppe et al. |
| 2014/0171403 A1 | 6/2014 | Legrand et al. |
| 2014/0171404 A1 | 6/2014 | Furminger et al. |
| 2016/0046614 A1 | 2/2016 | Hutchinson et al. |
| 2016/0229809 A1 | 8/2016 | Hutchinson et al. |

FOREIGN PATENT DOCUMENTS

| | | |
|---|---|---|
| WO | WO-02083126 A1 | 10/2002 |
| WO | WO-03029212 A1 | 4/2003 |
| WO | WO-03087087 A2 | 10/2003 |
| WO | WO-2004019869 A2 | 3/2004 |
| WO | WO-2004020408 A1 | 3/2004 |
| WO | WO-2004020409 A1 | 3/2004 |
| WO | WO-2005061455 A1 | 7/2005 |
| WO | WO-2006041961 A1 | 4/2006 |
| WO | WO-2006050236 A2 | 5/2006 |
| WO | WO-2006134499 A2 | 12/2006 |
| WO | WO-2007134169 A2 | 11/2007 |
| WO | WO-2008019357 A2 | 2/2008 |
| WO | WO-2008025512 A1 | 3/2008 |
| WO | WO-2008157740 A2 | 12/2008 |
| WO | WO-2009151644 A2 | 12/2009 |
| WO | WO-2010040080 A1 | 4/2010 |
| WO | WO-2010060532 A1 | 6/2010 |
| WO | WO-2010063352 A1 | 6/2010 |
| WO | WO-2010112124 A1 | 10/2010 |
| WO | WO-2010115491 A2 | 10/2010 |
| WO | WO-2010150211 A2 | 12/2010 |
| WO | WO-2011002918 A1 | 1/2011 |
| WO | WO-2011006569 A1 | 1/2011 |
| WO | WO-2011047432 A1 | 4/2011 |
| WO | WO-2011053597 A1 | 5/2011 |
| WO | WO-2011094708 A2 | 8/2011 |
| WO | WO-2012024620 A2 | 2/2012 |
| WO | WO-2012083058 A2 | 6/2012 |
| WO | WO-2012100018 A1 | 7/2012 |
| WO | WO-2012116135 A2 | 8/2012 |
| WO | WO-2012158785 A1 | 11/2012 |
| WO | WO-2012166415 A1 | 12/2012 |
| WO | WO-2013054185 A1 | 4/2013 |
| WO | WO-2014097151 A2 | 6/2014 |
| WO | WO-2015042052 A1 | 3/2015 |
| WO | WO-2015042053 A1 | 3/2015 |
| WO | WO-2015048301 A1 | 4/2015 |
| WO | WO-2015077502 A1 | 5/2015 |
| WO | WO-2015077503 A1 | 5/2015 |

OTHER PUBLICATIONS

Liu, et al., Acta Pharmaceutica Sinica, 34:908 (1999).*
Benesch, et al., The FASEB Journal, 28:2655 (2014, published online Mar. 5, 2014).*
St-Cœur, et al., Arch. Pharm. Chem. Life Sci., 346:91 (2013).*
Albers et al. Boronic acid-based inhibitor of autotaxin reveals rapid turnover of LPA in the circulation. PNAS USA 107:7257-7262 (2010).
Albers et al. Chemical evolution of autotaxin inhibitors. Chem. Rev. 112:2593-2603 (2012).
Albers et al. Discovery and optimization of boronic acid based inhibitors of autotaxin. J. Med. Chem. 53:4958-4967 (2010).
Albers et al. Structure-based design of novel boronic acid-based inhibitors of autotaxin. J. Med. Chem. 54:4619-4626 (2011).
Baker et al. Carba analogs of cyclic phosphatidic acid are selective inhibitors of autotaxin and cancer cell invasion and metastasis. J. Biol. Chem. 281:22786-22793 (2006).
Barbayianni et al. Autotaxin inhibitors: a patent review. Expert Opin Ther Pat. 23(9):1123-1132 (2013).
Chemical Structure Search Jun. 26, 2013 (258 pgs).
Cui et al. alpha- and beta-substituted phosphonate analogs of LPA as autotaxin inhibitors. Bioorg. Med. Chem. 16:2212-2225 (2008).
Cui et al. Synthesis and biological evaluation of phosphonate derivatives as autotaxin (ATX) inhibitors. Bioorg. Med. Chem. Lett. 17:1634-1640 (2007).
Durgam et al. Synthesis and pharmacological evaluation of second-generation phosphatidic acid derivatives as lysophosphatidic acid receptor ligands. Bioorg. Med. Chem. Lett. 16:633-640 (2006).
Durgam et al. Synthesis, structure-activity relationships, and biological evaluation of fatty alcohol phosphates as lysophosphatidic acid receptor ligands, activators of PPARgamma, and inhibitors of autotaxin. J. Med. Chem. 48:4919-4930 (2005).
East et al. Synthesis and structure-activity relationships of tyrosine-based inhibitors of autotaxin (ATX). Bioorg. Med. Chem. Lett. 20:7132-7136 (2010).
Federico et al. Therapeutic potential of autotaxin/lysophospholipase d inhibitors. Curr Drug Targets 9(8):698-708 (2008).
Ferry et al. S32826, A Nanomolar Inhibitor of Autotaxin: Discovery, Synthesis and Applications as a Pharmacological Tool. J. Pharmacol. Exp. Ther. 327:809-819 (2008).
Gajewak et al. Synthesis, pharmacology, and cell biology of sn-2-aminooxy analogues of lysophosphatidic acid. Org. Lett. 10:1111-1114 (2008).
Geiss et al. A high-throughput screening assay for the identification of flavivirus NS5 capping enzyme GTP-binding inhibitors: implications for antiviral drug development. J Biomol Screen 16(8):852-861 (2011).
Gendaszewska-Darmach et al. The chemical synthesis of metabolically stabilized 2-OMe-LPA analogues and preliminary studies of their inhibitory activity toward autotaxin. Bioorg. Med. Chem. Lett. 22:2698-2700 (2012).
Gierse et al. A novel autotaxin inhibitor reduces lysophosphatidic acid levels in plasma and the site of inflammation. J. Pharmacol. Exp. 334:310-317 (2010).
Gududuru et al. Identification of Darmstoff analogs as selective agonists and antagonists of lysophosphatidic acid receptors. Bioorg. Med. Chem. Lett. 16:451-456 (2006).
Gupte et al. Benzyl and naphthalene methylphosphonic acid inhibitors of autotaxin with anti-invasive and anti-metastatic activity. ChemMedChem 6:922-935 (2011).
Gupte et al. Synthesis and pharmacological evaluation of the stereoisomers of 3-carba cyclic-phosphatidic acid. Bioorg. Med. Chem. Lett. 20:7525-7528 (2010).
Higazi et al. Immunomodulatory effects of plasminogen activators on hepatic fibrogenesis. Clin Exp Immunol 152(1):163-173 (2008).
Hoeglund et al. Characterization of non-lipid autotaxin inhibitors. Bioorg. Med. Chem. 18:769-776 (2010).
Hoeglund et al. Optimization of a pipemidic acid autotaxin inhibitor. J. Med. Chem. 53:1056-1066 (2010).
Humphrey et al. Practical methodologies for the synthesis of indoles. Chem Rev. 106(7):2875-2911 (2006).
Jiang et al. Alpha-substituted phosphonate analogues of lysophosphatidic acid (LPA) selectively inhibit production and action of LPA. ChemMedChem 2:679-690 (2007).
Jiang et al. Aromatic phosphonates inhibit the lysophospholipase D activity of autotaxin. Bioorg. Med. Chem. Lett. 21:5098-5101 (2011).

(56) References Cited

OTHER PUBLICATIONS

Kano et al. LPA and its analogs-attractive tools for elucidation of LPA biology and drug development. Curr. Med. Chem. 15:2122-2131 (2008).

Kianmehr et al. Palladium-catalyzed cyanoalkenylation of indoles. Tetrahedron 69(25):5193-5196 (2013).

Lien et al. 1-Benzyl-3-(5'-hydroxymethyl-2'-furyl)indazole (YC-1) derivatives as novel inhibitors against sodium nitroprusside-induced apoptosis. J Med Chem 45(23):4947-4949 (2002).

Moulharat et al. Molecular pharmacology of adipocyte-secreted autotaxin. Chem.-Biol. Interact. 172:115-124 (2008).

North et al. Pharmacophore development and application toward the identification of novel, small-molecule autotaxin inhibitors. J. Med. Chem. 53:3095-3105 (2010).

Parrill et al. Autotaxin Inhibitors: A Perspective on Initial Medicinal Chemistry Efforts. Expert Opin Ther Pat 20(12):1619-1625 (2010).

Parrill et al. Virtual screening approaches for the identification of non-lipid autotaxin inhibitors. Bioorg. Med. Chem. 16:1784-1795 (2008).

PCT/US2014/055899 International Search Report and Written Opinion dated Dec. 24, 2014.

PCT/US2014/055901 International Preliminary Report on Patentability dated Mar. 31, 2016.

PCT/US2014/055901 International Search Report and Written Opinion dated Dec. 24, 2014.

Saunders et al. Identification of small-molecule inhibitors of autotaxin that inhibit melanoma cell migration and invasion. Mol. Cancer Ther. 7:3352-3362 (2008).

Sonar et al. (Z)-3-(1H-Indol-3-yl)-2-(3-thienyl)-acrylo-nitrile and (Z)-3-[1-(4-tert-butyl-benzyl)-1H-indol-3-yl]-2-(3-thienyl)-acrylo-nitrile. Acta Cryst C61:o78-o080 (2005).

Tanaka et al. Efficient synthesis of 3-O-thia-cPA and preliminary analysis of its biological activity toward autotaxin. Bioorg. Med. Chem. Lett. 21:4180-4182 (2011).

Van Meeteren et al. Anticancer activity of FTY720: phosphorylated FTY720 inhibits autotaxin, a metastasis-enhancing and angiogenic lysophospholipase D. Cancer Lett. 266:203-208 (2008).

Van Meeteren et al. Inhibition of autotaxin by lysophosphatidic acid and sphingosine 1-phosphate. J. Biol. Chem. 280:21155-21161 (2005).

Venable et al. Preparation and biological evaluation of indole, benzimidazole, and thienopyrrole piperazine carboxamides: potent human histamine h(4) antagonists. J Med Chem 48(26):8289-8298 (2005).

Zhang et al. Dual activity lysophosphatidic acid receptor pan-antagonist/autotaxin inhibitor reduces breast cancer cell migration in vitro and causes tumor regression in vivo. Cancer Res 69:5441-5449 (2009).

Zhang et al. Synthesis of 1H-indazoles and 1H-pyrazoles via FeBr3/O2 mediated intramolucular C-H amination. J Org Chem 78(3):1317-1322 (2013).

Blanchard et al. Synthesis and evaluation of alkenyl indazoles as selective Aurora kinase inhibitors. Bioorg Med Chem Lett 20(8):2443-2447 (2010).

\* cited by examiner

VINYL AUTOTAXIN INHIBITOR COMPOUNDS

RELATED APPLICATIONS

This application is filed pursuant to 35 U.S.C. 371 as a United States National Phase Application of International Application No. PCT/US2014/055901 entitled "VINYL AUTOTAXIN INHIBITOR COMPOUNDS" filed Sep. 16, 2014, which claims the benefit of U.S. Provisional Application No. 61/878,922 entitled "VINYL AUTOTAXIN INHIBITOR COMPOUNDS" filed Sep. 17, 2013, the content of which each application is hereby incorporated by reference in its entirety.

FIELD OF THE INVENTION

Described herein are compounds that are autotaxin inhibitors, methods of making such compounds, pharmaceutical compositions and medicaments comprising such compounds, and methods of using such compounds in the treatment of conditions, diseases, or disorders associated with autotaxin activity.

BACKGROUND OF THE INVENTION

Lysophosphatidic acid (LPA) is a lipid mediator that functions, for example, as a mitogen, chemoattractant, and survival factor for many cell types. LPA signaling is implicated in, for example, cancer, angiogenesis, chronic inflammation, autoimmune diseases, fibrotic diseases, neurodegenerative diseases, reperfusion injury post stroke or myocardial ischemia, reproduction and tumor progression.

SUMMARY OF THE INVENTION

Compounds described herein are autotaxin (ATX) inhibitors. In some embodiments, the autotaxin inhibitors described herein are useful as agents for the treatment or prevention of diseases or conditions in which ATX and/or LPA participates, is involved in the etiology or pathology of the disease, or is otherwise associated with at least one symptom of the disease. Inhibition of the physiological activity of ATX and/or LPA is useful in a variety of diseases or conditions. The ATX-LPA signaling pathway has been implicated in fibrotic diseases, cancer, pruritus, angiogenesis, inflammation, autoimmune diseases, reproduction and tumor progression.

As described herein, compounds of Formula (I), Formula (II), Formula (III), Formula (IV), Formula (V), Formula (VI), or Formula (VII), or a pharmaceutically acceptable salt or solvate thereof, are used in the treatment of diseases or conditions in which autotaxin activity contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology. In one aspect, the methods, compounds, pharmaceutical compositions, and medicaments described herein comprise autotaxin inhibitors.

In one aspect, the compounds of Formula (I), Formula (II), Formula (III), Formula (IV), Formula (V), Formula (VI), or Formula (VII), or a pharmaceutically acceptable salt or solvate thereof, are useful for the treatment of diseases or conditions such as, but not limited to, fibrosis, cell proliferative disease, inflammatory disease, autoimmune diseases, reproductive diseases, abnormal angiogenesis-associated diseases, scleroderma, brain or heart reperfusion injury, neurodegenerative diseases, neuropathic pain, peripheral neuropathy, ocular disease, diabetic retinopathy, proliferative vitreoretinopathy, cicatricial pemphigoid, and glaucoma.

In one aspect, described herein is a compound of Formula (I), or a pharmaceutically acceptable salt, pharmaceutically acceptable solvate, or prodrug thereof:

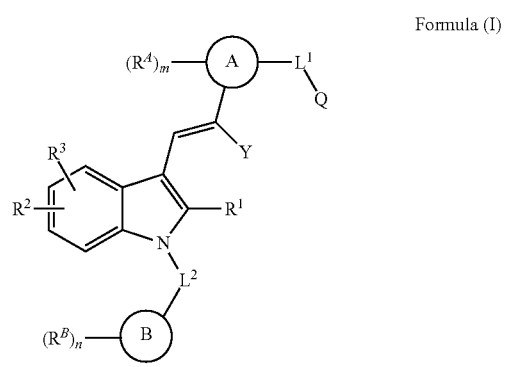

Formula (I)

wherein, $R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl;

$R^2$ is halogen, —CN, —OH, —$OR^9$, —$NO_2$, —$NH_2$, —$N(R^{10})_2$, —OC(=O)$N(R^{10})_2$, —C(=O)$N(R^{10})_2$, —NHC(=O)$R^9$, —NHC(=O)$OR^9$, substituted or unsubstituted $C_1$-$C_4$alkyl, $C_1$-$C_4$fluoroalkyl, $C_1$-$C_4$deuteroalkyl, substituted or unsubstituted $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, $C_1$-$C_4$hydroxyalkyl or substituted or unsubstituted phenyl, monocyclic heteroaryl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each $R^4$ is independently selected from the group consisting of H, halogen, —CN, —$NO_2$, —OH, —$OR^9$, —$SR^9$, —$S(=O)R^9$, —$S(=O)_2R^9$, —$S(=O)_2N(R^{10})_2$, —$NR^{10}S(=O)_2R^9$, —C(=O)$R^9$, —OC(=O)$R^9$, —$CO_2R^{10}$, —$OCO_2R^9$, —$N(R^{10})_2$, —C(=O)$N(R^{10})_2$, —OC(=O)$N(R^{10})_2$, —NHC(=O)$R^9$, —NHC(=O)$OR^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;

m is 0, 1, or 2;

$L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$;

X is O, S, S(=O), S(=O)$_2$, C(=O)NH, NHC(=O), NH, OC(=O)NH, NHC(=O)O, or NHC(=O)O;

p is 0 or 1;

q is 0 or 1;

Q is —$CO_2H$, —$CO_2(C_1$-$C_6$alkyl), —OH, —CN, —$B(OH)_2$, —$C(=O)NHSO_2R^9$, —$C(=O)N(R^{10})_2$, —$SO_2NHC(=O)R^9$, —CN, tetrazolyl, —$OP(=O)(OH)_2$, —$P(=O)(OH)_2$ or carboxylic acid bioisostere;

$L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent;

Y is H, $C_1$-$C_6$alkyl, halogen, or CN;

Ring B is a monocyclic aryl, bicyclic aryl, monocyclic heteroaryl or bicyclic heteroaryl;

each $R^B$ is independently selected from the group consisting of H, halogen, —CN, —$NO_2$, —OH, —$OR^9$, —$SR^9$, —$S(=O)R^9$, —$S(=O)_2R^9$, —$S(=O)_2N(R^{10})_2$, —$NR^{10}S(=O)_2R^9$, —$C(=O)R^9$, —$OC(=O)R^9$, —$CO_2R^{10}$, —$OCO_2R^9$, —$N(R^{10})_2$, —$C(=O)N(R^{10})_2$, —$OC(=O)N(R^{10})_2$, —$NHC(=O)R^9$, —$NHC(=O)OR^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl;

n is 0, 1, or 2;

each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, —$C_1$-$C_4$alkylene-(substituted or unsubstituted monocyclic heteroaryl), a substituted or unsubstituted bicyclic heteroaryl and —$C_1$-$C_4$alkylene-(substituted or unsubstituted bicyclic heteroaryl);

each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, and —$C_1$-$C_4$alkylene-(substituted or unsubstituted monocyclic heteroaryl); or two $R^{10}$ groups attached to the same N atom are taken together with the N atom to which they are attached to form a substituted or unsubstituted heterocycle.

For any and all of the embodiments, substituents are selected from among a subset of the listed alternatives. For example, in some embodiments, $R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl. For example, in some embodiments, $R^1$ is H, halogen, —CN, —C(=O)H, $C_1$-$C_4$alkyl, $C_1$-$C_4$fluoroalkyl, or $C_1$-$C_4$deuteroalkyl. In other embodiments, $R^1$ is H, halogen, —CN, —C(=O)H, $C_1$-$C_4$alkyl, or $C_1$-$C_4$fluoroalkyl. In yet other embodiments, $R^1$ is H, halogen, —CN, —C(=O)H, or $C_1$-$C_4$alkyl. In some embodiments, $R^1$ is H, D, F, Cl, —$CH_3$, —$CF_3$, or —$CD_3$. In some embodiments, $R^1$ is H or —$CH_3$. In some embodiments, $R^1$ is H.

In some embodiments, $R^1$ is H, halogen, —CN, —C(=O)H, $C_1$-$C_4$alkyl, $C_1$-$C_4$fluoroalkyl, or $C_1$-$C_4$deuteroalkyl; $R^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; Ring A is a monocyclic aryl, bicyclic aryl, monocyclic heteroaryl or bicyclic heteroaryl; each $R^A$ is independently selected from the group consisting of H, halogen, —CN, —$NO_2$, —OH, —$OR^9$, —$SR^9$, —$S(=O)R^9$, —$S(=O)_2R^9$, —$S(=O)_2N(R^{10})_2$, —$NR^{10}S(=O)_2R^9$, —$C(=O)R^9$, —$OC(=O)R^9$, —$CO_2R^{10}$, —$OCO_2R^9$, —$N(R^{10})_2$, —$C(=O)N(R^{10})_2$, —$OC(=O)N(R^{10})_2$, —$NHC(=O)R^9$, —$NHC(=O)OR^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;

m is 0, 1, or 2; $L^1$ is absent, $C_1$-$C_6$alkylene, $C_1$-$C_6$fluoroalkylene, $C_3$-$C_6$cycloalkylene, $(C_1$-$C_6$alkylene)$_p$-$C_3$-$C_6$cycloalkylene-$(C_1$-$C_6$alkylene)$_q$, or —($C_1$-$C_6$alkylene)$_p$-X—($C_1$-$C_6$alkylene)$_q$; X is O, S, S(=O), S(=O)$_2$, C(=O)NH, NHC(=O), NH, OC(=O)NH, NHC(=O)O, or NHC(=O)O; p is 0 or 1; q is 0 or 1; Q is —$CO_2H$, —$CO_2(C_1$-$C_6$alkyl), —OH, —CN, —$B(OH)_2$, —$C(=O)NHSO_2R^9$, —$C(=O)N(R^{10})_2$, —$SO_2NHC(=O)R^9$, —CN, tetrazolyl, —$OP(=O)(OH)_2$, —$P(=O)(OH)_2$ or carboxylic acid bioisostere; $L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent; Y is H, $C_1$-$C_6$alkyl, halogen, or CN; Ring B is a monocyclic aryl, bicyclic aryl, monocyclic heteroaryl or bicyclic heteroaryl; each $R^B$ is independently selected from the group consisting of H, halogen, —CN, —$NO_2$, —OH, —$OR^9$, —$SR^9$, —$S(=O)R^9$, —$S(=O)_2R^9$, —$S(=O)_2N(R^{10})_2$, —$NR^{10}S(=O)_2R^9$, —$C(=O)R^9$, —$OC(=O)R^9$, —$CO_2R^{10}$, —$OCO_2R^9$, —$N(R^{10})_2$, —$C(=O)N(R^{10})_2$, —$OC(=O)N(R^{10})_2$, —$NHC(=O)R^9$, —$NHC(=O)OR^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl; n is 0, 1, or 2; each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, and a substituted or unsubstituted bicyclic heteroaryl; each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, and a substituted or unsubstituted monocyclic heteroaryl; or two $R^{10}$ groups attached to the same N atom are taken together with the N atom to which they are attached to form a substituted or unsubstituted heterocycle.

In some embodiments, $L^2$ is absent, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-

$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or —$C_1$-$C_6$alkylene-; Y is H, $C_1$-$C_6$alkyl, halogen, or CN.

In some embodiments, $L^2$ is absent, or —$C_1$-$C_6$alkylene-; Y is H, $C_1$-$C_6$alkyl, halogen, or CN.

In some embodiments, Y is H, $C_1$-$C_6$alkyl, halogen, or CN.

In some embodiments, $L^2$ is absent, —$CH_2$—, —$CH_2CH_2$—, —$CH_2CH_2CH_2$—, or —$CH(CH_3)$—.

In some embodiments, $L^2$ is absent. In some embodiments, $L^2$ is —$CH_2$—, —$CH_2CH_2$—, —$CH_2CH_2CH_2$—, or —$CH(CH_3)$—. In some embodiments, $L^2$ is —$CH_2$—.

In some embodiments, $R^1$ is H, F, Cl, —CN, —C(=O)H, —$CH_3$, —$CF_3$, or —$CD_3$. In some embodiments, $R^1$ is H or —$CH_3$. In some embodiments, $R^1$ is —$CH_3$.

In some embodiments, $L^1$ is absent, —$CH_2$—, —$CH_2CH_2$—, —$CH_2CH_2CH_2$—, —$CH(CH_3)$—, —$CH(CH_2CH_3)$—, —$C(CH_3)_2$—, —$C(CH_2CH_3)_2$—, cyclopropyl-1,1-diyl, cyclobutyl-1,1-diyl, cyclopentyl-1,1-diyl or cyclohexyl-1,1-diyl; Q is —$CO_2H$, —$CO_2(C_1$-$C_6$alkyl), —C(=O)NHSO$_2R^9$ or tetrazolyl.

In some embodiments, $L^2$ is —$C_1$-$C_6$alkylene-; Y is H, —$CH_3$, F, Cl, Br, or CN.

In some embodiments, $L^1$ is absent, —$CH_2$—, —$CH_2CH_2$—, —$CH_2CH_2CH_2$—, —$CH(CH_3)$—, —$CH(CH_2CH_3)$—, —$C(CH_3)_2$—, —$C(CH_2CH_3)_2$—, cyclopropyl-1,1-diyl, cyclobutyl-1,1-diyl, cyclopentyl-1,1-diyl or cyclohexyl-1,1-diyl; Q is —$CO_2H$, —$CO_2(C_1$-$C_6$alkyl), —C(=O)NHSO$_2R^9$ or tetrazolyl.

In some embodiments, $R^1$ is H, F, Cl, —CN, —C(=O)H, —$CH_3$, —$CF_3$, or —$CD_3$.

In some embodiments, the compound of Formula (I) has the following structure of Formula (II):

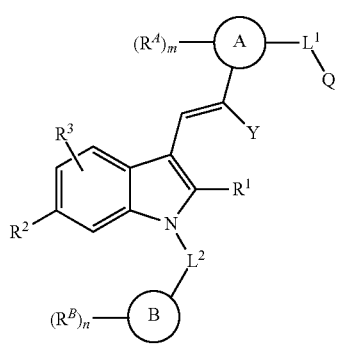

Formula (II)

or is a pharmaceutically acceptable salt, or solvate thereof.

In some embodiments, the compound of Formula (I) has the following structure of Formula (III), Formula (IV), or Formula (V):

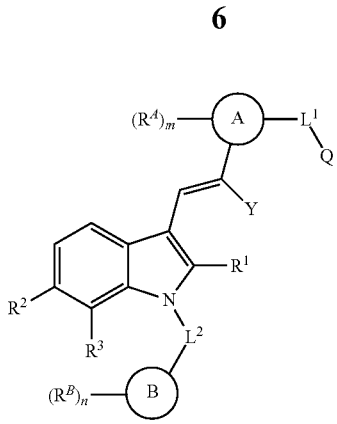

Formula (III)

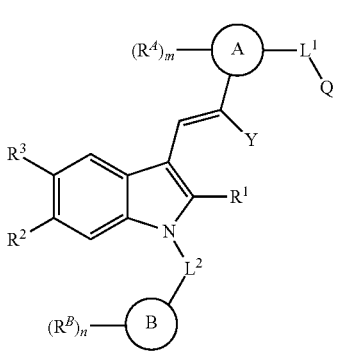

Formula (IV)

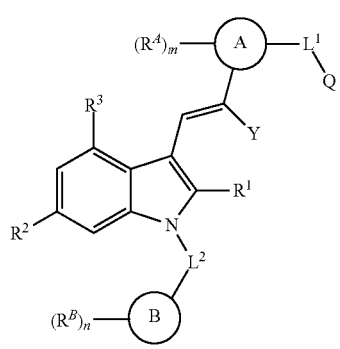

Formula (V)

or is a pharmaceutically acceptable salt, or solvate thereof.

In some embodiments, $L^2$ is —$CH_2$—, —$CH_2CH_2$—, —$CH_2CH_2CH_2$—, or —$CH(CH_3)$—.

In some embodiments, Ring A is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms; Ring B is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms.

In some embodiments, Ring A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring A is phenyl or naphthyl. In some embodiments, Ring A is phenyl.

In some embodiments, the compound of Formula (I) has the following structure of Formula (VI):

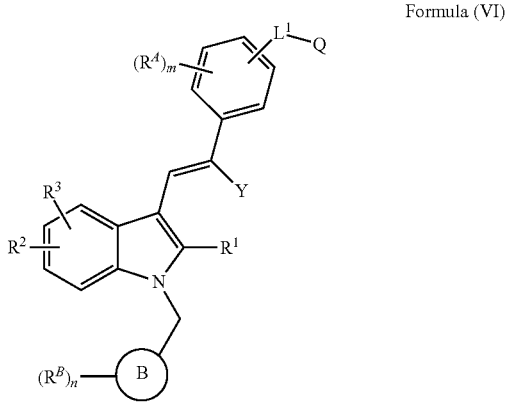

Formula (VI)

or is a pharmaceutically acceptable salt, or solvate thereof.

In some embodiments, the compound of Formula (I) has the following structure of Formula (VII):

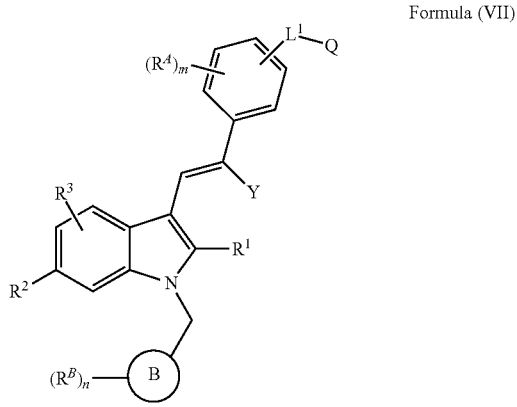

Formula (VII)

or is a pharmaceutically acceptable salt, or solvate thereof.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring A is pyridinyl, pyrimidinyl, pyrazinyl, pyridazinyl, or triazinyl. In some embodiments, Ring A is pyridinyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, each $R^4$ is independently selected from the group consisting of H, halogen, —CN, —OH, —$OR^9$, $C_1$-$C_6$alkyl, and $C_1$-$C_6$fluoroalkyl.

In some embodiments, Ring B is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring B is phenyl or naphthyl. In some embodiments, Ring B is phenyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments, Ring B is pyridinyl, pyrimidinyl, pyrazinyl, pyridazinyl, or triazinyl. In some embodiments, Ring B is pyridinyl.

In some embodiments, Ring B is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, $R^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^2$ is F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$.

In some embodiments, $R^2$ is Cl.

In some embodiments, $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^3$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$.

In some embodiments, $R^3$ is H, F, or Cl.

In some embodiments, $L^1$ is absent, —$CH_2$—, —$CH_2CH_2$—, or —$CH_2CH_2CH_2$—; Q is —$CO_2H$, or —$CO_2(C_1$-$C_6$alkyl)$. In some embodiments, $L^1$ is absent; Q is —$CO_2H$.

In some embodiments, $R^1$ is H, —$CH_3$, —$CF_3$, or —$CD_3$; $L^1$ is absent, —$CH_2$—, —$CH_2CH_2$—, or —$CH_2CH_2CH_2$—; Q is —$CO_2H$, or —$CO_2(C_1$-$C_6$alkyl)$. In some embodiments, $R^1$ is —$CH_3$, —$CF_3$, or —$CD_3$; $L^1$ is absent, —$CH_2$—, —$CH_2CH_2$—, or —$CH_2CH_2CH_2$—; Q is —$CO_2H$, or —$CO_2(C_1$-$C_6$alkyl)$. In some embodiments, $R^1$ is H; $L^1$ is absent or —$CH_2$—; Q is —$CO_2H$.

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound of Formula (I), or a pharmaceutically acceptable salt, or solvate thereof, and at least one pharmaceutically acceptable excipient:

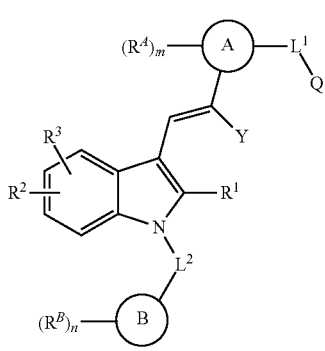

Formula (I)

wherein,
R$^1$ is H, D, halogen, —CN, —C(=O)H, C$_1$-C$_4$alkyl, C$_3$-C$_6$cycloalkyl, C$_1$-C$_4$fluoroalkyl, or C$_1$-C$_4$deuteroalkyl;
R$^2$ is H, halogen, —CN, —OH, —OR$^9$, —NO$_2$, —NH$_2$, —N(R$^{10}$)$_2$, —OC(=O)N(R$^{10}$)$_2$, —C(=O)N(R$^{10}$)$_2$, —NHC(=O)R$^9$, —NHC(=O)OR$^9$, substituted or unsubstituted C$_1$-C$_4$alkyl, C$_1$-C$_4$fluoroalkyl, C$_1$-C$_4$deuteroalkyl, substituted or unsubstituted C$_1$-C$_4$alkoxy, C$_1$-C$_4$fluoroalkoxy, —S—C$_1$-C$_4$alkyl, —S(=O)—C$_1$-C$_4$alkyl, —S(=O)$_2$—C$_1$-C$_4$alkyl, C$_1$-C$_4$hydroxyalkyl or substituted or unsubstituted phenyl, monocyclic heteroaryl;
R$^3$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, C$_1$-C$_4$fluoroalkoxy, —S—C$_1$-C$_4$alkyl, —S(=O)—C$_1$-C$_4$alkyl, —S(=O)$_2$—C$_1$-C$_4$alkyl, or C$_1$-C$_4$hydroxyalkyl;
Ring A is a monocyclic aryl, bicyclic aryl, monocyclic heteroaryl or bicyclic heteroaryl;
  each R$^4$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted C$_1$-C$_6$alkyl, C$_1$-C$_6$fluoroalkyl, C$_1$-C$_6$deuteroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, and substituted or unsubstituted monocyclic heteroaryl;
  m is 0, 1, or 2;
L$^1$ is absent, C$_1$-C$_6$alkylene, C$_1$-C$_6$fluoroalkylene, C$_3$-C$_6$cycloalkylene, (C$_1$-C$_6$alkylene)$_p$-C$_3$-C$_6$cycloalkylene-(C$_1$-C$_6$alkylene)$_q$, or —(C$_1$-C$_6$alkylene)$_p$-X—(C$_1$-C$_6$alkylene)$_q$;
  X is O, S, S(=O), S(=O)$_2$, C(=O)NH, NHC(=O), NH, OC(=O)NH, NHC(=O)O, or NHC(=O)O;
  p is 0 or 1;
  q is 0 or 1;
Q is —CO$_2$H, —CO$_2$(C$_1$-C$_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;
L$^2$ is —C$_1$-C$_6$alkylene-, —C(=O)—, —C(=O)—C$_1$-C$_6$alkylene-, —C(=O)NH—, —C(=O)NH—C$_1$-C$_6$alkylene-, —C(=O)O—, —C(=O)O—C$_1$-C$_6$alkylene-, —C$_1$-C$_6$alkylene-C(=O)—, —C$_1$-C$_6$alkylene-C(=O)NH—, —C$_1$-C$_6$alkylene-NHC(=O)—, —C$_1$-C$_6$alkylene-C(=O)O—, —C$_1$-C$_6$alkylene-OC(=O)—, —C$_1$-C$_6$alkylene-OC(=O)NH—, —C$_1$-C$_6$alkylene-NHC(=O)NH—, or absent;
Y is H, C$_1$-C$_6$alkyl, halogen, or CN;
Ring B is a monocyclic aryl, bicyclic aryl, monocyclic heteroaryl or bicyclic heteroaryl;
  each R$^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted C$_1$-C$_6$alkyl, C$_1$-C$_6$fluoroalkyl, C$_1$-C$_6$deuteroalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted phenyl, substituted or unsubstituted monocyclic heteroaryl, and a substituted or unsubstituted bicyclic heteroaryl;
  n is 0, 1, or 2;
each R$^9$ is independently selected from the group consisting of C$_1$-C$_6$alkyl, C$_1$-C$_6$fluoroalkyl, C$_1$-C$_6$deuteroalkyl, C$_3$-C$_6$cycloalkyl, a substituted or unsubstituted phenyl, —C$_1$-C$_4$alkylene-(substituted or unsubstituted phenyl), a substituted or unsubstituted monocyclic heteroaryl, —C$_1$-C$_4$alkylene-(substituted or unsubstituted monocyclic heteroaryl), a substituted or unsubstituted bicyclic heteroaryl and —C$_1$-C$_4$alkylene-(substituted or unsubstituted bicyclic heteroaryl);
each R$^{10}$ is independently selected from the group consisting of H, C$_1$-C$_6$alkyl, C$_1$-C$_6$fluoroalkyl, C$_1$-C$_6$deuteroalkyl, C$_3$-C$_6$cycloalkyl, a substituted or unsubstituted phenyl, —C$_1$-C$_4$alkylene-(substituted or unsubstituted phenyl), a substituted or unsubstituted monocyclic heteroaryl, and —C$_1$-C$_4$alkylene-(substituted or unsubstituted monocyclic heteroaryl); or
two R$^{10}$ groups attached to the same N atom are taken together with the N atom to which they are attached to form a substituted or unsubstituted heterocycle.

In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition further comprises one or more additional therapeutically active agents in addition to the compound of Formula (I), Formula (II), Formula (III), Formula (IV), Formula (V), Formula (VI), or Formula (VII), or a pharmaceutically acceptable salt or solvate thereof. Additional therapeutic agents include, but are not limited to, immunosuppressants, ant-fibrotic agents, analgesics, anti-cancer agents, and anti-inflammatories. For example, such agents include, but are not limited to, corticosteroids, immunosuppressants, analgesics, anti-cancer agents, anti-inflammatories, non-steroidal anti-inflammatories, TNF-alpha blockers, kinase inhibitors, chemokine receptor antagonists, bronchodilators, leukotriene receptor antagonists, leukotriene formation inhibitors, prostaglandin receptor antagonists, prostaglandin formation inhibitors, monoacylglycerol kinase inhibitors, phospholipase A$_1$ inhibitors, phospholipase $A_2$ inhibitors, lysophospholipase D (lysoPLD) inhibitors, autotaxin inhibitors, and LPA receptor antagonists.

In some embodiments of the pharmaceutical composition, $R^1$ is H, halogen, —CN, —C(=O)H, $C_1$-$C_4$alkyl, $C_1$-$C_4$fluoroalkyl, or $C_1$-$C_4$deuteroalkyl; $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; Ring A is a monocyclic aryl, bicyclic aryl, monocyclic heteroaryl or bicyclic heteroaryl; each $R^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$ cycloalkyl, substituted or unsubstituted $C_2$-$C_{10}$heterocycloalkyl, substituted or unsubstituted phenyl, and substituted or unsubstituted monocyclic heteroaryl; m is 0, 1, or 2; $L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$; X is O, S, S(=O), S(=O)$_2$, C(=O)NH, NHC(=O), NH, OC(=O)NH, NHC(=O)O, or NHC(=O)O; p is 0 or 1; q is 0 or 1; Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere; $L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_{10}$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent; Y is H, $C_1$-$C_6$alkyl, halogen, or CN; Ring B is a monocyclic aryl, bicyclic aryl, monocyclic heteroaryl or bicyclic heteroaryl; each $R^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl; n is 0, 1, or 2; each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, and a substituted or unsubstituted bicyclic heteroaryl; each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, and a substituted or unsubstituted monocyclic heteroaryl; or two $R^{10}$ groups attached to the same N atom are taken together with the N atom to which they are attached to form a substituted or unsubstituted heterocycle.

In some embodiments of the pharmaceutical composition, $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl. In some embodiments of the pharmaceutical composition, $R^2$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH. In some embodiments of the pharmaceutical composition, $R^2$ is H or Cl.

In some embodiments of the pharmaceutical composition, $R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl; $R^2$ is halogen, —CN, —OH, —OR$^9$, —NO$_2$, —NH$_2$, —N(R$^{10}$)$_2$, —OC(=O)N(R$^{10}$)$_2$, —C(=O)N(R$^{10}$)$_2$, —NHC(=O)R$^9$, —NHC(=O)OR$^9$, substituted or unsubstituted $C_1$-$C_4$alkyl, $C_1$-$C_4$fluoroalkyl, $C_1$-$C_4$deuteroalkyl, substituted or unsubstituted $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, $C_1$-$C_4$hydroxyalkyl or substituted or unsubstituted phenyl, monocyclic heteroaryl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; Ring A is a monocyclic aryl, bicyclic aryl, monocyclic heteroaryl or bicyclic heteroaryl; each $R^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl; m is 0, 1, or 2; $L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$; X is O, S, S(=O), S(=O)$_2$, C(=O)NH, NHC(=O), NH, OC(=O)NH, NHC(=O)O, or NHC(=O)O; p is 0 or 1; q is 0 or 1; Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere; $L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent; Y is H, $C_1$-$C_6$alkyl, halogen, or CN; Ring B is a monocyclic aryl, bicyclic aryl, monocyclic heteroaryl or bicyclic heteroaryl; each $R^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl; n is 0, 1, or 2; each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, —$C_1$-$C_4$alkylene-(substituted or unsubstituted monocyclic heteroaryl), a substituted or unsubstituted bicyclic heteroaryl and —$C_1$-$C_4$alkylene-(substituted or unsubstituted bicyclic heteroaryl); each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, and —$C_1$-$C_4$alkylene-(substituted or unsubstituted monocyclic heteroaryl); or two $R^{10}$ groups attached to the same N atom are taken together with the N atom to which they are attached to form a substituted or unsubstituted heterocycle.

In some embodiments of the pharmaceutical composition, $R^1$ is H, halogen, —CN, —C(=O)H, $C_1$-$C_4$alkyl, $C_1$-$C_4$fluoroalkyl, or $C_1$-$C_4$deuteroalkyl; $R^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; Ring A is a monocyclic aryl, bicyclic aryl, monocyclic heteroaryl or bicyclic heteroaryl; each $R^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl; m is 0, 1, or 2; $L^1$ is absent, $C_1$-$C_6$alkylene, $C_1$-$C_6$fluoroalkylene, $C_3$-$C_6$cycloalkylene, ($C_1$-$C_6$ alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$; X is O, S, S(=O), S(=O)$_2$, C(=O)NH, NHC(=O), NH, OC(=O)NH, NHC(=O)O, or NHC(=O)O; p is 0 or 1; q is 0 or 1; Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere; $L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent; Y is H, $C_1$-$C_6$alkyl, halogen, or CN; Ring B is a monocyclic aryl, bicyclic aryl, monocyclic heteroaryl or bicyclic heteroaryl; each $R^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl; n is 0, 1, or 2; each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, and a substituted or unsubstituted bicyclic heteroaryl; each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, and a substituted or unsubstituted monocyclic heteroaryl; or two $R^{10}$ groups attached to the same N atom are taken together with the N atom to which they are attached to form a substituted or unsubstituted heterocycle.

In some embodiments of the pharmaceutical composition, $R^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl. In some embodiments of the pharmaceutical composition, $R^2$ is F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH. In some embodiments of the pharmaceutical composition, $R^2$ is Cl.

In some embodiments of the pharmaceutical composition, $L^2$ is —$C_1$-$C_6$alkylene-; Y is H, —CH$_3$, F, Cl, Br, or CN.

In some embodiments of the pharmaceutical composition, $L^1$ is absent, —CH$_2$—, —CH$_2$CH$_2$—, —CH$_2$CH$_2$CH$_2$—, —CH(CH$_3$)—, —CH(CH$_2$CH$_3$)—, —C(CH$_3$)$_2$—, —C(CH$_2$CH$_3$)$_2$—, cyclopropyl-1,1-diyl, cyclobutyl-1,1-diyl, cyclopentyl-1,1-diyl or cyclohexyl-1,1-diyl; Q is —CO$_2$H, —CO$_2$($C_1$-$C_6$alkyl), —C(=O)NHSO$_2$R$^9$ or tetrazolyl.

In some embodiments of the pharmaceutical composition, $R^1$ is H, F, Cl, —CN, —C(=O)H, —CH$_3$, —CF$_3$, or —CD$_3$.

In some embodiments of the pharmaceutical composition, the compound has the structure of Formula (II). In some embodiments of the pharmaceutical composition, the compound has the structure of Formula (III). In some embodiments of the pharmaceutical composition, the compound has the structure of Formula (IV). In some embodiments of the pharmaceutical composition, the compound has the structure of Formula (V).

In some embodiments of the pharmaceutical composition, $L^2$ is —CH$_2$—, —CH$_2$CH$_2$—, —CH$_2$CH$_2$CH$_2$—, or —CH(CH$_3$)—.

In some embodiments of the pharmaceutical composition, Ring A is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms; Ring B is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms.

In some embodiments of the pharmaceutical composition, Ring A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments of the pharmaceutical composition, Ring A is phenyl or naphthyl.

In some embodiments of the pharmaceutical composition, the compound has the structure of Formula (VI). In some embodiments of the pharmaceutical composition, the compound has the structure of Formula (VII).

In some embodiments of the pharmaceutical composition, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments of the pharmaceutical composition, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl. In some embodiments of the pharmaceutical composition, Ring A is pyridinyl, pyrimidinyl, pyrazinyl, pyridazinyl, or triazinyl. In some embodiments of the pharmaceutical composition, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments of the pharmaceutical composition, each $R^A$ is independently selected from the group consisting of H, halogen, —CN, —OH, —OR$^9$, $C_1$-$C_6$alkyl, and $C_1$-$C_6$fluoroalkyl.

In some embodiments of the pharmaceutical composition, Ring B is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl. In some embodiments of the pharmaceutical composition, Ring B is phenyl or naphthyl. In some embodiments of the pharmaceutical composition, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments of the pharmaceutical composition, Ring B is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl. In some embodiments of the pharmaceutical composition, Ring B is pyridinyl, pyrimidinyl, pyrazinyl, pyridazinyl, or triazinyl. In some embodiments of the pharmaceutical composition, Ring B is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments of the pharmaceutical composition, $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl. In some embodiments of the pharmaceutical composition, $R^3$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH. In some embodiments of the pharmaceutical composition, $R^3$ is H, F, or Cl.

In some embodiments of the pharmaceutical composition, $L^1$ is absent, —CH$_2$—, —CH$_2$CH$_2$—, or —CH$_2$CH$_2$CH$_2$—; Q is —CO$_2$H, or —CO$_2$(C$_1$-C$_6$alkyl).

In one aspect, described herein is a method of treating or preventing any one of the diseases or conditions described herein comprising administering a therapeutically effective amount of a compound described herein (e.g. Formula (I), Formula (II), Formula (III), Formula (IV), Formula (V), Formula (VI), or Formula (VII)), or a pharmaceutically acceptable salt, or solvate thereof, to a mammal in need thereof.

In another aspect is the use of a compound of Formula (I), Formula (II), Formula (III), Formula (IV), Formula (V), Formula (VI), or Formula (VII), or a pharmaceutically acceptable salt thereof, in the treatment or prevention of a disease or condition in which the activity of autotaxin and/or at least one LPA receptor contributes to the pathology and/or symptoms of the disease or condition. In one aspect, the disease or condition is any of the diseases or conditions described herein.

In one aspect, described is a method for treating or preventing cancer, fibrosis, pruritis, an inflammatory disease or condition, an airway disease or condition, an autoimmune disease or condition, obesity, intraocular pressure, neuropathic pain, or combinations thereof in a mammal comprising administering a therapeutically effective amount of a compound of Formula (I), or a pharmaceutically acceptable salt, or solvate thereof, to the mammal in need thereof.

In another aspect, described is a method for treating or preventing cancer in a mammal comprising administering a therapeutically effective amount of a compound of Formula (I), Formula (II), Formula (III), Formula (IV), Formula (V), Formula (VI), or Formula (VII), or a pharmaceutically acceptable salt, or solvate thereof, to the mammal in need thereof. In some embodiments, the cancer is a solid tumor. In some embodiments, the cancer is bladder cancer, colon cancer, brain cancer, breast cancer, endometrial cancer, heart cancer, kidney cancer, lung cancer, liver cancer, uterine cancer, blood and lymphatic cancer, ovarian cancer, pancreatic cancer, prostate cancer, thyroid cancer, or skin cancer. In yet other embodiments, the cancer is a sarcoma, carcinoma, or lymphoma. In some embodiments, the cancer is amendable to treatment with an autotaxin inhibitor. In some embodiments, the method further comprises administering a second therapeutic agent to the mammal in addition to the compound of Formula (I), Formula (II), Formula (III), Formula (IV), Formula (V), Formula (VI), or Formula (VII), or a pharmaceutically acceptable salt, or solvate thereof.

In one aspect, described herein is a method for the treatment or prevention of fibrosis in a mammal comprising administering a therapeutically effective amount of a compound of Formula (I), Formula (II), Formula (III), Formula (IV), Formula (V), Formula (VI), or Formula (VII), or a pharmaceutically acceptable salt, or solvate thereof, to the mammal in need thereof. In some embodiments, the fibrosis comprises lung fibrosis, liver fibrosis, kidney fibrosis or cutaneous fibrosis. In some embodiments, the fibrosis is amendable to treatment with an autotaxin inhibitor. In some embodiments, the method further comprises administering a second therapeutic agent to the mammal in addition to the compound of Formula (I), Formula (II), Formula (III), Formula (IV), Formula (V), Formula (VI), or Formula (VII), or a pharmaceutically acceptable salt, or solvate thereof.

In one aspect, described herein is a method of reducing or inhibiting angiogenesis in a mammal comprising administering a therapeutically effective amount of a compound of Formula (I), Formula (II), Formula (III), Formula (IV), Formula (V), Formula (VI), or Formula (VII), or a pharmaceutically acceptable salt, or solvate thereof, to the mammal in need thereof. In some embodiments, reducing or inhibiting angiogenesis in the mammal treats atherosclerosis, hypertension, tumor growth, inflammation, rheumatoid arthritis, wet-form macular degeneration, choroidal neovascularization, retinal neovascularization, or diabetic retinopathy.

In one aspect, described herein is a method of treating or preventing an inflammatory disease or condition in a mammal comprising administering a therapeutically effective amount of a compound of Formula (I), Formula (II), Formula (III), Formula (IV), Formula (V), Formula (VI), or Formula (VII), or a pharmaceutically acceptable salt, or solvate thereof, to the mammal in need thereof. In some embodiments, the inflammatory disease or condition is psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, lupus erythematosus, dermatomyositis, Sjogren's syndrome, thyroiditis, myasthenia gravis, autoimmune hemolytic anemia, multiple sclerosis, cystic fibrosis, chronic relapsing hepatitis, primary biliary cirrhosis, primary sclerosing cholangitis, allergic conjunctivitis or atopic dermatitis.

In one aspect, described herein is a method for treating or preventing pruritis in a mammal comprising administering a therapeutically effective amount of a compound of Formula (I), Formula (II), Formula (III), Formula (IV), Formula (V), Formula (VI), or Formula (VII), or a pharmaceutically acceptable salt, or solvate thereof, to the mammal in need thereof. In some embodiments, the pruiritus is associated with dermatitis herpetiformis, dermatomyositis, pemphigoid, Sjögren's syndrome, Darier's disease, Hailey-Hailey disease, Ichthyoses, Sjögren-Larsson syndrome, dermatophytosis, folliculitis, impetigo and other bacterial infections, insect bites, pediculosis, ccabies, viral infection, asteatosis, atopic eczema, contact dermatitis, drug reaction, lichen planus, lichen simplex chronicus, mastocytosis (urticaria pigmentosa), miliaria, psoriasis, scar(s), urticaria, cutaneous T-cell lymphoma or mycosis fungoides, cutaneous B-cell lymphoma, leukemia cutis, pemphigoid gestationis, polymorphic eruption of pregnancy or prurigo gestationis.

In one aspect, described herein is a method for treating or preventing cholestatic pruritis in a mammal comprising administering a therapeutically effective amount of a compound of Formula (I), Formula (II), Formula (III), Formula (IV), Formula (V), Formula (VI), or Formula (VII), or a pharmaceutically acceptable salt, or solvate thereof, to the mammal in need thereof.

In any of the aforementioned aspects are further embodiments in which the effective amount of the compound of Formula (I), Formula (II), Formula (III), Formula (IV), Formula (V), Formula (VI), or Formula (VII), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of ATX dependent diseases or conditions are further embodiments comprising administering at least one additional agent in addition to the administration of a compound having the structure of Formula (I), Formula (II), Formula (III), Formula (IV), Formula (V), Formula (VI), or Formula (VII), or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound of Formula (I), Formula (II), Formula (III), Formula (IV), Formula (V), Formula (VI), or Formula (VII), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of autotaxin, or for the treatment, prevention or amelioration of one or more symptoms of a disease or condition that would benefit from inhibition of the activity of autotaxin, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Autotaxin and LPA

Autotaxin (ATX, NPP2, or E-NPP2), an approximately 120 kDa glycoprotein, is a secreted nucleotide pyrophosphatase/phosphodiesterase (NPP) with lysophospholipase D activity that converts extracellular lysophosphatidylcholine (LPC) and other lysophospholipids to lysophosphatidic acid (LPA). ATX is considered to be responsible for the majority of circulating LPA production.

LPA acts through sets of specific G protein-coupled receptors (GPCRs), such as LPA1, LPA2, LPA3, LPA4, LPA5, LPA6, LPA7, LPA8, in an autocrine and paracrine fashion to produce a variety of biological responses. For example, lysophospholipids, such as lysophatidic acid (LPA), are known to affect such biological functions as cellular proliferation, differentiation, survival, migration, adhesion, invasion, and morphogenesis. In addition, LPA is known to play a role in such processes as platelet activation, smooth muscle contraction, actin stress fiber formation, and cell migration.

ATX and LPA have been detected in various biological fluids such as serum, plasma, cerebrospinal fluid, seminal fluid, urine, and saliva, both in animals and humans, suggesting that they are potential biomarkers to predict certain diseases. For example, serum ATX concentration and activity is elevated in patients with chronic liver diseases and in pregnant women. In addition, ATX concentration has been found to be lower in postoperative cancer patients as a result of postoperative damage or poor nutritional state. In addition, ATX is known to be essential for normal development. For example, ATX-deficient mice die at embryonic day 9.5 with profound vascular defects in both the yolk sac and the embryo. Furthermore, at embryonic day 8.5 ATX-deficient embryos were found to have malformed allantois, neural tube defects, and asymmetric headfolds.

Cancer

ATX has been demonstrated to increase cell motility, neovascularization, proliferation and aggressiveness of tumors. It is upregulated in numerous tumor lineages, such as breast, renal, liver, glioblastoma, ovarian and prostate cancer.

In some embodiments, disclosed herein are methods of treating cancer with a compound disclosed herein.

ATX is a prometastatic enzyme initially isolated from the conditioned medium of human melanoma cells. In addition, ATX overexpression is frequently observed in malignant tumor tissues such as breast cancer, renal cancer, Hodgkin lymphoma, hepatocellular carcinoma, pancreatic cancer and glioblastoma. LPA also contributes to tumorigenesis by increasing motility and invasiveness of cells.

The term "cancer" as used herein, refers to an abnormal growth of cells that tend to proliferate in an uncontrolled way and, in some cases, to metastasize (spread). Types of cancer include, but are not limited to, solid tumors (such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, desmoid tumors, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, a compound of Formula (I), Formula (II), Formula (III), Formula (IV), Formula (V), Formula (VI), or Formula (VII), or a pharmaceutically acceptable salt thereof, is used in the treatment of ovarian cancer, prostate cancer, breast cancer, lung cancer, melanoma, head and neck cancer, bowel cancer (colorectal cancer), thyroid cancer, glioblastoma, follicular lymphoma, renal cancer, Hodgkin lymphoma, hepatocellular carcinoma, pancreatic cancer or melanoma.

In some embodiments, a compound of Formula (I), Formula (II), Formula (III), Formula (IV), Formula (V), Formula (VI), or Formula (VII), or a pharmaceutically acceptable salt thereof, is used in the treatment of bone metastases.

In some embodiments, a compound of Formula (I), Formula (II), Formula (III), Formula (IV), Formula (V), Formula (VI), or Formula (VII), or a pharmaceutically acceptable salt thereof, is used in the treatment of oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In some embodiments, a compound of Formula (I), Formula (II), Formula (III), Formula (IV), Formula (V), Formula (VI), or Formula (VII), or a pharmaceutically acceptable salt thereof, is used in the treatment of non-small cell lung cancer, pancreatic cancer, breast cancer, ovarian cancer, colorectal cancer, or head and neck cancer.

In some embodiments, a compound of Formula (I), Formula (II), Formula (III), Formula (IV), Formula (V), Formula (VI), or Formula (VII), or a pharmaceutically acceptable salt thereof, is used in the treatment of a carcinoma, a tumor, a neoplasm, a lymphoma, a melanoma, a glioma, a sarcoma, or a blastoma.

In some embodiments, the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In some embodiments, the tumor is selected from the group consisting of: astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma.

In some embodiments, the neoplasm is selected from the group consisting of: intaepithelial neoplasia, multiple myeloma/plasma cell neoplasm, plasma cell neoplasm, interepithelial squamous cell neoplasia, endometrial hyperplasia, focal nodular hyperplasia, hemangioendothelioma, lymphangioleio myomatosis and malignant thymoma.

In some embodiments, the lymphoma is selected from the group consisting of: nervous system lymphoma, AIDS-related lymphoma, cutaneous T-cell lymphoma, non-Hodgkin's lymphoma, mantle cell lymphoma, follicular lymphoma and Waldenstrom's macroglobulinemia.

In some embodiments, the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In some embodiments, the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In some embodiments, the glioma is selected from the group consisting of: glioma, brain stem glioma, and hypothalamic and visual pathway glioma.

In some embodiments, the blastoma is selected from the group consisting of: pulmonary blastoma, pleuropulmonary blastoma, retinoblastoma, neuroblastoma, medulloblastoma, glioblastoma, and hemangiblastomas.

Fibrosis

In some embodiments, disclosed herein are methods of treating fibrosis with a compound disclosed herein.

"Fibrosis," as used herein, refers to the accumulation of extracellular matrix constituents that occurs following trauma, inflammation, tissue repair, immunological reactions, cellular hyperplasia, and neoplasia. Examples of tissue fibrosis include, but are not limited to, pulmonary fibrosis, renal fibrosis, cardiac fibrosis, cirrhosis and fibrosis of the liver, skin scars and keloids, adhesions, fibromatosis, atherosclerosis, and amyloidosis.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is primary fibrosis. In some embodiments, the fibrotic condition is idiopathic. In some embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, or a combination thereof.

In some embodiments, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, or hematopoietic tissue.

In some embodiments, the fibrotic condition is a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, or bronchiectasis. In some embodiments, the fibrosis of the lung is secondary to a disease, a toxin, an insult, a medical treatment, or a combination thereof. In some embodiments, fibrosis of the lung is associated with one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In some embodiments, the fibrotic condition of the lung treated with the methods of the invention is associated with (e.g., secondary to) a cancer treatment, e.g., treatment of a cancer (e.g. squamous cell carcinoma, testicular cancer, Hodgkin's disease with bleomycin).

In some embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In some embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In some embodiments, the myocardial fibrosis is associated with an inflammatory disorder of cardiac tissue (e.g., myocardial sarcoidosis).

In some embodiments, the fibrotic condition is a fibrotic condition of the kidney. In some embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent.

In some embodiments, the fibrotic condition is a fibrotic condition of the skin. In some embodiments, the fibrotic condition of the skin is chosen from one or more of: skin fibrosis, scleroderma, nephrogenic systemic fibrosis (e.g., resulting after exposure to gadolinium which is frequently used as a contrast substance for MRIs in patients with severe kidney failure), scarring and keloid.

In some embodiments, the fibrotic condition is a fibrotic condition of the gastrointestinal tract. In some embodiments, the fibrotic condition is chosen from one or more of fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease.

In some embodiments, the fibrotic condition is adhesions. In some embodiments, the adhesions are chosen from one or more of: abdominal adhesions, peritoneal adhesions, pelvic adhesions, pericardial adhesions, peridural adhesions, peritendinous or adhesive capsulitis.

In some embodiments, the fibrotic condition is a fibrotic condition of the eye. In some embodiments, the fibrotic condition of the eye involves diseases of the anterior segment of the eye such as glaucoma and corneal opacification; in some embodiments, the fibrotic condition of the eye involves disease of the posterior segment of the eye such as age-related macular degeneration, diabetic retinopathy, retinopathy of prematurity and neovascular glaucoma; in some embodiments, the fibrotic condition of the eye results from fibrosis following ocular surgery.

In some embodiments, the fibrotic condition is a fibrotic condition of the bone marrow or a hematopoietic tissue. In some embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In some embodiments, the bone marrow fibrosis is associated with (e.g., is secondary to) a malignant condition or a condition caused by a clonal proliferative disease. In some embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In some embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency.

Pruritis

In some embodiments, disclosed herein are methods of treating pruritis with a compound disclosed herein.

Pruritus is a condition involving localized or general itching that is a common and distressing symptom in a variety of diseases. Although usually occurring in the skin, pruritus can also occur in non-cutaneous sites such as mucous membranes. Pruritus is a frequent manifestation of localized skin disorders caused by hypersensitivity reactions such as allergic reactions to insect bites or to environmental allergens, urticaria, dermatoses of fungal and bacterial origins, ectoparasite infections, and hemorrhoids. In some embodiments, disclosed herein are method of treating pruritus caused by systemic diseases, including, for example, hypothyroidism, thyrotoxicosis, mucocandiasis in diabetes mellitus, and Hodgkin's disease. In some embodiments, disclosed herein are methods of treating bouts of persistent or recurrent pruritus associated with many systemic diseases and skin disorders.

In some embodiments, disclosed herein are methods of treating pruritus associated with liver diseases and intrahepatic or posthepatic cholestasis. Hepatic diseases leading to pruritus include primary biliary cirrhosis, B and C viral hepatitis, primary sclerosing cholangitis, carcinoma of bile ducts, alcoholic cirrhosis, autoimmune hepatitis and others.

In some embodiments, disclosed herein are method of treating pruritus arising from a variety of causes such as xerosis, skin conditions (such as psoriasis, eczema, sunburn, athlete's foot), insect bites, poisonous plants (such as poison ivy, poison oak, poison sumac), Hodgkin's disease, jaundice, polycythemia, scabies, lice, worms, thyroid illness, diabetes mellitus, dandruff, iron deficiency anemia, parasitic infections, medications, cholestasis, pruritus related to pregnancy, HIV infection or other causes of itching or pruritus.

Inflammation

In some embodiments, disclosed herein are methods of treating an inflammatory condition, disease, or disorder with a compound disclosed herein.

As used in the present disclosure, "inflammation" refers to the well known localized response to various types of injury or infection, which is characterized by redness, heat, swelling, and pain, and often also including dysfunction or reduced mobility.

Airway Diseases

Inflammatory conditions, diseases, and disorders, which can be treated with a compound disclosed herein, include airway diseases comprising pulmonary inflammation, such as chronic obstructive pulmonary disease (COPD), cystic fibrosis, and asthma. COPD is comprised primarily of two related diseases: chronic bronchitis and emphysema. In both diseases, there is chronic obstruction of the flow of air through the airways and out of the lungs, and the obstruction generally is permanent and progressive over time Asthma is a chronic disease of the airways of the lungs, characterized by inflammation and paradoxical narrowing of the bronchi. Asthma includes asthmatic conditions mediated via T-cell action, including extrinsic asthma (allergic asthma), intrinsic asthma (non-allergic asthma), mixed asthma (extrinsic and intrinsic asthma), occupational asthma induced by agents such as toluene diisocyanate, polyvinyl chloride, phthalic anhydride, trimellitic anhydride, plicatic acid (Western Red Cedar trees) or metal salts such as platinum or nickel), drug-induced asthma (including aspirin-induced asthma or asthma induced by non-steroidal anti-inflammatory drugs (NSAIDs)), exercise-induced asthma, and cough variant asthma. In some embodiments, the asthma is an allergic or non-allergic asthmatic condition mediated by T-cell function.

In some embodiments, disclosed herein is a method of treating asthma with a compound disclosed herein. In an asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In some embodiments, ATX and/or LPA contribute to these structural changes in the airway. In some embodiments, ATX and/or LPA are involved in acute airway hyperresponsiveness in asthma. The lumen of the remodeled asthmatic airway is narrower due to the thickening of the airway wall, thus decreasing airflow. In some embodiments, LPA contributes to the long-term structural remodeling and the acute hyper-responsiveness of the asthmatic airway. In some embodiments, LPA contributes to the hyper-responsiveness that is a primary feature of acute exacerbations of asthma.

In some embodiments, disclosed herein is a method of treating or preventing COPD with a compound disclosed herein. The term "chronic obstructive pulmonary disease (COPD)" refers to a group of lung diseases, including chronic bronchitis, emphysema and obliterative bronchiolitis. The most common of these diseases are chronic bronchitis and emphysema. Although a person with COPD may have either chronic bronchitis or emphysema, he or she will often have a mixture of the symptoms of these two conditions. Although emphysema usually results from damage to the lungs caused by environmental insult, usually as a result of long-term smoking, emphysema may also be caused by congenital absence of α1-antitrypsin in the lungs; this type of emphysema is usually inherited.

In some embodiments, disclosed herein is a method of treating chronic bronchitis with a compound disclosed herein. Chronic bronchitis (CB) is inflammation of one or more bronchi, usually secondary to infection, and is characterized by excessive production of mucus in the bronchi, accompanied by a recurrent cough which persists for at least three months of the year during at least two successive years. CB is the major non-asthmatic disease of the lung. Many different factors initiate CB, including cigarette smoking, environmental pollution, chronic infections and various genetic abnormalities. Of these factors, cigarette smoking is the most prevalent. Pathological changes in the lung include: (1) hypertrophy and hyperplasia of mucus-secreting glands in the bronchi, (2) increase in goblet cells, (3) disappearance or damage of cilia, and (4) chronic inflammatory changes and narrowing of small airways.

In some embodiments, disclosed herein is a method of treating emphysema with a compound disclosed herein. Emphysema is a lung condition which results from damage to the alveolar sacs in the lungs, usually caused by long-term smoking. This damage leads to a pathological accumulation of air in the tissues.

Administration of LPA in vivo induces airway hyperresponsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. In some embodiments, disclosed herein is a method of reducing plasma exudation due to an acute allergic reaction with a compound disclosed herein.

Autoimmune Diseases

The methods described herein, in some embodiments, include methods for the treatment, reduction of risk, and delaying of onset of an autoimmune disease or disorder with a compound disclosed herein. Examples of autoimmune diseases include, but are not limited to, Alopecia Areata, Lupus, Ankylosing Spondylitis, Meniere's Disease, Antiphospholipid Syndrome, Mixed Connective Tissue Disease, Autoimmune Addison's Disease, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjögren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Diabetes (Type II), Vasculitis, Lichen Planus, and Vitiligo.

Other Inflammatory Disorders

The methods described herein, in some embodiments, include methods for the treatment, reduction of risk, and delaying onset of other inflammatory conditions or diseases with a compound disclosed herein, such as (a Ocular inflammation associated with corneal ulcers, giant papillary conjunctivitis, blepharitis, chelazion, uveitis, dry eye, post-surgical inflammation, and contact lens associated inflammation; (b) allergic diseases such as hay fever, rhinitis, seasonal allergic conjunctivitis, vernal conjunctivitis and other eosinophil-mediated conditions; (c) skin diseases such as psoriasis, contact dermatitis, eczema, infectious skin ulcers, open wounds, and cellulitis; (d) infectious diseases including sepsis, septic shock, encephalitis, infectious arthritis, endotoxic shock, gram negative shock, Jarisch-Herxheimer reaction, shingles, toxic shock, cerebral malaria, bacterial meningitis, acute respiratory distress syndrome (ARDS), lyme disease, and HIV infection, (e) wasting diseases such as cachexia secondary to cancer and HIV; (f) inflammation due to organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, e.g., interleukin-2 treatment, adverse effects from OKT3 treatment, adverse effects from GM-CSF treatment, adverse effects of cyclosporine treatment, and adverse effects of aminoglycoside treatment, stomatitis, and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal-induced inflammation due to burns, acid, alkali and the like.

Obesity

In some embodiments, disclosed herein are methods of treating obesity and/or diabetes with a compound disclosed herein.

ATX is responsible for the lysoPLD activity released by adipocytes and exerts a paracrine control on preadipocyte growth via an LPA-dependent mechanism. In addition, ATX is up-regulated during adipocyte differentiation and in genetic obesity. In certain instances, ATX mRNA is up-regulated in adipocytes from db/db mice suggesting that the up-regulation of ATX is related to the severe type 2 diabetes phenotype and adipocyte insulin resistance. In some instances, up-regulation of ATX in adipocytes is associated with type 2 diabetes.

"Obesity," as used herein, refers to a medical condition in which excess body fat has accumulated to the extent that it may have an adverse effect on health, leading to increased health problems. In some embodiments, "obesity" refers to a weight increase, which is at least 5% of the total body weight. In some embodiments, disclosed herein is a method of treating postmenopausal obesity and/or visceral obesity with a compound disclosed herein.

Intraocular Pressure

In some embodiments, disclosed herein are methods of treating elevated intraocular pressure associated with glaucoma.

Glaucoma is one of the leading causes of blindness and is characterized by elevated intraocular pressure (IOP). IOP is a primary risk factor for developing glaucoma and the risk of developing glaucoma decreases when IOP is reduced. Ocular hypotensive therapy is the mainstay of glaucoma treatment. Elevated IOP results from diminished aqueous humor (AH) drainage through the trabecular pathway and autotaxin activity is an abundant protein in human AH. Autotaxin is secreted by human trabecular meshwork cells and ATX activity is significantly elevated from glaucoma patients. Inhibition of autotaxin activity in AH by topical and intracameral delivery of a small molecule inhibitor leads to decreased IOP in rabbits.

Neuropathic Pain

In some embodiments, disclosed herein are methods of treating neuropathic pain with a compound disclosed herein.

LPA induces neuropathic pain as well as demyclination and pain-related protein expression changes via LPA1. In some instances, ATX heterozygous knockout mice show about 50% recovery of nerve injury-induced neuropathic pain compared to wild type mice. Lysophosphatidylcholine (LPC), is known to induce neuropathic pain. In certain instances, LPC-induced neuropathic pain is partially reduced in ATX heterozygous knockout mice.

Neuropathic pain results from injury to a nerve. In contrast to immediate pain caused by tissue injury, in some embodiments, neuropathic pain develops days or months after a traumatic injury. In addition, neuropathic pain frequently is long-lasting or chronic and can occur spontaneously or as a result of stimulation that normally is not painful.

Compounds

Compounds of Formula (I), including pharmaceutically acceptable salts, prodrugs, active metabolites and pharmaceutically acceptable solvates thereof, are autotaxin inhibitors. In one aspect, provided herein is a compound of Formula (I), or a pharmaceutically acceptable salt, solvate, metabolite or prodrug thereof:

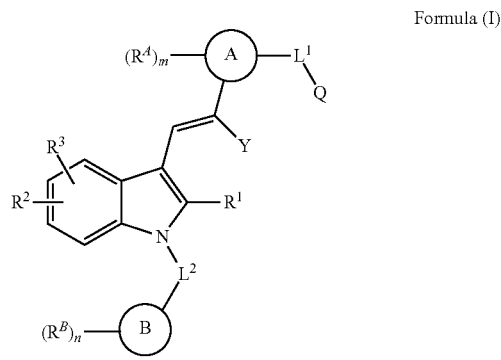

Formula (I)

wherein, $R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl;

$R^2$ is H, halogen, —CN, —OH, —$OR^9$, —$NO_2$, —$NH_2$, —$N(R^{10})_2$, —OC(=O)$N(R^{10})_2$, —C(=O)$N(R^{10})_2$, —NHC(=O)$R^9$, —NHC(=O)$OR^9$, substituted or unsubstituted $C_1$-$C_4$alkyl, $C_1$-$C_4$fluoroalkyl, $C_1$-$C_4$deuteroalkyl, substituted or unsubstituted $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, $C_1$-$C_4$hydroxyalkyl or substituted or unsubstituted phenyl, monocyclic heteroaryl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each $R^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;

m is 0, 1, or 2;

$L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$;

X is O, S, S(=O), S(=O)$_2$, C(=O)NH, NHC(=O), NH, OC(=O)NH, NHC(=O)O, or NHC(=O)O;

p is 0 or 1;

q is 0 or 1;

Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;

$L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent;

Y is H, $C_1$-$C_6$alkyl, halogen, or CN;

Ring B is a monocyclic aryl, bicyclic aryl, monocyclic heteroaryl or bicyclic heteroaryl;

each $R^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl;

n is 0, 1, or 2;

each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, —$C_1$-$C_4$alkylene-(substituted or unsubstituted monocyclic heteroaryl), a substituted or unsubstituted bicyclic heteroaryl and —$C_1$-$C_4$alkylene-(substituted or unsubstituted bicyclic heteroaryl);

each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, and —$C_1$-$C_4$alkylene-(substituted or unsubstituted monocyclic heteroaryl); or two $R^{10}$ groups attached to the same N atom are taken together with the N atom to which they are attached to form a substituted or unsubstituted heterocycle.

For any and all of the embodiments, substituents are selected from among a subset of the listed alternatives. For example, in some embodiments, $R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl. For example, in some embodiments, $R^1$ is H, halogen, —CN, —C(=O)H, $C_1$-$C_4$alkyl, $C_1$-$C_4$fluoroalkyl, or $C_1$-$C_4$deuteroalkyl. In other embodiments, $R^1$ is H, halogen, —CN, —C(=O)H, $C_1$-$C_4$alkyl, or $C_1$-$C_4$fluoroalkyl. In yet other embodiments, $R^1$ is H, halogen, —CN, —C(=O)H, or $C_1$-$C_4$alkyl. In some embodiments, $R^1$ is H, D, F, Cl, —CH$_3$, —CF$_3$, or —CD$_3$. In some embodiments, $R^1$ is H or —CH$_3$. In some embodiments, $R^1$ is H.

In some embodiments, $R^1$ is H, halogen, —CN, —C(=O)H, $C_1$-$C_4$alkyl, $C_1$-$C_4$fluoroalkyl, or $C_1$-$C_4$deuteroalkyl; $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; Ring A is a monocyclic aryl, bicyclic aryl, monocyclic heteroaryl or bicyclic heteroaryl; each $R^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl; m is 0, 1, or 2; $L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$; X is O, S, S(=O), S(=O)$_2$, C(=O)NH, NHC(=O), NH, OC(=O)NH, NHC(=O)O, or NHC(=O)O; p is 0 or 1; q is 0 or 1; Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere; $L^2$ is —$C_1$-$C_6$alkylene-, —C(=O)—, —C(=O)—$C_1$-$C_{10}$alkylene-, —C(=O)NH—, —C(=O)NH—$C_1$-$C_6$alkylene-, —C(=O)O—, —C(=O)O—$C_1$-$C_{10}$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent; Y is H, $C_1$-$C_6$alkyl, halogen, or CN; Ring B is a monocyclic aryl, bicyclic aryl, monocyclic heteroaryl or bicyclic heteroaryl; each $R^B$ is independently selected from the group consisting of H, halogen, —CN, —$NO_2$, —OH, —$OR^9$, —$SR^9$, —S(=O)$R^9$, —S(=O)$_2R^9$, —S(=O)$_2$N($R^{10}$)$_2$, —$NR^{10}$S(=O)$_2R^9$, —C(=O)$R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl; n is 0, 1, or 2; each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, and a substituted or unsubstituted bicyclic heteroaryl; each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, and a substituted or unsubstituted monocyclic heteroaryl; or two $R^{10}$ groups attached to the same N atom are taken together with the N atom to which they are attached to form a substituted or unsubstituted heterocycle.

In some embodiments, $R^1$ is not H when $R^2$ is H and $R^3$ is H. In some embodiments, $R^1$ is not H when $R^2$ is H. In some embodiments, $R^1$ is not H when $R^3$ is H. In some embodiments, $R^2$ is not H when $R^3$ is H.

In some embodiments, described herein is a compound of Formula (I), or a pharmaceutically acceptable salt, solvate, metabolite or prodrug thereof:

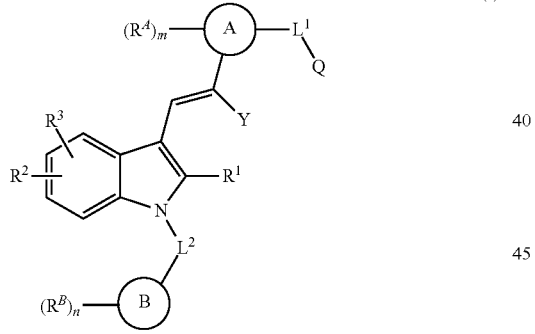

Formula (I)

wherein,
$R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl;

$R^2$ is halogen, —CN, —OH, —$OR^9$, —$NO_2$, —$NH_2$, —N($R^{10}$)$_2$, —OC(=O)N($R^{10}$)$_2$, —C(=O)N($R^{10}$)$_2$, —NHC(=O)$R^9$, —NHC(=O)$OR^9$, substituted or unsubstituted $C_1$-$C_4$alkyl, $C_1$-$C_4$fluoroalkyl, $C_1$-$C_4$deuteroalkyl, substituted or unsubstituted $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, $C_1$-$C_4$hydroxyalkyl or substituted or unsubstituted phenyl, monocyclic heteroaryl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;
  each $R^A$ is independently selected from the group consisting of H, halogen, —CN, —$NO_2$, —OH, —$OR^9$, —$SR^9$, —S(=O)$R^9$, —S(=O)$_2R^9$, —S(=O)$_2$N($R^{10}$)$_2$, —$NR^{10}$S(=O)$_2R^9$, —C(=O)$R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;
m is 0, 1, or 2;
$L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$;
X is O, S, S(=O), S(=O)$_2$, C(=O)NH, NHC(=O), NH, OC(=O)NH, NHC(=O)O, or NHC(=O)O;
p is 0 or 1;
q is 0 or 1;
Q is —$CO_2$H, —$CO_2$($C_1$-$C_6$alkyl), —OH, —CN, —B(OH)$_2$, —C(=O)NHSO$_2R^9$, —C(=O)N($R^{10}$)$_2$, —$SO_2$NHC(=O)$R^9$, —CN, tetrazolyl, —OP(=O)(OH)$_2$, —P(=O)(OH)$_2$ or carboxylic acid bioisostere;
$L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent;
Y is H, $C_1$-$C_6$alkyl, halogen, or CN;
Ring B is a monocyclic aryl, bicyclic aryl, monocyclic heteroaryl or bicyclic heteroaryl;
  each $R^B$ is independently selected from the group consisting of H, halogen, —CN, —$NO_2$, —OH, —$OR^9$, —$SR^9$, —S(=O)$R^9$, —S(=O)$_2R^9$, —S(=O)$_2$N($R^{10}$)$_2$, —$NR^{10}$S(=O)$_2R^9$, —C(=O)$R^9$, —OC(=O)$R^9$, —$CO_2R^{10}$, —$OCO_2R^9$, —N($R^{10}$)$_2$, —C(=O)N($R^{10}$)$_2$, —OC(=O)N($R^{10}$)$_2$, —NHC(=O)$R^9$, —NHC(=O)$OR^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl;
n is 0, 1, or 2;
each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, —$C_1$-$C_4$alkylene-(substituted or unsubstituted monocyclic heteroaryl), a substituted or unsubstituted bicyclic heteroaryl and —$C_1$-$C_4$alkylene-(substituted or unsubstituted bicyclic heteroaryl);

each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, and —$C_1$-$C_4$alkylene-(substituted or unsubstituted monocyclic heteroaryl); or two $R^{10}$ groups attached to the same N atom are taken together with the N atom to which they are attached to form a substituted or unsubstituted heterocycle.

In some embodiments, $R^1$ is H, halogen, —CN, —C(=O)H, $C_1$-$C_4$alkyl, $C_1$-$C_4$fluoroalkyl, or $C_1$-$C_4$deuteroalkyl; $R^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl; Ring A is a monocyclic aryl, bicyclic aryl, monocyclic heteroaryl or bicyclic heteroaryl; each $R^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl; m is 0, 1, or 2; $L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$; X is O, S, S(=O), S(=O)$_2$, C(=O)NH, NHC(=O), NH, OC(=O)NH, NHC(=O)O, or NHC(=O)O; p is 0 or 1; q is 0 or 1; Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere; $L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent; Y is H, $C_1$-$C_6$alkyl, halogen, or CN; Ring B is a monocyclic aryl, bicyclic aryl, monocyclic heteroaryl or bicyclic heteroaryl; each $R^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl; n is 0, 1, or 2; each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, and a substituted or unsubstituted bicyclic heteroaryl; each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, and a substituted or unsubstituted monocyclic heteroaryl; or two $R^{10}$ groups attached to the same N atom are taken together with the N atom to which they are attached to form a substituted or unsubstituted heterocycle.

In some embodiments, $L^2$ is absent, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or —$C_1$-$C_6$alkylene-; Y is H, $C_1$-$C_6$alkyl, halogen, or CN.

In some embodiments, $L^2$ is absent, or —$C_1$-$C_6$alkylene-; Y is H, $C_1$-$C_6$alkyl, halogen, or CN.

In some embodiments, Y is H, $C_1$-$C_6$alkyl, halogen, or CN. In some embodiments, Y is H, or CN. In some embodiments, Y is CN. In some embodiments, Y is H.

In some embodiments, $L^2$ is absent, —CH$_2$—, —CH$_2$CH$_2$—, —CH$_2$CH$_2$CH$_2$—, or —CH(CH$_3$)—.

In some embodiments, $L^2$ is absent. In some embodiments, $L^2$ is —CH$_2$—, —CH$_2$CH$_2$—, —CH$_2$CH$_2$CH$_2$—, or —CH(CH$_3$)—. In some embodiments, $L^2$ is —CH$_2$—. In some embodiments, $L^2$ is absent or —CH$_2$—.

In some embodiments, $R^1$ is H, F, Cl, —CN, —C(=O)H, —CH$_3$, —CF$_3$, or —CD$_3$. In some embodiments, $R^1$ is H or —CH$_3$. In some embodiments, $R^1$ is —CH$_3$. In some embodiments, $R^1$ is H.

In some embodiments, $L^1$ is absent, —CH$_2$—, —CH$_2$CH$_2$—, —CH$_2$CH$_2$CH$_2$—, —CH(CH$_3$)—, —CH(CH$_2$CH$_3$)—, —C(CH$_3$)$_2$—, —C(CH$_2$CH$_3$)$_2$—, cyclopropyl-1,1-diyl, cyclobutyl-1,1-diyl, cyclopentyl-1,1-diyl or cyclohexyl-1,1-diyl; Q is —CO$_2$H, —CO$_2$($C_1$-$C_6$alkyl), —C(=O)NHSO$_2$R$^9$ or tetrazolyl.

In some embodiments, $L^2$ is —$C_1$-$C_6$alkylene-; Y is H, —CH$_3$, F, Cl, Br, or CN.

In some embodiments, $L^1$ is absent, —CH$_2$—, —CH$_2$CH$_2$—, —CH$_2$CH$_2$CH$_2$—, —CH(CH$_3$)—, —CH(CH$_2$CH$_3$)—, —C(CH$_3$)$_2$—, —C(CH$_2$CH$_3$)$_2$—, cyclopropyl-1,1-diyl, cyclobutyl-1,1-diyl, cyclopentyl-1,1-diyl or cyclohexyl-1,1-diyl; Q is —CO$_2$H, —CO$_2$($C_1$-$C_6$alkyl), —C(=O)NHSO$_2$R$^9$ or tetrazolyl.

In some embodiments, $R^1$ is H, F, Cl, —CN, —C(=O)H, —CH$_3$, —CF$_3$, or —CD$_3$. In some embodiments, $R^1$ is H, F, Cl, —CN, —C(=O)H, —CH$_3$. In some embodiments, $R^1$ is H, or —CH$_3$. In some embodiments, $R^1$ is H. In some embodiments, $R^1$ is —CH$_3$. In some embodiments, $R^1$ is —CN. In some embodiments, $R^1$ is —C(=O)H. In some embodiments, $R^1$ is F. In some embodiments, $R^1$ is Cl.

In some embodiments, the compound of Formula (I) has the following structure of Formula (II):

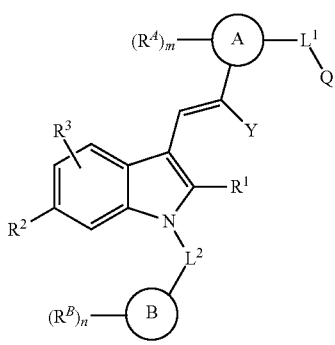

Formula (II)

or is a pharmaceutically acceptable salt, or solvate thereof.

In some embodiments, described herein is a compound that has the following structure of Formula (II):

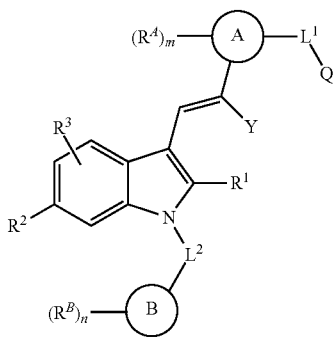

Formula (II)

wherein, $R^1$ is H, halogen, —CN, —C(=O)H, $C_1$-$C_4$alkyl, $C_1$-$C_4$fluoroalkyl, or $C_1$-$C_4$deuteroalkyl;

$R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each $R^A$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl;

m is 0, 1, or 2;

$L^1$ is absent, $C_1$-$C_6$alkylene, $C_1$-$C_6$fluoroalkylene, $C_3$-$C_6$cycloalkylene or —($C_1$-$C_6$alkylene)$_p$-X—($C_1$-$C_6$alkylene)$_q$;

X is O, S, S(=O), S(=O)$_2$, C(=O)NH, NHC(=O), NH, OC(=O)NH, NHC(=O)O, or NHC(=O)O;

p is 0 or 1;

q is 0 or 1;

Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;

$L^3$ is —CH=CY—;

$L^2$ is absent, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or —$C_1$-$C_6$alkylene-;

Y is H, $C_1$-$C_6$alkyl, halogen, or CN;

Ring B is a monocyclic aryl, bicyclic aryl, monocyclic heteroaryl or bicyclic heteroaryl;

each $R^B$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl or a substituted or unsubstituted bicyclic heteroaryl;

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle.

In some embodiments, described herein is a compound that has the following structure of Formula (II):

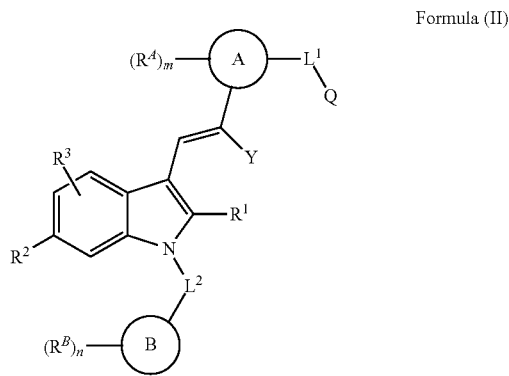

Formula (II)

wherein, $R^1$ is H, halogen, —CN, —C(=O)H, $C_1$-$C_4$alkyl, $C_1$-$C_4$fluoroalkyl, or $C_1$-$C_4$deuteroalkyl;

$R^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each $R^A$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, or substituted or unsubstituted monocyclic heteroaryl;

m is 0, 1, or 2;

$L^1$ is absent, $C_1$-$C_6$alkylene, $C_1$-$C_6$fluoroalkylene, $C_3$-$C_6$cycloalkylene or —($C_1$-$C_6$alkylene)$_p$-X—($C_1$-$C_6$alkylene)$_q$;

X is O, S, S(=O), S(=O)$_2$, C(=O)NH, NHC(=O), NH, OC(=O)NH, NHC(=O)O, or NHC(=O)O;

p is 0 or 1;

q is 0 or 1;

Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;

$L^3$ is —CH=CY—;

$L^2$ is absent, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or —$C_1$-$C_6$alkylene-;

Y is H, $C_1$-$C_6$alkyl, halogen, or CN;

Ring B is a monocyclic aryl, bicyclic aryl, monocyclic heteroaryl or bicyclic heteroaryl;

each $R^B$ is H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl or a substituted or unsubstituted bicyclic heteroaryl;

n is 0, 1, or 2;

$R^9$ is $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, or a substituted or unsubstituted bicyclic heteroaryl;

each $R^{10}$ is independently selected from H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, or a substituted or unsubstituted monocyclic heteroaryl; or two $R^{10}$ groups attached to the same N atom are taken together with the N atom to which they are attached to form a substituted or unsubstituted heterocycle.

In some embodiments, the compound of Formula (I) has the following structure of Formula (III), Formula (IV), or Formula (V):

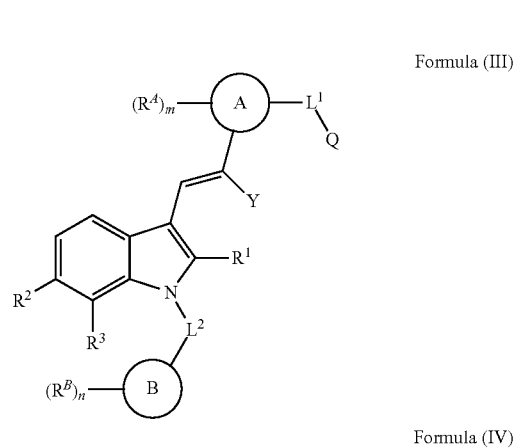

Formula (III)

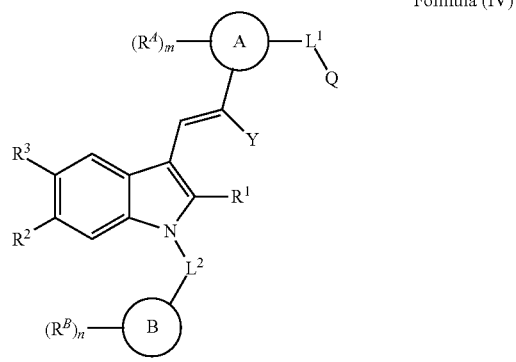

Formula (IV)

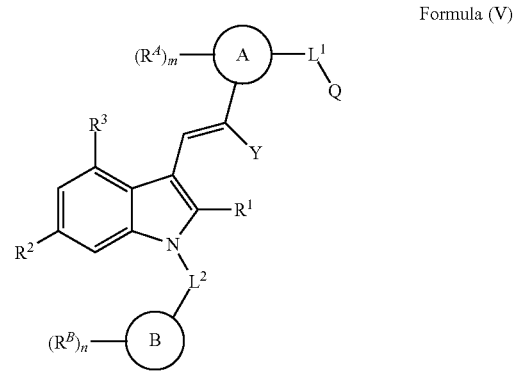

Formula (V)

or is a pharmaceutically acceptable salt, or solvate thereof.

In some embodiments, the compound of Formula (I) has the structure of Formula (III), or a pharmaceutically acceptable salt, or solvate thereof. In some embodiments, the compound of Formula (I) has the structure of Formula (IV), or a pharmaceutically acceptable salt, or solvate thereof. In some embodiments, the compound of Formula (I) has the structure of Formula (V), or a pharmaceutically acceptable salt, or solvate thereof.

In some embodiments, $L^2$ is —CH$_2$—, —CH$_2$CH$_2$—, —CH$_2$CH$_2$CH$_2$—, or —CH(CH$_3$)—.

In some embodiments, Ring A is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms; Ring B is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms.

In some embodiments, Ring A is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms.

In some embodiments, Ring A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring A is phenyl or naphthyl. In some embodiments, Ring A is phenyl.

In some embodiments, the compound of Formula (I) has the following structure of Formula (VI):

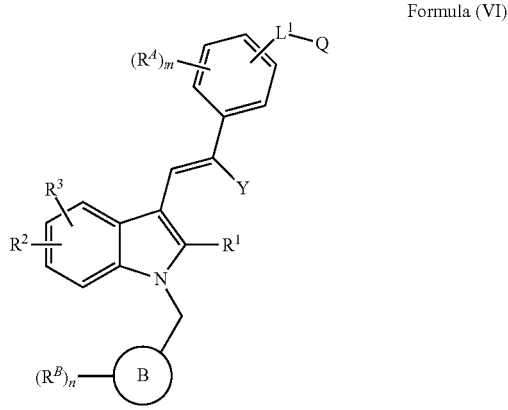

Formula (VI)

or a pharmaceutically acceptable salt, or solvate thereof.

In some embodiments, the compound of Formula (I) or Formula (II) has the following structure of Formula (VII):

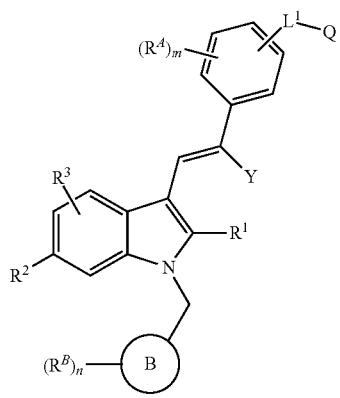

Formula (VII)

or a pharmaceutically acceptable salt, or solvate thereof.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring A is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl. In some embodiments, Ring A is thiazolyl.

In some embodiments, Ring A is pyridinyl, pyrimidinyl, pyrazinyl, pyridazinyl, or triazinyl. In some embodiments, Ring A is pyridinyl. In some embodiments, Ring A is pyrimidinyl.

In some embodiments, Ring A is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, each $R^A$ is independently selected from the group consisting of H, halogen, —CN, —OH, —OR$^9$, C$_1$-C$_6$alkyl, and C$_1$-C$_6$fluoroalkyl. In some embodiments, each $R^A$ is H.

In some embodiments, Ring B is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, Ring B is phenyl or naphthyl. In some embodiments, Ring B is phenyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments, Ring B is furanyl, pyrrolyl, oxazolyl, thiazolyl, imidazolyl, pyrazolyl, triazolyl, tetrazolyl, isoxazolyl, isothiazolyl, oxadiazolyl, or thiadiazolyl. In some embodiments, Ring B is thiazolyl.

In some embodiments, Ring B is pyridinyl, pyrimidinyl, pyrazinyl, pyridazinyl, or triazinyl. In some embodiments, Ring B is pyridinyl.

In some embodiments, Ring B is quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

In some embodiments, each $R^B$ is independently selected from the group consisting of H, halogen, —CN, —OH, —$OR^9$, $C_1$-$C_6$alkyl, and $C_1$-$C_6$fluoroalkyl. In some embodiments, each $R^B$ is H. In some embodiments, each $R^B$ is independently selected from the group consisting of fluoro or chloro. In some embodiments, each $R^B$ is independently selected from the group consisting of —$CH_3$ or —$CF_3$. In some embodiments, each $R^B$ is independently selected from the group consisting of —$OR^9$. In some embodiments, each $R^B$ is independently selected from the group consisting of —$OCH_3$, —$OCH_2CH_3$ or —$OCH_2CH_2CH_3$. In some embodiments, $R^B$ is —$OCH_3$ and n is 1. In some embodiments, $R^B$ is -fluoro and n is 1.

In some embodiments, $R^2$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl. In some embodiments, $R^2$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$. In some embodiments, $R^2$ is H, Cl, or —$OCF_3$. In some embodiments, $R^2$ is Cl. In some embodiments, $R^2$ is —$OCF_3$. In some embodiments, $R^2$ is H.

In some embodiments, $R^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl. In some embodiments, $R^2$ is F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$. In some embodiments, $R^2$ is Cl.

In some embodiments, $R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, or $C_1$-$C_4$hydroxyalkyl.

In some embodiments, $R^3$ is H, F, Cl, Br, I, —CN, —OH, —$CH_3$, —$CF_3$, —$CD_3$, —$OCH_3$, —$OCH_2CH_3$, —$OCF_3$, —$OCH_2CF_3$, or —$CH_2OH$.

In some embodiments, $R^3$ is H, F, or Cl. In some embodiments, $R^3$ is H. In some embodiments, $R^3$ is F.

In some embodiments, $L^1$ is absent, —$CH_2$—, —$CH_2CH_2$—, or —$CH_2CH_2CH_2$—; Q is —$CO_2H$, or —$CO_2(C_1$-$C_6$alkyl). In some embodiments, $L^1$ is absent; Q is —$CO_2H$.

In some embodiments, $R^1$ is H, —$CH_3$, —$CF_3$, or —$CD_3$; $L^1$ is absent, —$CH_2$—, —$CH_2CH_2$—, or —$CH_2CH_2CH_2$—; Q is —$CO_2H$, or —$CO_2(C_1$-$C_6$alkyl). In some embodiments, $R^1$ is —$CH_3$, —$CF_3$, or —$CD_3$; $L^1$ is absent, —$CH_2$—, —$CH_2CH_2$—, or —$CH_2CH_2CH_2$—; Q is —$CO_2H$, or —$CO_2(C_1$-$C_6$alkyl). In some embodiments, $R^1$ is H; $L^1$ is absent or —$CH_2$—; Q is —$CO_2H$.

In some embodiments, the compound of Formula (I) has

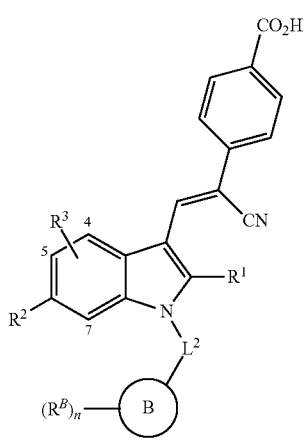

or a pharmaceutically acceptable salt, or solvate thereof.

In some embodiments,

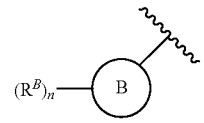

is as described in Table 1 or Table 2. In some embodiments,

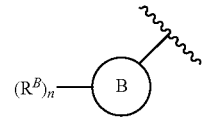

is 4-fluorophenyl or 2-methoxypyridin-5-yl. In some embodiments,

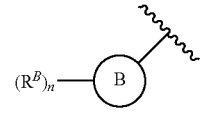

is 4-fluorophenyl. In some embodiments,

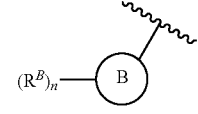

is 2-methoxypyridin-5-yl.
In some embodiments,

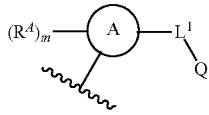

is 4-carboxyphenyl or as described in Table 2. In some embodiments,

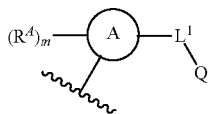

is as described in Table 2. In some embodiments,

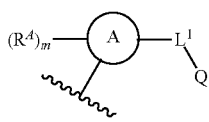

is 4-carboxyphenyl. In some embodiments, $R^1$ is as described in Table 1. In some embodiments, $R^3$ is as described in Table 1. In some embodiments, $R^2$ is as described in Table 1 or Table 2. In some embodiments, $R^2$ is not hydrogen. In some embodiments, $L^2$ is as described in Table 1 or Table 2.

Any combination of the groups described above for the various variables is contemplated herein. Throughout the specification, groups and substituents thereof are chosen by one skilled in the field to provide stable moieties and compounds.

Exemplary compounds of Formula (I) include the following compounds:

TABLE 1

| Compound number | $L^2$ | (R^B)_n—B | $R^1$ | $R^2$ | $R^3$ |
|---|---|---|---|---|---|
| 1-1 | —CH$_2$— | 4-fluorophenyl | H | H | H |
| 1-2 | —CH$_2$— | 4-fluorophenyl | H | H | 4-Cl |
| 1-3 | —CH$_2$— | 4-fluorophenyl | H | H | 5-Cl |
| 1-4 | —CH$_2$— | 4-fluorophenyl | H | Cl | H |
| 1-5 | —CH$_2$— | 4-fluorophenyl | H | H | 7-Cl |
| 1-6 | —CH$_2$— | 4-fluorophenyl | H | H | 5-F |
| 1-7 | —CH$_2$— | 4-fluorophenyl | H | F | H |
| 1-8 | —CH$_2$— | 4-fluorophenyl | H | Br | H |
| 1-9 | —CH$_2$— | 4-fluorophenyl | H | —CF$_3$ | H |
| 1-10 | —CH$_2$— | 4-fluorophenyl | H | MeO— | H |
| 1-11 | —CH$_2$— | 4-fluorophenyl | H | F | 4-F |
| 1-12 | — | 1-propyl-1H-pyrazol-4-yl | H | Cl | H |
| 1-13 | —CH$_2$— | phenyl | H | Cl | H |
| 1-14 | —CH$_2$— | pyridin-4-yl | H | Cl | H |
| 1-15 | —CH$_2$— | 2-trifluoromethylthiazol-5-yl | H | Cl | H |
| 1-16 | —CH$_2$— | 2-chloropyridin-5-yll | H | Cl | H |
| 1-17 | —CH$_2$— | 2-cthoxylthiazol-5-yl | H | Cl | H |
| 1-18 | —CH$_2$— | 3-propyl-1,2,4-oxadiazol-5-yl | H | Cl | H |
| 1-19 | —CH$_2$— | 3,5-dichlorophenyl | H | Cl | H |
| 1-20 | —CH$_2$— | 3,5-ditrifluoromethylphenyl | H | Cl | H |
| 1-21 | —CH$_2$— | 4-trifluoromethylphenyl | H | Cl | H |
| 1-22 | —CH$_2$CH$_2$— | 4-fluorophenyl | H | Cl | H |
| 1-23 | —CH$_2$CH$_2$CH$_2$— | 4-fluorophenyl | H | Cl | H |
| 1-24 | —CH$_2$CH$_2$CH$_2$— | phenyl | H | Cl | H |
| 1-25 | — | 1-methyl-1H-pyrazol-4-yl | H | Cl | H |
| 1-26 | —CH$_2$— | 2-methoxypyridin-5-yl | H | Cl | H |
| 1-27 | —CH$_2$— | 2-trifluoromethyl pyridin-5-yl | H | Cl | H |
| 1-28 | —CH$_2$— | 2-fluorophenyl | —CH$_3$ | H | H |
| 1-29 | —CH$_2$— | 2-methoxypyridin-5-yl | H | MeO— | H |
| 1-30 | —CH$_2$— | 2-methoxypyridin-5-yl | H | MeSO$_2$— | H |
| 1-31 | —CH$_2$— | 2-methoxypyridin-5-yl | H | MeS— | H |
| 1-32 | —CH$_2$— | 2-methoxypyridin-5-yl | H | MeS(=O)— | H |
| 1-33 | —CH$_2$— | 2-methoxypyridin-5-yl | H | F$_5$S— | H |
| 1-34 | —CH$_2$— | 2-methoxypyridin-5-yl | H | EtO— | H |
| 1-35 | —CH$_2$— | 2-methoxypyridin-5-yl | H | NH$_2$SO$_2$— | H |
| 1-36 | —CH$_2$— | 2-methoxypyridin-5-yl | H | Ph | H |
| 1-36 | —CH$_2$— | 2-methoxypyridin-5-yl | H | PhO— | H |
| 1-37 | —CH$_2$— | 2-methoxypyridin-5-yl | H | BnO— | H |
| 1-38 | —CH$_2$— | 2-methoxypyridin-5-yl | H | —CF$_3$ | H |
| 1-39 | —CH$_2$— | 2-methoxypyridin-5-yl | H | CF$_3$O— | H |
| 1-40 | —CH$_2$— | 2-methoxypyridin-5-yl | H | —NO$_2$ | H |
| 1-41 | —CH$_2$— | 2-methoxypyridin-5-yl | H | —NH$_2$ | H |
| 1-42 | —CH$_2$— | 2-methoxypyridin-5-yl | H | AcNH— | H |
| 1-43 | —CH$_2$— | 2-methoxypyridin-5-yl | H | HC≡C— | H |

TABLE 1-continued

| Compound number | $L^2$ | $(R^B)_n$—B | $R^1$ | $R^2$ | $R^3$ |
|---|---|---|---|---|---|
| 1-44 | —CH$_2$— | 2-methoxypyridin-5-yl | H | CN | H |
| 1-45 | —CH$_2$— | 4-trifluoromethoxyphenyl | H | Cl | H |
| 1-46 | —CH$_2$— | 2-trifluoromethyl-4-fluorophenyl | H | Cl | H |
| 1-47 | —CH$_2$— | 2-fluoro-4-difluoromethoxyphenyl | H | Cl | H |
| 1-48 | —CH$_2$— | 2-(2,2,2-trifluoroethyoxy)pyridin-5-yl | H | Cl | H |
| 1-49 | —CH$_2$— | 4-fluorophenyl | H | Cl | 7-F |
| 1-50 | —CH$_2$— | 2-methoxypyridin-5-yl | H | Cl | 7-F |
| 1-51 | —CH$_2$— | phenyl | H | Cl | 7-F |
| 1-52 | —CH$_2$— | pyridin-4-yl | H | Cl | 7-F |
| 1-52 | —CH$_2$— | 2-trifluoromethyl thiazol-5-yl | H | Cl | 7-F |
| 1-54 | —CH$_2$— | 2-chloropyridin-5-yl | H | Cl | 7-F |
| 1-55 | —CH$_2$— | 2-ethoxylthiazol-5-yl | H | Cl | 7-F |
| 1-56 | —CH$_2$— | 2-ethoxypyridin-5-yl | H | Cl | 7-F |
| 1-57 | —CH$_2$— | 4-fluorophenyl | H | MeO— | 7-F |
| 1-58 | —CH$_2$— | 2-methoxypyridin-5-yl | H | MeO— | 7-F |
| 1-59 | —CH$_2$— | phenyl | H | MeO— | 7-F |
| 1-60 | —CH$_2$— | pyridin-4-yl | H | MeO— | 7-F |
| 1-61 | —CH$_2$— | 2-trifluoromethyl thiazol-5-yl | H | MeO— | 7-F |
| 1-62 | —CH$_2$— | 2-chloropyridin-5-yl | H | MeO— | 7-F |
| 1-63 | —CH$_2$— | 2-ethoxylthiazol-5-yl | H | MeO— | 7-F |
| 1-64 | —CH$_2$— | 2-ethoxypyridin-5-yl | H | MeO— | 7-F |
| 1-65 | —CH$_2$— | 4-fluorophenyl | H | EtO— | H |
| 1-66 | —CH$_2$— | 4-fluorophenyl | H | —NO$_2$ | H |
| 1-67 | —CH$_2$— | 4-fluorophenyl | H | MeSO$_2$— | H |
| 1-68 | —CH$_2$— | 4-fluorophenyl | H | F$_5$S— | H |
| 1-69 | —CH$_2$— | 4-fluorophenyl | H | AcNH— | H |
| 1-70 | —CH$_2$— | 4-fluorophenyl | H | PhNH— | H |
| 1-71 | —CH$_2$— | 2-methoxypyridin-5-yl | F | Cl | H |
| 1-72 | —CH$_2$— | 2-methoxypyridin-5-yl | Cl | Cl | H |
| 1-73 | —CH$_2$— | 2-methoxypyridin-5-yl | —CN | Cl | H |
| 1-74 | —CH$_2$— | 2-methoxypyridin-5-yl | —CHO | Cl | H |
| 1-75 | —CH$_2$— | 4-fluorophenyl | H | OCF$_3$ | H |
| 1-76 | —CH$_2$— | 2-methoxypyridin-5-yl | H | OCF$_3$ | H |
| 1-77 | —CH$_2$— | 2-trifluoromethyl thiazol-5-yl | H | OCF$_3$ | H |

TABLE 2

| Compound number | L² | (R^B)n—B (ring) | R² | Y | (R^A)m—A—L¹—Q group |
|---|---|---|---|---|---|
| 2-1 | —CH₂— | 4-fluorophenyl | Cl | H | 4-carboxyphenyl (–C₆H₄–CO₂H) |
| 2-2 | —CH₂— | 4-fluorobenzyl | Cl | CN | 5-(pyridin-2-yl)-CO₂H (pyridine-2-carboxylic acid, linked at 5) |
| 2-3 | —CH₂— | 2-methoxy pyridin-5-yl | Cl | CN | 5-(pyridin-2-yl)-CO₂H |
| 2-4 | —CH₂— | phenyl | Cl | CN | 3-carboxyphenyl |
| 2-5 | —CH₂— | 4-fluorophenyl | Cl | H | 4-(C(O)NHOH)phenyl |
| 2-6 | —CH₂— | 2-methoxy pyridin-5-yl | Cl | CN | 4-(CH₂CO₂H)phenyl |
| 2-7 | —CH₂— | 2-methoxy pyridin-5-yl | Cl | CN | 4-(1-carboxycyclopropyl)phenyl |
| 2-8 | —CH₂— | 2-methoxy pyridin-5-yl | Cl | CN | 4-(2-carboxyprop-2-yl)phenyl |
| 2-9 | —CH₂— | 2-methoxy pyridin-5-yl | Cl | CN | 4-(1-carboxyethyl)phenyl |

TABLE 2-continued
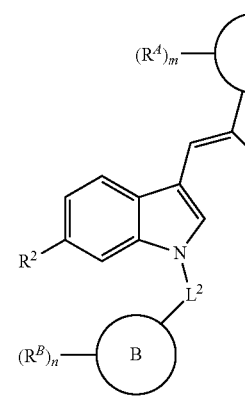
| Compound number | L² | 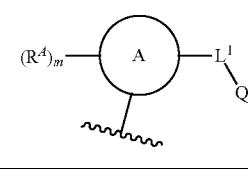 (Rᴮ)ₙ—B | R² | Y | 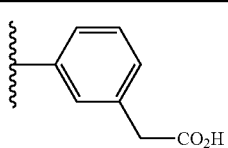 |
|---|---|---|---|---|---|
| 2-10 | —CH₂— | 2-methoxy pyridin-5-yl | Cl | CN | 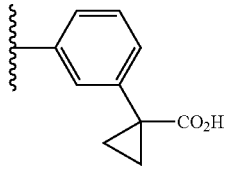 [SMILES: *c1cccc(C2(C(=O)O)CC2)c1] |
| 2-11 | —CH₂— | 2-methoxy pyridin-5-yl | Cl | CN | 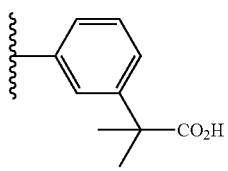 |
| 2-12 | —CH₂— | 2-methoxy pyridin-5-yl | Cl | CN | 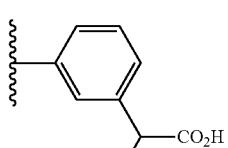 |
| 2-13 | —CH₂— | 2-methoxy pyridin-5-yl | Cl | CN | 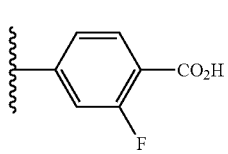 |
| 2-14 | —CH₂— | 2-methoxy pyridin-5-yl | Cl | CN | 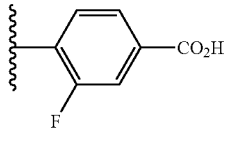 [SMILES: *c1ccc(C(=O)O)cc1F] |
| 2-15 | —CH₂— | 2-methoxy pyridin-5-yl | Cl | CN |  |

TABLE 2-continued

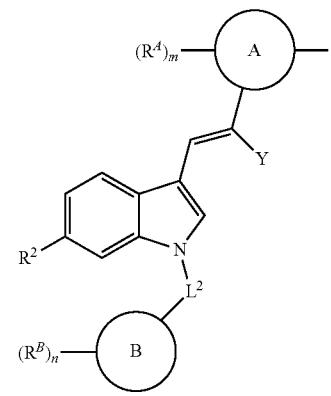

| Compound number | L² | (R^B)_n—B | R² | Y | (R^A)_m—A—L¹—Q |
|---|---|---|---|---|---|
| 2-16 | —CH₂— | 2-methoxy pyridin-5-yl | Cl | CN | 4-C(O)NHS(O)₂CH₃-phenyl |
| 2-17 | —CH₂— | 2-methoxy pyridin-5-yl | —OMe | CN | 5-(2-CO₂H-pyridyl) |
| 2-18 | —CH₂— | 4-fluorophenyl | —OMe | CN | 5-(2-CO₂H-pyridyl) |
| 2-19 | —CH₂— | 2-methoxy pyridin-5-yl | —NO₂ | CN | 5-(2-CO₂H-pyridyl) |
| 2-20 | —CH₂— | 2-methoxy pyridin-5-yl | CN | CN | 5-(2-CO₂H-pyridyl) |
| 2-21 | —CH₂— | 2-methoxy pyridin-5-yl | Cl | CN | 5-(2-CO₂H-pyrimidyl) |
| 2-22 | —CH₂— | 2-methoxy pyridin-5-yl | Cl | CN | 4-(2-CO₂H-thiazolyl) |
| 2-23 | —CH₂— | 2-methoxy pyridin-5-yl | Cl | CN | 5-(2-CO₂H-thiazolyl) |
| 2-24 | —CH₂— | 2-methoxy pyridin-5-yl | Cl | CN | 1-CO₂H-indanyl |

TABLE 2-continued
| Compound number | $L^2$ |  | $R^2$ | Y |  |
|---|---|---|---|---|---|
| 2-25 | —CH$_2$— | 4-fluorophenyl | Cl | CN |  |
| 2-26 | —CH2— | 4-fluorophenyl | Cl | CN | 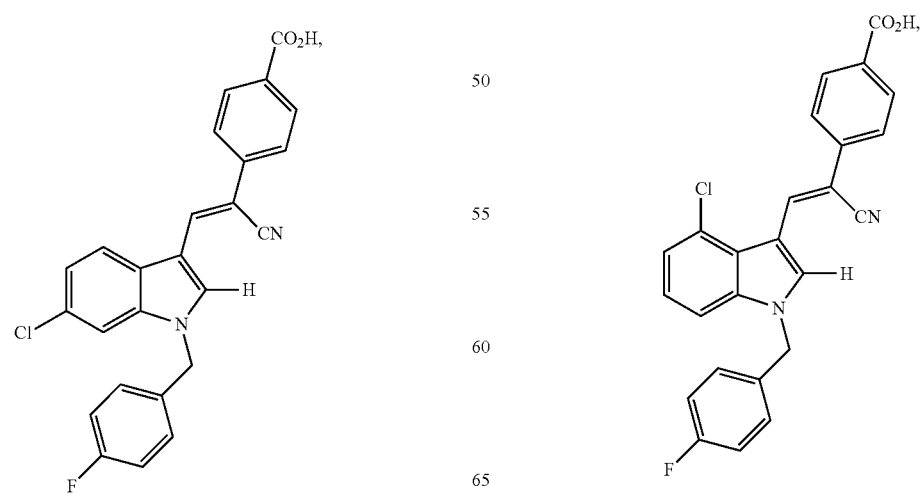 |
In some embodiments, the compound of Formula (I) has one of the following structures:

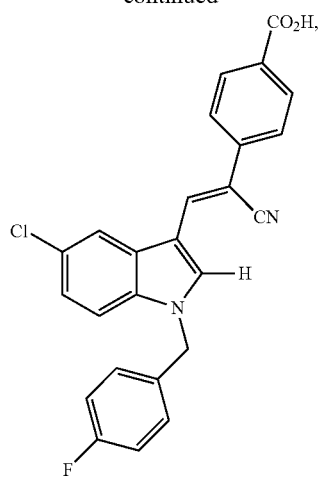
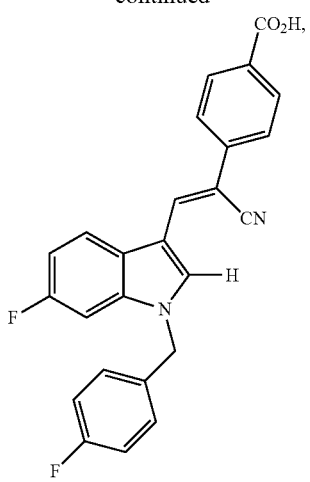
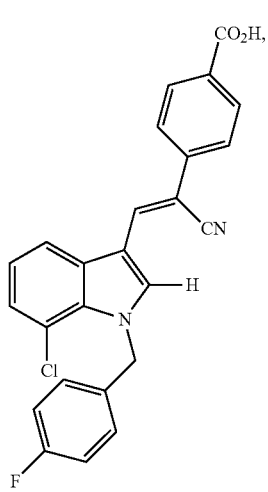
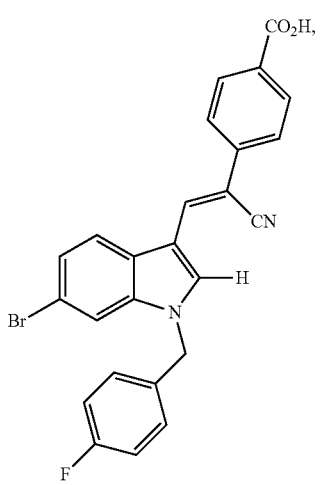
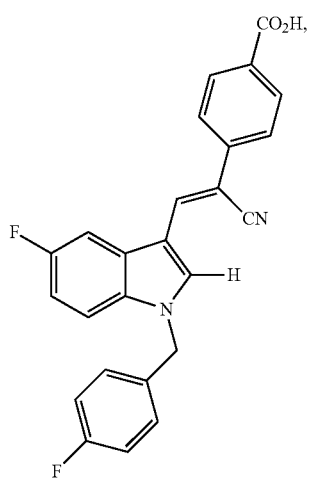
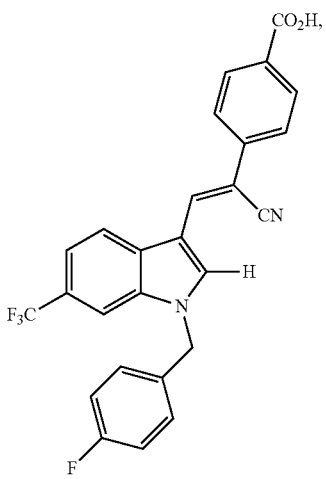

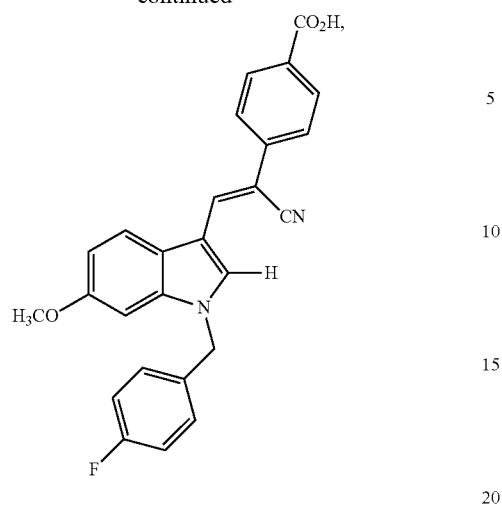
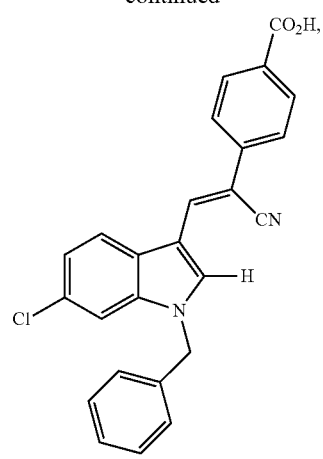
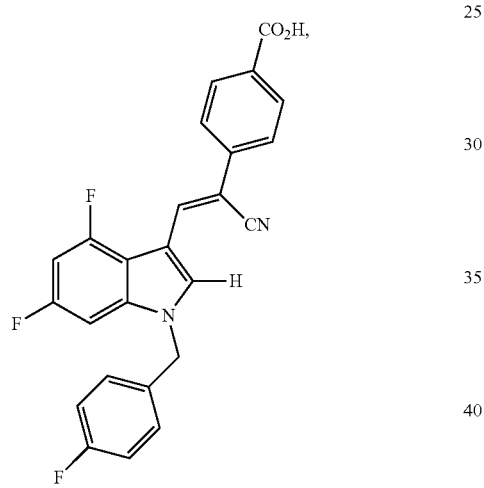
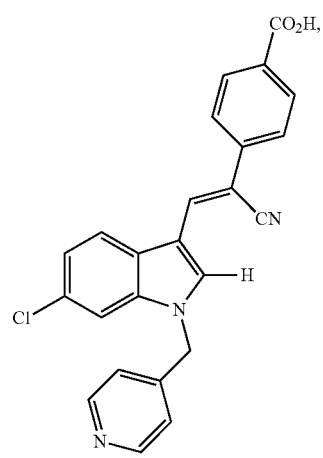
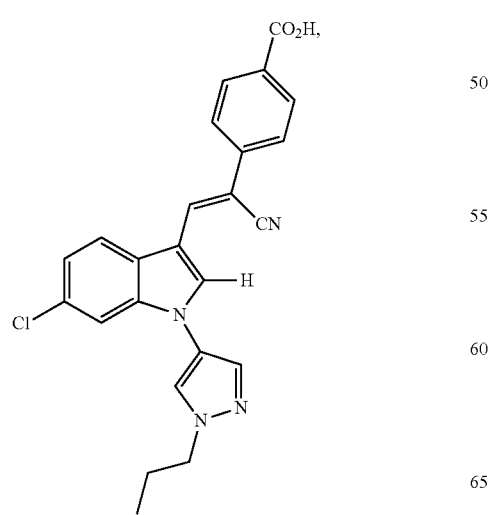
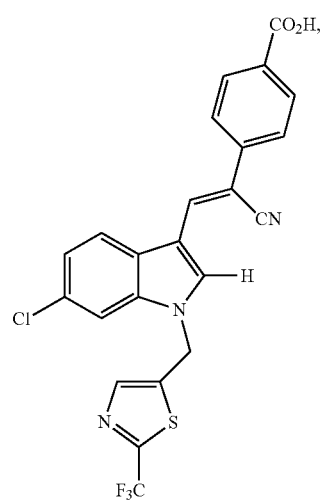

59
-continued
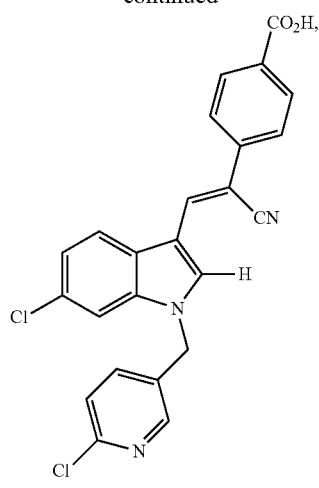
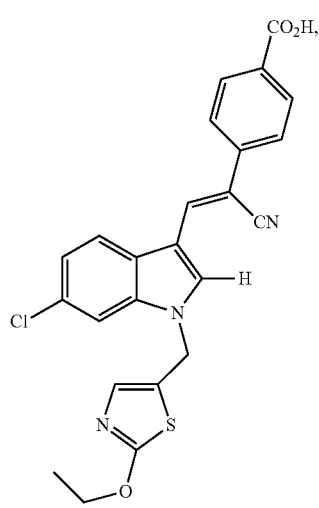
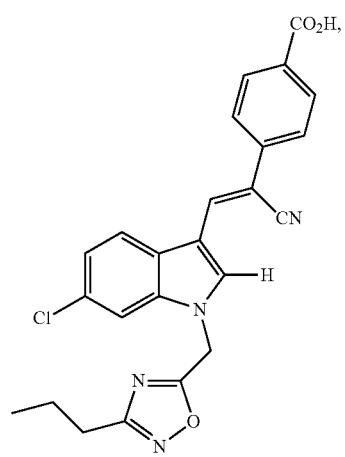
60
-continued
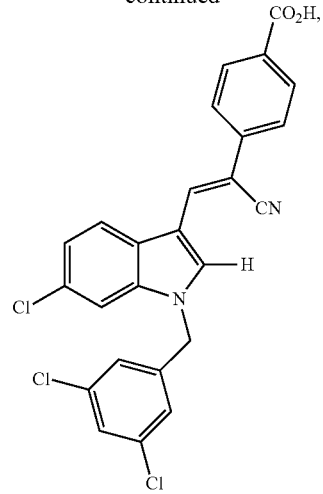
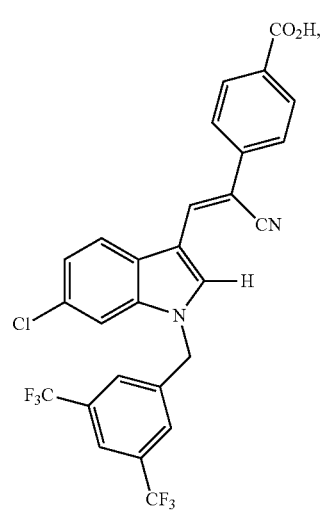
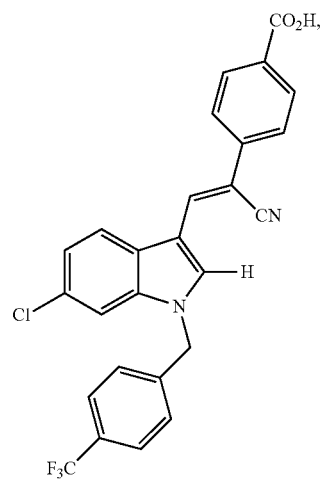

61
-continued
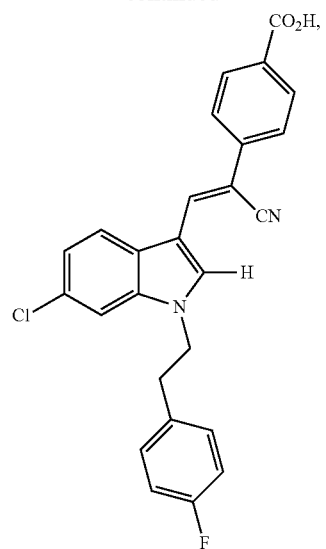
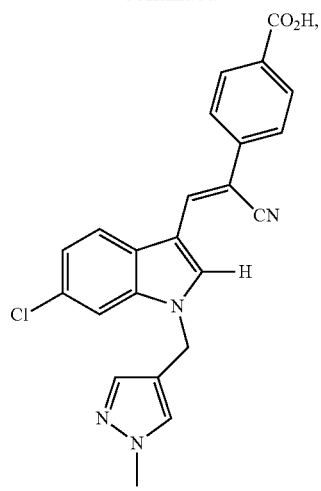
62
-continued
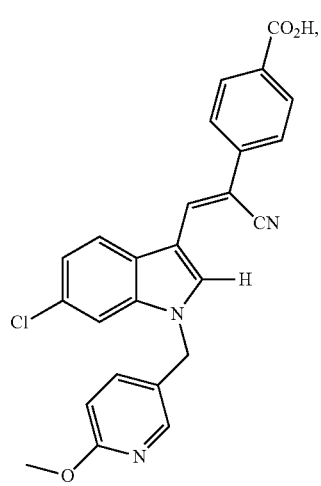
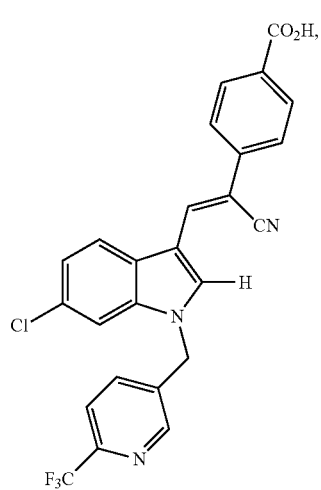

63
-continued
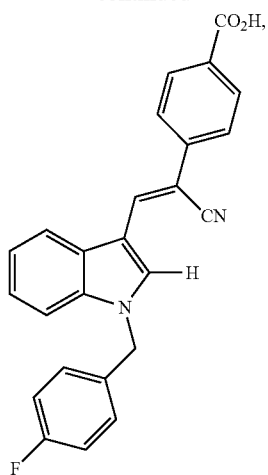
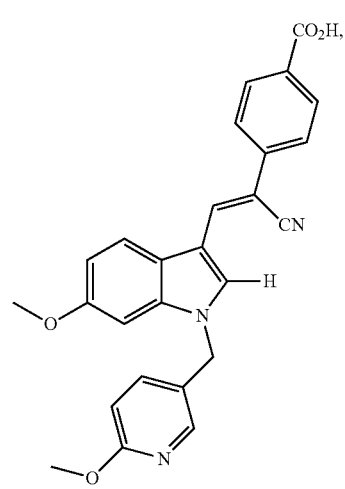
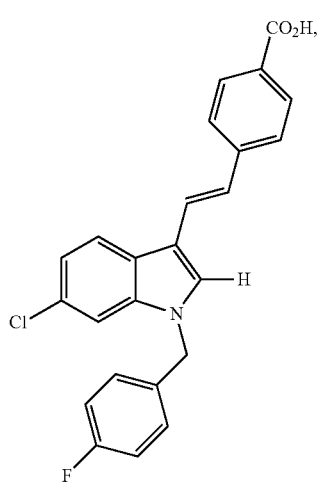
64
-continued
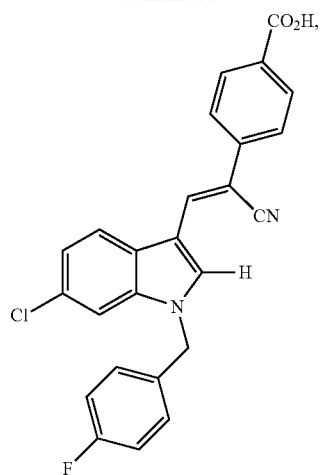
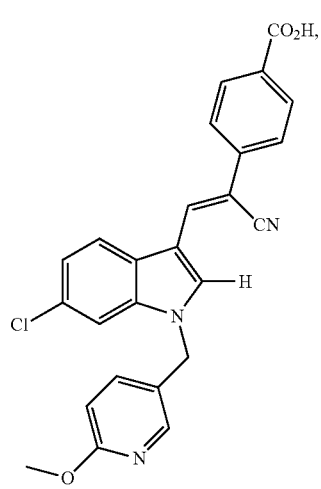
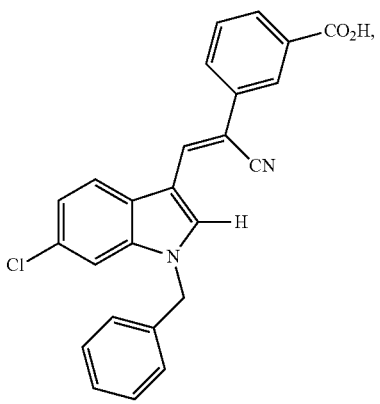

65
-continued
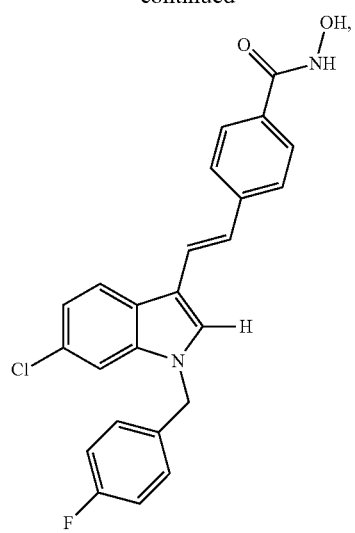
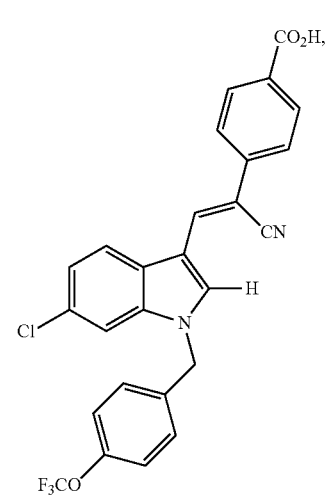
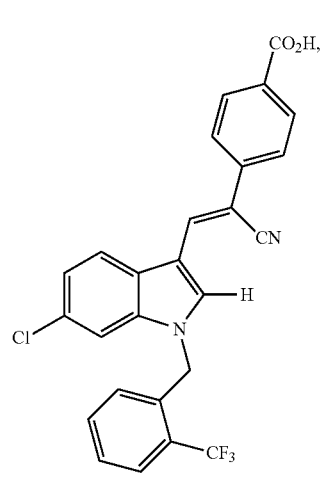
66
-continued
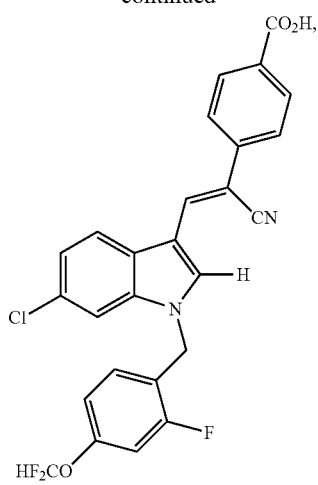
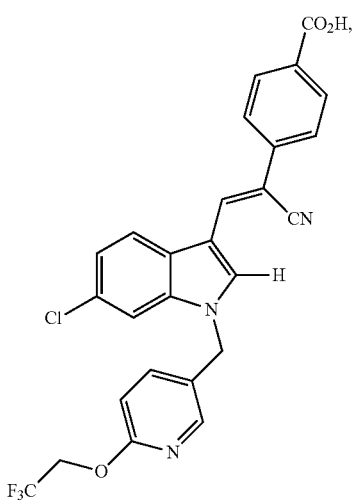
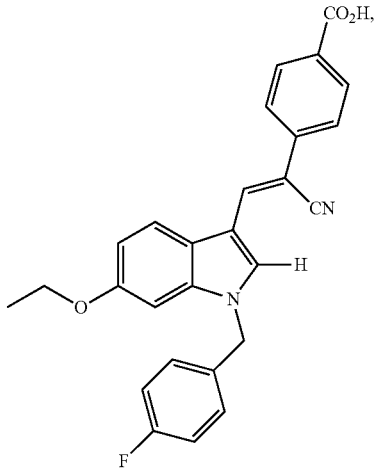

-continued

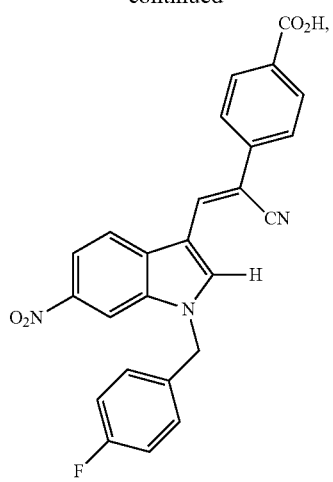

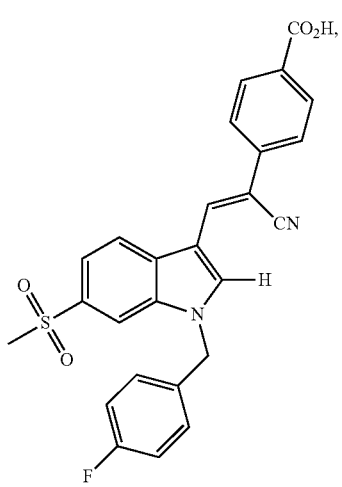

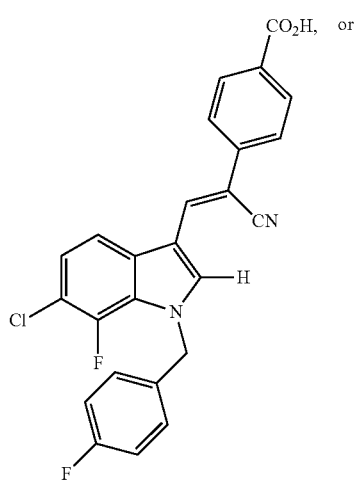

-continued

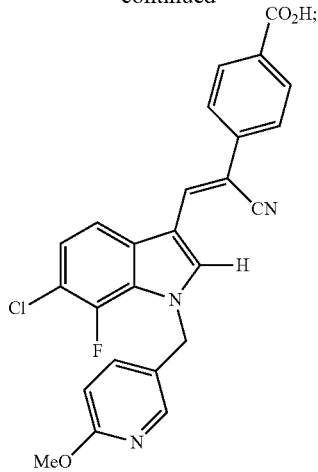

or a pharmaceutically acceptable salt, or solvate thereof.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound of Formula (I), Formula (II), Formula (III), Formula (IV), Formula (V), Formula (VI), or Formula (VII) with an acid. In some embodiments, the compound of Formula (I), Formula (II), Formula (III), Formula (IV), Formula (V), Formula (VI), or Formula (VII) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I), Formula (II), Formula (III), Formula (IV), Formula (V), Formula (VI), or Formula (VII) is prepared as a chloride salt, sulfate salt, bromide salt, mesylate salt, maleate salt, citrate salt or phosphate salt. In some embodiments, a compound of Formula (I), Formula (II), Formula (III), Formula (IV), Formula (V), Formula (VI), or Formula (VII) is prepared as a hydrochloride salt.

In some embodiments, pharmaceutically acceptable salts are obtained by reacting a compound of Formula (I), Formula (II), Formula (III), Formula (IV), Formula (V), Formula (VI), or Formula (VII) with a base. In some embodiments, the compound of Formula (I), Formula (II), Formula (III), Formula (IV), Formula (V), Formula (VI), or Formula (VII) is acidic and is reacted with a base. In such situations, an acidic proton of the compound of Formula (I), Formula (II), Formula (III), Formula (IV), Formula (V), Formula (VI), or Formula (VII) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^3H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Indoles are readily prepared by chemical synthesis using standard methodologies as described in the review "Practical methodologies for the synthesis of indoles" Humphrey and Kuethe, *Chem. Rev.*, 2006, 106, 2875-2911. Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Indole containing compounds of general structure I-7 may be prepared in a variety of ways. In some embodiments, indoles of general structure I-7 are prepared as outlined in Scheme I.

Scheme I

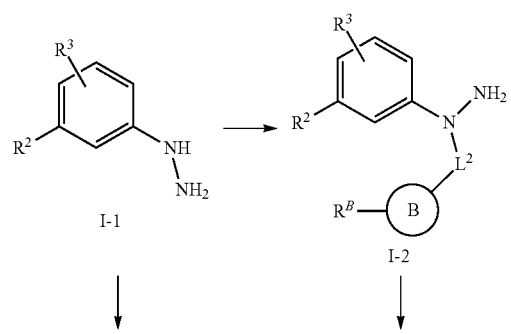

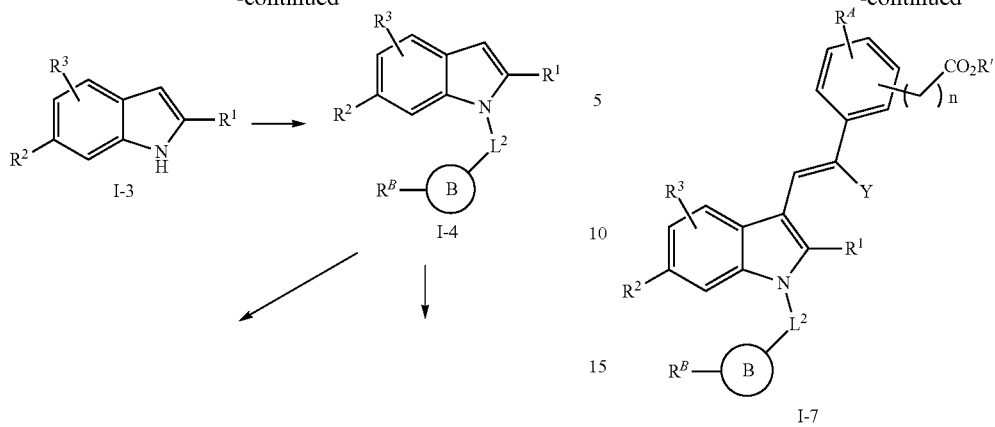

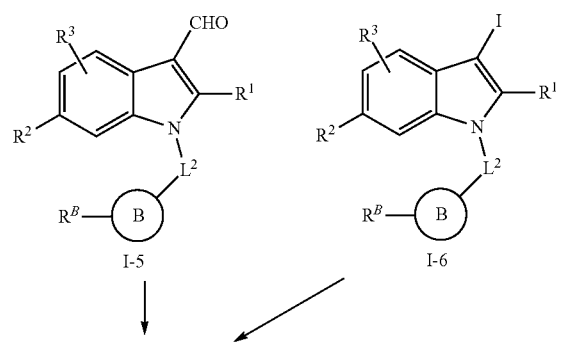

In some embodiments, as shown in Scheme I, a hydrazine of general structure I-1 is N-alkylated using standard conditions to afford the hydrazine I-2. Upon reaction with acetone, a Fisher-indole condensation then affords the indole I-4. Reversing the order of reactions (Fisher-indolization to yield I-3 then N-alkylation) provides an alternate way to synthesize I-4. In some embodiments, functionalization at C-3 of the indole I-4 is carried out to generate, for example, the 3-formyl derivative I-5 (using $POCl_3$ in DMF) or the 3-iodo derivative I-6 (using NIS in THF). In some embodiments, the aldehyde of I-5 is converted into the alkene containing compound 1-7 using, for example, an aldol reaction or a Wittig reaction. In some embodiments, the ester can then be hydrolyzed to the corresponding acid 1-7 (R'=H). In some other embodiments, alkene containing compounds such as I-7 are prepared from the iodo compound I-6 by, for example, metal-catalyzed cross coupling reaction using the appropriately substituted alkene or cross-coupling with the appropriate alkyne followed by reduction to the alkene. In some embodiments, hydrazines of general structure I-1 (or I-2) are reacted with an appropriate ketone to generate indoles of structure I-7 directly by utilizing the Fisher-indole reaction.

In some embodiments, 1H-indole-3-carbaldehydes are prepared as outlined in Scheme II.

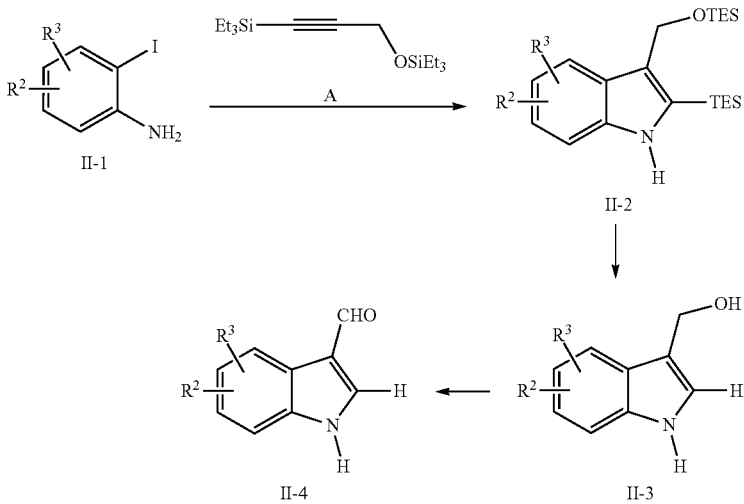

As shown in Scheme II, the Larock indole synthesis can be adapted to yield indoles II-4 containing both 2-H and 3-formyl substituents. Starting with the 2-iodo aniline II-1 a palladium catalyzed reaction using the bis-TES-propargyl alcohol A then forms the indole II-2. Removal of the silicon protecting groups then affords II-3 and oxidation results in the formation of II-4.

In some embodiments, indoles are prepared as outlined in Scheme III.

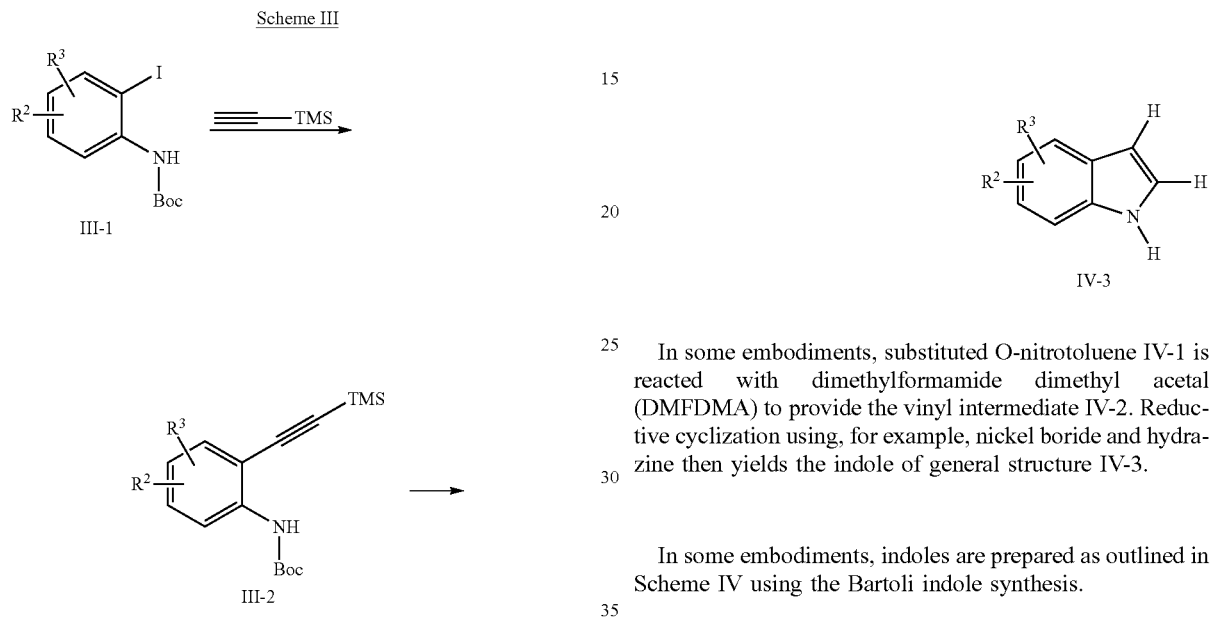

As shown in Scheme III, in some embodiments Boc-protected 2-iodoanilines (III-1) are treated with TMS-acetylene using Sonogashira cross-coupling conditions to generate the alkyne III-2 which, upon treatment with base then cyclizes to give indoles of general structure III-3.

In some embodiments, indoles are prepared as outlined in Scheme IV using the Leimgruber-Batcho indole synthesis.

Scheme IV

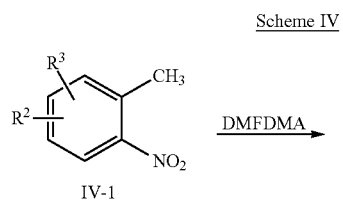

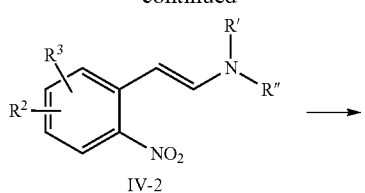

In some embodiments, substituted O-nitrotoluene IV-1 is reacted with dimethylformamide dimethyl acetal (DMFDMA) to provide the vinyl intermediate IV-2. Reductive cyclization using, for example, nickel boride and hydrazine then yields the indole of general structure IV-3.

In some embodiments, indoles are prepared as outlined in Scheme IV using the Bartoli indole synthesis.

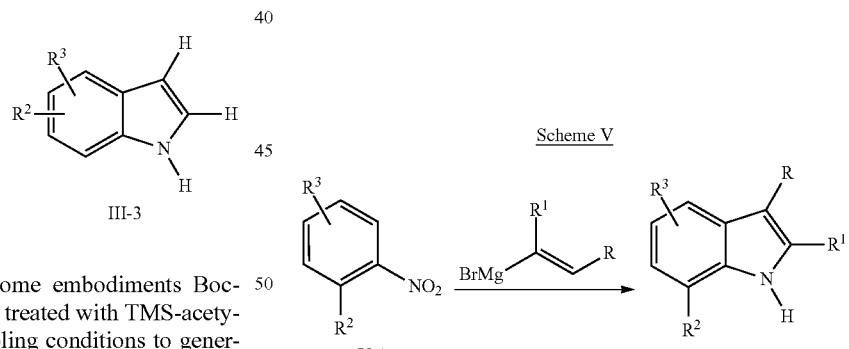

The Bartoli indole synthesis is shown in Scheme V and requires an ortho-substituted nitrobenzene (V-1). Treatment of V-1 with a vinyl magnesium Grignard reagent results in an indole of general structure V-2.

N—H Indoles of general structure VI-1 may be further modified as shown in Scheme VI.

Scheme VI

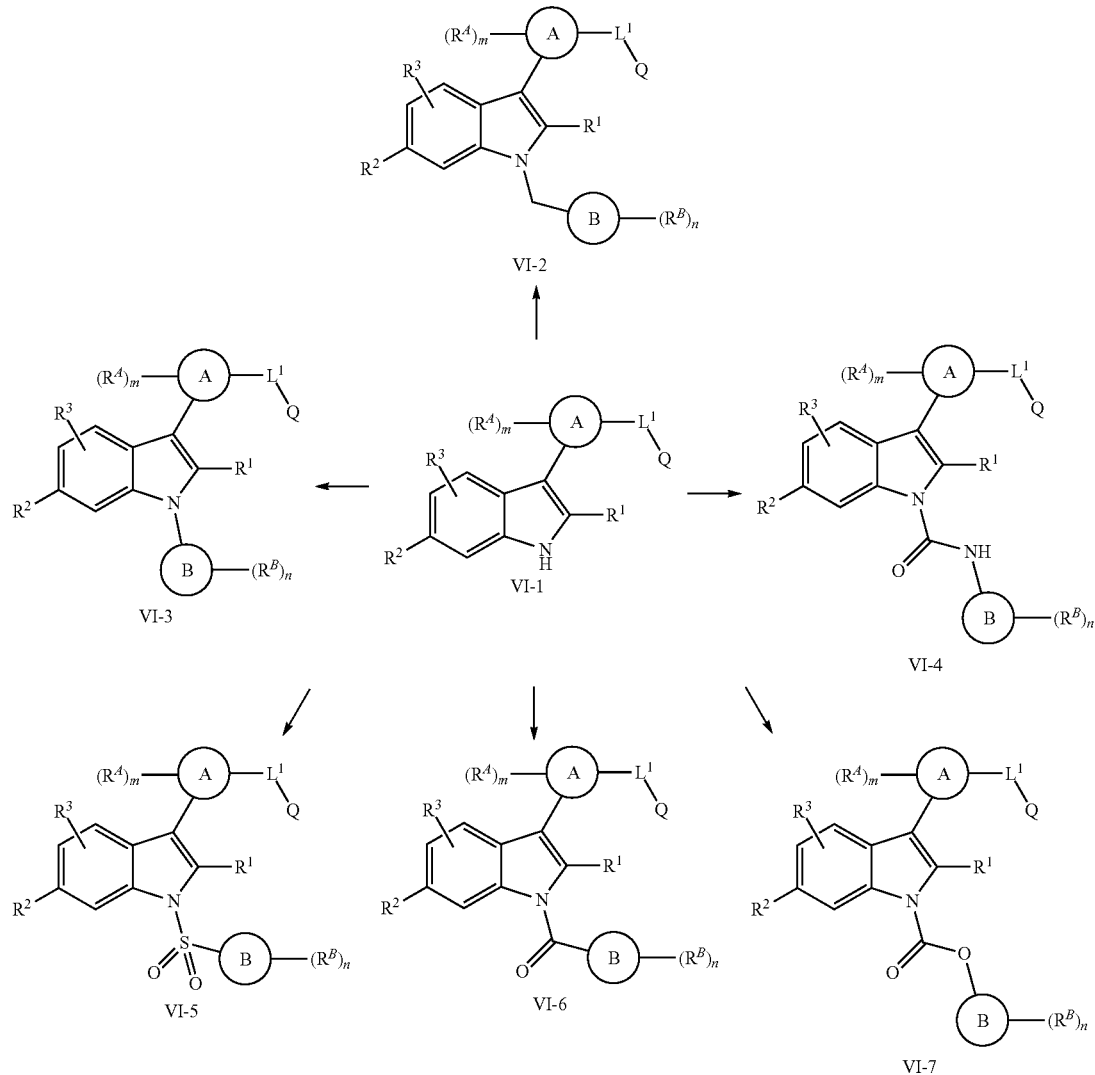

Treatment with a base such as NaH followed by alkylation with an electrophile (for example BrCH$_2$CONR'R" or BrCH$_2$CH$_2$CO$_2$tBu) can then form compounds of general structure VI-2. Subsequent chemical modifications can then be made to the indole N-substituent using standard chemical transformations. Direct arylation or heteroarylation may be achieved using Ullman-type conditions to generate VI-3. Deprotonation of VI-1 (e.g. by using NaH) followed by treatment with a variety of electrophiles (e.g. R$_3$SO$_2$Cl; R$_3$COCl, R$_3$OCOCl) can then afford a series of N-functionalized compounds of general structures VI-4 to VI-7.

In some embodiments, compounds described herein are synthesized as outlined in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$ alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$ alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, an alkylene is a $C_1$-$C_4$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=$CR_2$, wherein R refers to the remaining portions of the alkenyl group, which may be the same or different. In some embodiments, R is H or an alkyl. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. Non-limiting examples of an alkynyl group include —C≡CH, —C≡$CCH_3$—C≡$CCH_2CH_3$, —$CH_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1 (2H)-onyl, 3,4-dihydroquinolin-2(1H)-onyl, isoindoline-1,3-dithionyl, benzo[d] oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "carboxylic acid bioisostere" refers to a functional group or moiety that exhibits similar physical, biological and/or chemical properties as a carboxylic acid moiety. Examples of carboxylic acid bioisosteres include, but are not limited to,

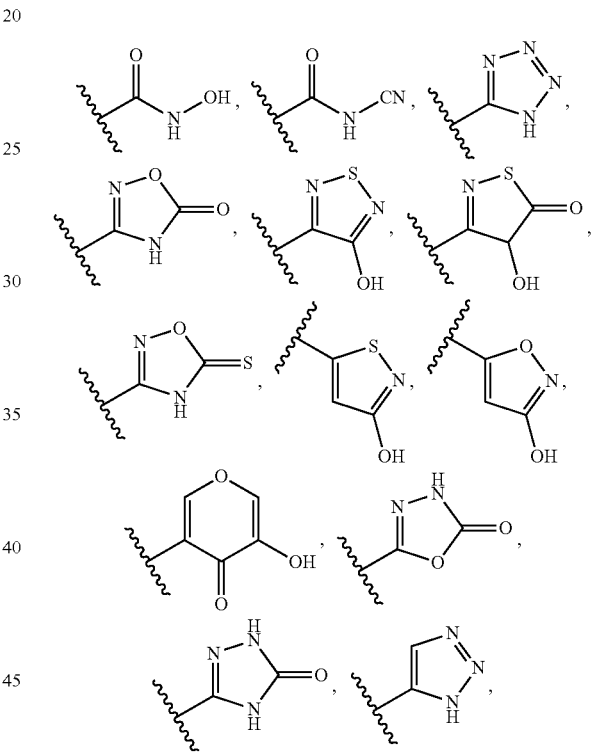

and the like.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), Formula (II), Formula (III), Formula (IV), Formula (V), Formula (VI), or Formula (VII), or a pharmaceutically acceptable salt thereof, and a co-agent, are both administered to a patient simultaneously in the form of a single entity or dosage. The term "non-fixed combination" means that the active ingredients, e.g. a compound of Formula (I), Formula (II), Formula (III), Formula (IV), Formula (V), Formula (VI), or Formula (VII), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds of Formula (I), Formula (II), Formula (III), Formula (IV), Formula (V), Formula (VI), or Formula (VII), or a pharmaceutically acceptable salt thereof, are used in the preparation of medicaments for the treatment of diseases or conditions in a mammal that would benefit from inhibition or reduction of autotaxin activity. Methods for treating any of the diseases or conditions described herein in a mammal in need of such treatment, involves administration of pharmaceutical compositions that include at least one compound of Formula (I), Formula (II), Formula (III), Formula (IV), Formula (V), Formula (VI), or Formula (VII) or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), Formula (II), Formula (III), Formula (IV), Formula (V), Formula (VI), or Formula (VII), or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound of Formula (I), Formula (II), Formula (III), Formula (IV), Formula (V), Formula (VI), or Formula (VII), or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound of Formula (I), Formula (II), Formula (III), Formula (IV), Formula (V), Formula (VI), or Formula (VII), or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound of Formula (I), Formula (II), Formula (III), Formula (IV), Formula (V), Formula (VI), or Formula (VII), or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound of Formula (I), Formula (II), Formula (III), Formula (IV), Formula (V), Formula (VI), or Formula (VII), or a pharmaceutically acceptable salt thereof, is co-administered with a second therapeutic agent, wherein the compound of Formula (I), Formula (II), Formula (III), Formula (IV), Formula (V), Formula (VI), or Formula (VII), or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient is simply be additive of the two therapeutic agents or the patient experiences a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), Formula (II), Formula (III), Formula (IV), Formula (V), Formula (VI), or Formula (VII), or a pharmaceutically acceptable salt thereof, is initiated prior to, during, or after treatment with a second agent described herein, and continues until any time during treatment with the second agent or after termination of treatment with the second agent. It also includes treatments in which a compound of Formula (I), Formula (II), Formula (III), Formula (IV), Formula (V), Formula (VI), or Formula (VII), or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds of Formula (I), Formula (II), Formula (III), Formula (IV), Formula (V), Formula (VI), or Formula (VII), or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

Exemplary Agent for Use in Combination Therapy

In some embodiments, a compound of Formula (I), Formula (II), Formula (III), Formula (IV), Formula (V), Formula (VI), or Formula (VII), or a pharmaceutically acceptable salt thereof, in combination with chemotherapy, hormone blocking therapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

Chemotherapy includes the use of anti-cancer agents.

In some embodiments, anti-cancer agents for use in combination with a compound of Formula (I), Formula (II), Formula (III), Formula (IV), Formula (V), Formula (VI), or Formula (VII), or a pharmaceutically acceptable salt thereof, include one or more of the following: abiraterone; abarclix; abraxane, adriamycin; actinomycin; acivicin; aclarubicin; acodazole hydrochloride; acronine; adozelesin; aldesleukin; alemtuzumab; allopurinol; alitretinoin; altretamine; ametantrone acetate; aminoglutethimide; aminolevulinic acid; amifostine; amsacrine; anastrozole; anthramycin; aprepitant; arsenic trioxide; asparaginase; asperlin; azacitidine; azetepa; azotomycin; batimastat; bendamustine hydrochloride; benzodepa; bevacizumab; bexarotene; bicalutamide; bisantrene hydrochloride; bisnafide dimesylate; bizelesin; bleomycin; bleomycin sulfate; bortezomib; brequinar sodium; bropirimine; busulfan; cactinomycin; calusterone; caracemide; carbetimer; carboplatin; carmustine; carubicin hydrochloride; carzelesin; capecitabine; cedefingol; cetuximab; chlorambucil; cirolemycin; cisplatin; cladribine; clofarabine; crisnatol mesylate; cyclophosphamide; cytarabine; dacarbazine; dasatinib; daunorubicin hydrochloride; dactinomycin; darbepoetin alfa; decitabine; degarelix; denileukin diftitox; dexormaplatin; dexrazoxane hydrochloride; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; eltrombopag olamine; enloplatin; enpromate; epipropidine; epirubicin hydrochloride; epoetin alfa; erbulozole; erlotinib hydrochloride; esorubicin hydrochloride; estramustine; estramustine phosphate sodium; etanidazole; etoposide; etoposide phosphate; etoprine; everolimus; exemestane; fadrozole hydrochloride; fazarabine; fenretinide; filgrastim; floxuridine; fludarabine phosphate; fluorouracil; flurocitabine; fosquidone; fostriecin sodium; fulvestrant; gefitinib; gemcitabine; gemcitabine hydrochloride; gemcitabine-cisplatin; gemtuzumab ozogamicin; goserelin acetate; histrelin acetate; hydroxyurea; idarubicin hydrochloride; ifosfamide; iimofosine; ibritumomab tiuxetan; idarubicin; ifosfamide; imatinib mesylate; imiquimod; interleukin II (including recombinant interleukin II, or rlL2), interferon alfa-2a; interferon alfa-2b; interferon alfa-n1; interferon alfa-n3; interferon beta-1a; interferon gamma-1b; iproplatin; irinotecan hydrochloride; ixabepilone; lanreotide acetate; lapatinib; lenalidomide; letrozole; leuprolide acetate; leucovorin calcium; leuprolide acetate; levamisole; liposomal cytarabine; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; methoxsalen; metoprine; meturedepa; mitindomide; mitocarcin; mitocromin; mitogillin; mitomalcin; mitomycin C; mitosper; mitotane; mitoxantrone hydrochloride; mycophenolic acid; nandrolone phenpropionate; nelarabine; nilotinib; nocodazoie; nofetumomab; nogalamycin; ofatumumab; oprelvekin; ormaplatin; oxaliplatin; oxisuran; paclitaxel; palifermin; palonosetron hydrochloride; pamidronate; pegfilgrastim; pemetrexed disodium; pentostatin; panitumumab; pazopanib hydrochloride; pemetrexed disodium; plerixafor; pralatrexate; pegaspargase; peliomycin; pentamustine; peplomycin sulfate; perfosfamide; pipobroman; piposulfan; piroxantrone hydrochloride; plicamycin; plomestane; pomalidomide, porfimer sodium; porfiromycin; prednimustine; procarbazine hydrochloride; puromycin; puromycin hydrochloride; pyrazofurin; quinacrine; raloxifene hydrochloride; rasburicase; recombinant HPV bivalent vaccine; recombinant HPV quadrivalent vaccine; riboprine; rogletimide; rituximab; romidepsin; romiplostim; safingol; safingol hydrochloride; sargramostim; semustine; simtrazene; sipuleucel-T; sorafenib; sparfosate sodium; sparsomycin; spirogermanium hydrochloride; spiromustine; spiroplatin; streptonigrin; streptozocin; sulofenur; sunitinib malate; talisomycin; tamoxifen citrate; tecogalan sodium; tegafur; teloxantrone hydrochloride; temozolomide; temoporfin; temsirolimus; teniposide; teroxirone; testolactone; thalidomide; thiamiprine; thioguanine; thiotepa; tiazofurin; tirapazamine; topotecan hydrochloride; toremifene; tositumomab and I$^{131}$ Iodine tositumomab; trastuzumab; trestolone acetate; tretinoin; triciribine phosphate; trimetrexate; trimetrexate glucuronate; triptorelin; tubulozole hydrochloride; uracil mustard; uredepa; valrubicin; vapreotide; verteporfin; vinblastine; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorinostat; vorozole; zeniplatin; zinostatin; zoledronic acid; and zorubicin hydrochloride.

Monoclonal antibodies include, but are not limited to, trastuzumab (Herceptin) and rituximab (Rituxan).

In some embodiments, at least one additional chemotherapeutic agent is selected from, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), Formula (II), Formula (III), Formula (IV), Formula (V), Formula (VI), or Formula (VII), or a pharmaceutically acceptable salt thereof, is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, carfilzomib, trastuzumab, BAY 11-7082, PKC412, or PD184352, paclitaxel, and analogs of paclitaxel. Compounds that have the basic taxane skeleton as a common structure feature, have also been shown to have the ability to arrest cells in the G2-M phases due to stabilized microtubules and are optionally useful for treating cancer in combination with the compounds described herein.

Further examples of anti-cancer agents for use in combination with a compound of Formula (I), Formula (II), Formula (III), Formula (IV), Formula (V), Formula (VI), or Formula (VII), or a pharmaceutically acceptable salt thereof, include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; activin inhibitors, PKM2 inhibitors, c-fms inhibitors and histone deacetylase inhibitors. Further examples of anti-cancer agents for use in combination with a compound of Formula (I), Formula (II), Formula (III), Formula (IV), Formula (V), Formula (VI), or Formula (VII), or a pharmaceutically acceptable salt thereof, include aromatase inhibitors. Aromatase inhibitors include steroidal aromatase inhibitors and non-steroidal aromatase inhibitors. Steroidal aromatase inhibitors include, but are not limited to, exemestane. Non-steroidal aromatase inhibitors include, but are not limited to, anastrozole, and letrozole.

Yet other anticancer agents for use in combination with a compound of Formula (I), Formula (II), Formula (III), Formula (IV), Formula (V), Formula (VI), or Formula (VII), or a pharmaceutically acceptable salt thereof, include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with a compound of Formula (I), Formula (II), Formula (III), Formula (IV), Formula (V), Formula (VI), or Formula (VII), or a pharmaceutically acceptable salt thereof, include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with a compound of Formula (I), Formula (II), Formula (III), Formula (IV), Formula (V), Formula (VI), or Formula (VII), or a pharmaceutically acceptable salt thereof, include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.).

In some embodiments, a compound of Formula (I), Formula (II), Formula (III), Formula (IV), Formula (V), Formula (VI), or Formula (VII), or a pharmaceutically acceptable salt thereof, is used to treat cancer in combination with: an antiestrogen (e.g., tamoxifen), an antiandrogen (e.g., bicalutamide, flutamide), a gonadotropin releasing hormone analog (e.g., leuprolide).

Other agents that are optionally used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desactyleleutherobin, Isocleutherobin A, and Z-Eleutherobin), Caribacoside, Caribacolin, Halichondrin B, Diazonamide A, Taecalonolide A, Diozostatin, (−)-Phenylahistin, Myoseverin B, Resverastatin phosphate sodium.

In one aspect, a compound of Formula (I), Formula (II), Formula (III), Formula (IV), Formula (V), Formula (VI), or Formula (VII), or a pharmaceutically acceptable salt thereof, is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

In some embodiments, a compound of Formula (I), Formula (II), Formula (III), Formula (IV), Formula (V), Formula (VI), or Formula (VII), or a pharmaceutically acceptable salt thereof, is used in combination with anti-emetic agents to treat nausea or emesis, which result from the use of a compound of Formula (I), Formula (II), Formula (III), Formula (IV), Formula (V), Formula (VI), or Formula (VII), or a pharmaceutically acceptable salt thereof, anti-cancer agent(s) and/or radiation therapy.

Anti-emetic agents include, but are not limited to: neurokinin-1 receptor antagonists, 5HT3 receptor antagonists (such as ondansetron, granisetron, tropisetron, palonosetron, and zatisetron), $GABA_B$ receptor agonists (such as baclofen), corticosteroids (such as dexamethasone, prednisone, prednisolone, or others), dopamine antagonists (such as, but not limited to, domperidone, droperidol, haloperidol, chlorpromazine, promethazine, prochlorperazine, metoclopramide), antihistamines (H1 histamine receptor antagonists, such as but not limited to, cyclizine, diphenhydramine, dimenhydrinate, meclizine, promethazine, hydroxyzine), cannabinoids (such as but not limited to, cannabis, marinol, dronabinol), and others (such as, but not limited to, trimethobenzamide; ginger, emetrol, propofol).

In some embodiments, a compound of Formula (I), Formula (II), Formula (III), Formula (IV), Formula (V), Formula (VI), or Formula (VII), or a pharmaceutically acceptable salt thereof, is used in combination with an agent useful in the treatment of anemia. Such an anemia treatment agent is, for example, a continuous erythropoiesis receptor activator (such as epoetin-α).

In some embodiments, a compound of Formula (I), Formula (II), Formula (III), Formula (IV), Formula (V), Formula (VI), or Formula (VII), or a pharmaceutically acceptable salt thereof, is used in combination with an agent useful in the treatment of neutropenia. Examples of agents useful in the treatment of neutropenia include, but are not limited to, a hematopoietic growth factor which regulates the production and function of neutrophils such as a human granulocyte colony stimulating factor, (G-CSF). Examples of a G-CSF include filgrastim.

In one aspect, a compound of Formula (I), Formula (II), Formula (III), Formula (IV), Formula (V), Formula (VI), or Formula (VII), or a pharmaceutically acceptable salt thereof, is administered in combination with one or more immunosuppressants. Immunosuppressive therapy is clinically used to treat or prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control), and in the treatment of fibrotic conditions.

In some embodiments, a compound of Formula (I), Formula (II), Formula (III), Formula (IV), Formula (V), Formula (VI), or Formula (VII), or a pharmaceutically acceptable salt thereof, is administered with a corticosteroid. In some embodiments, a compound of Formula (I), Formula (II), Formula (III), Formula (IV), Formula (V), Formula (VI), or Formula (VII), or a pharmaceutically acceptable salt thereof, is administered with an a therapeutic agent selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG)), B-cell antagonists, rituximab, natalizumab.

Other therapeutic agents include, but are not limited to: cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam®, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), leflunomide, gold thioglucose, gold thiomalate, aurofin, sulfasalazine, hydroxychloroquinine, minocycline, rapamicin, mycophenolic acid, mycophenolate mofetil, FTY720, as well as those listed in U.S. Pat. No. 7,060,697.

In one embodiment, a compound of Formula (I), Formula (II), Formula (III), Formula (IV), Formula (V), Formula (VI), or Formula (VII), or a pharmaceutically acceptable salt thereof, is administered in combination with Cyclosporin A (CsA) or tacrolimus (FK506). In one embodiment, a compound of Formula (I), Formula (II), Formula (III), Formula (IV), Formula (V), Formula (VI), or Formula (VII), or a pharmaceutically acceptable salt thereof, is administered to a mammal in combination with an anti-inflammatory agent including, but not limited to, non-steroidal anti-inflammatory drugs (NSAIDs), phosphodiesterase-4 inhibitors. JNK kinase inhibitors and corticosteroids (glucocorticoids).

In some embodiments, a compound of Formula (I), Formula (II), Formula (III), Formula (IV), Formula (V), Formula (VI), or Formula (VII), or a pharmaceutically acceptable salt thereof, is administered with corticosteroids. Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound of Formula (I), Formula (II), Formula (III), Formula (IV), Formula (V), Formula (VI), or Formula (VII), or a pharmaceutically acceptable salt thereof, is administered to a mammal in combination with a non-steroidal anti-inflammatory drug (NSAID). NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, flurobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

In some embodiments, a compound of Formula (I), Formula (II), Formula (III), Formula (IV), Formula (V), Formula (VI), or Formula (VII), or a pharmaceutically acceptable salt thereof, is co-administered with an analgesic.

In some embodiments, a compound of Formula (I), Formula (II), Formula (III), Formula (IV), Formula (V), Formula (VI), or Formula (VII), or a pharmaceutically acceptable salt thereof, is used in combination with radiation therapy (or radiotherapy). Radiation therapy is the treatment of cancer and other diseases with ionizing radiation. Radiation therapy is optionally used to treat localized solid tumors, such as cancers of the skin, tongue, larynx, brain, breast, prostate, colon, liver, uterus and/or cervix. It is also optionally used to treat leukemia and lymphoma (cancers of the blood-forming cells and lymphatic system, respectively).

A technique for delivering radiation to cancer cells is to place radioactive implants directly in a tumor or body cavity. This is called internal radiotherapy (brachytherapy, interstitial irradiation, and intracavitary irradiation are types of internal radiotherapy.) Using internal radiotherapy, the radiation dose is concentrated in a small area, and the patient stays in the hospital for a few days. Internal radiotherapy is frequently used for cancers of the tongue, uterus, prostate, colon, and cervix.

The term "radiotherapy" or "ionizing radiation" include all forms of radiation, including but not limited to α, β, and γ radiation and ultraviolet light.

EXAMPLES

The following examples are provided for illustrative purposes only and not to limit the scope of the claims provided herein.

Example 1: (Z)-4-(2-(6-chloro-1-(4-fluorobenzyl)-1H-indol-3-yl)-1-cyanovinyl)benzoic Acid (Compound 1-4)

Step 1: 6-chloro-1H-indole-3-carbaldehyde

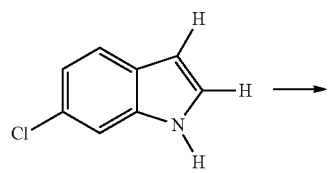

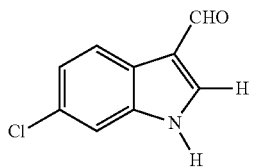

A solution of 6-Chloro-1H-indole (1.0 g, 6.59 mmol) and phosphorus oxychloride (8.56 mmol) in dimethylformamide (12 mL) was heated at 60° C. for 1 h. Water (5 mL) and concentrated sulfuric acid (3.95 mmol) were added to the reaction mixture then heated at 50° C. for 1 h. The mixture was concentrated and the residue was diluted with water (15 mL). The aqueous phase was extracted with ethyl acetate (3×25 mL). The organic extracts were combined and concentrated. Purification of the residue over silica gel, 0-75% ethyl acetate in hexanes, afforded the title compound (1.01 g, 85%) as a tan solid. LCMS [M+H] calculated: 179.6; observed: 179.9

Step 2: 6-chloro-1-(4-fluorobenzyl)-1H-indole-3-carbaldehyde

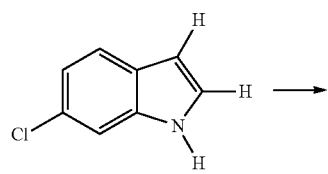

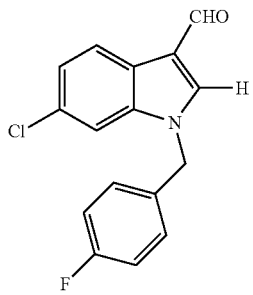

A mixture of product from Step 1 (75 mg, 0.417 mmol), 4-fluorobenzyl bromide (0.625 mmol), and potassium carbonate (1.25 mmol) in DMF (2 mL) was heated at 50° C. for 2 h. The reaction mixture was concentrated. Purification of the residue over silica gel, 0-60% ethyl acetate in hexanes, gave the title compound (104 mg, 86%) as an off white solid. LCMS [M+H] calculated: 287.7; observed: 287.8

$^{1}$HNMR (300 MHz, DMSO-$d_6$) δ 9.90 (s, 1H), 8.50 (s, 1H), 8.05-8.08 (d, 1H), 7.78 (s, 1H), 7.34-7.39 (m, 2H), 7.25-7.29 (m, 1H), 7.15-7.20 (t, 2H), 5.51 (s, 2H). LCMS [M+H] calculated: 287.7; observed: 287.8

Step 3: (Z)-ethyl 4-(2-(6-chloro-1-(4-fluorobenzyl)-1H-indol-3-yl)-1-cyanovinyl)benzoate

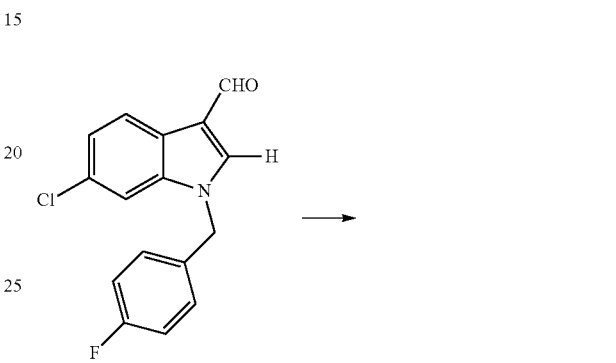

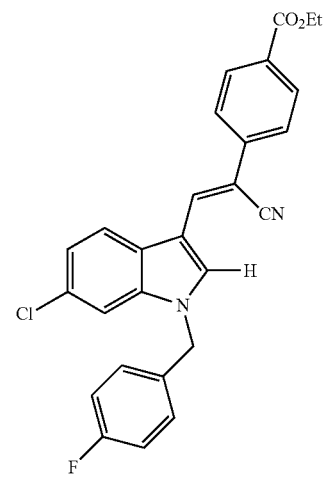

To a solution of product from Step 2 (200 mg, 0.695 mmol) in methanol (30 mL) were added methyl 4-(cyanomethyl)benzoate (0.834 mmol) and sodium hydroxide (1.39 mmol). The resulting mixture was stirred at 50° C. for 4 h. After the reaction mixture was cooled, it was diluted with THF (20 mL) then stirred at room temperature for 10 minutes. The solids were isolated by filtration to provide the title compound (202 mg, 65%) as a yellow solid. LCMS [M+H] calculated: 444.9; observed: 444.9.

Step 4: (Z)-4-(2-(6-chloro-1-(4-fluorobenzyl)-1H-indol-3-yl)-1-cyanovinyl)benzoic Acid

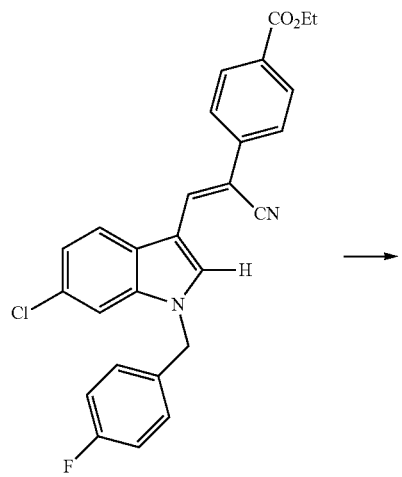

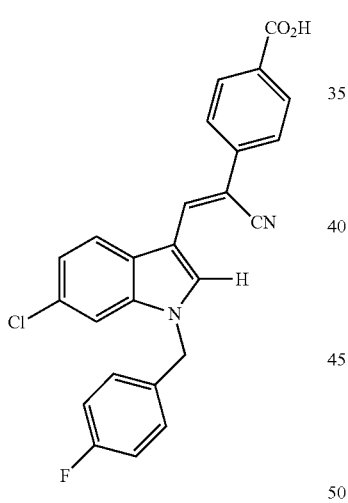

To a suspension of product from Step 3 (200 mg, 0.450 mmol) in THF/MeOH (3:1, 12 mL) was added aqueous 3N NaOH (0.9 mmol) and the resulting suspension was heated at 50° C. for 3 h. The reaction mixture was concentrated. The residue was diluted with water (5 mL) and acidified to pH 3 using 2N HCl. The aqueous phase was extracted with ethyl acetate (3×30 mL). The organic extracts were concentrated and the residue was purified over silica gel, 0-20% methanol in dichloromethane, to give Compound 1-4, (Z)-4-(2-(6-chloro-1-(4-fluorobenzyl)-1H-indol-3-yl)-1-cyanovinyl) benzoic acid (180 mg, 92%) as a yellow solid.

$^1$HNMR (300 MHz, DMSO-$d_6$) δ 13.04 (s broad, 1H), 8.56 (s, 1H), 8.38 (s, 1H), 8.16-8.18 (d, 1H), 7.89-8.01 (m, 4H), 7.77 (s, 1H), 7.31-7.37 (m, 2H), 7.15-7.26 (m, 3H), 5.61 (s, 2H). LCMS [M+H] calculated: 430.6; observed: 430.9

Example 2: 4-[(Z)-1-cyano-2-[1-[(4-fluorophenyl)methyl]indol-3-yl]vinyl]benzoic Acid (Compound 1-1)

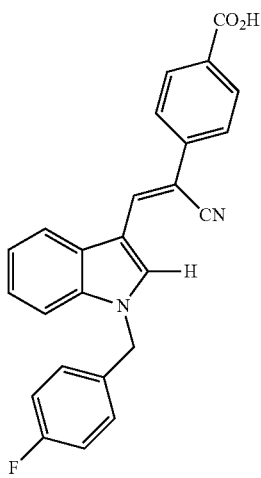 [SMILES: N#C/C(=C\c1cn(Cc2ccc(F)cc2)c2ccccc12)c1ccc(C(=O)O)cc1]

The title compound was prepared using the procedure for example 1 using 1-(4-fluorobenzyl)-1H-indole-3-carbaldehyde (ChemBridge Corporation) in step 3. LCMS [M+H] calculated: 430.8; observed: 431.

Example 3: 4-[(Z)-1-cyano-2-[4-chloro-1-[(4-fluorophenyl)methyl]indol-3-yl]vinyl]benzoic Acid (Compound 1-2)

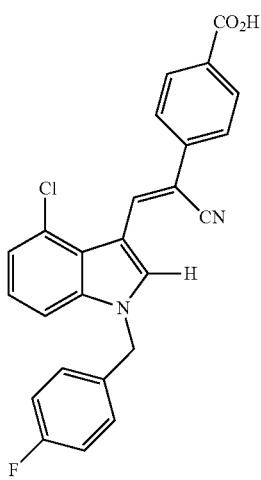 [SMILES: N#C/C(=C\c1cn(Cc2ccc(F)cc2)c2cccc(Cl)c12)c1ccc(C(=O)O)cc1]

The title compound was prepared using the procedure for example 1 using 4-chloro-1H-indole-3-carbaldehyde in step 2. LCMS [M+H] calculated: 430.1; observed: 431.

Example 4: 4-[(Z)-2-[5-chloro-1-[(4-fluorophenyl)methyl]indol-3-yl]-1-cyano-vinyl]benzoic Acid (Compound 1-3)

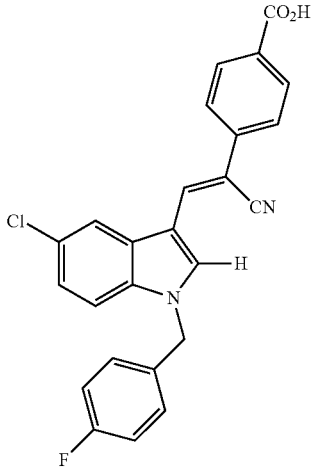 [SMILES: N#C/C(=C\c1cn(Cc2ccc(F)cc2)c2ccc(Cl)cc12)c1ccc(C(=O)O)cc1]

The title compound was prepared using the procedure for example 1 using 5-chloro-1H-indole 3-carbaldehyde in step 2.

Example 5: 4-[(Z)-2-[7-chloro-1-[(4-fluorophenyl)methyl]indol-3-yl]-1-cyano-vinyl]benzoic Acid (Compound 1-5)

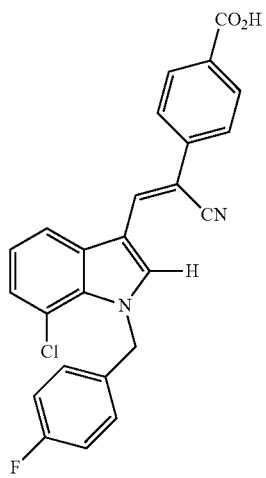 [SMILES: N#C/C(=C\c1cn(Cc2ccc(F)cc2)c2c(Cl)cccc12)c1ccc(C(=O)O)cc1]

The title compound was prepared using the procedure for example 1 using 7-chloro-1H-indole 3-carbaldehyde in step 2.

Example 6: 4-[(Z)-1-cyano-2-[5-fluoro-1-[(4-fluorophenyl)methyl]indol-3-yl]vinyl]benzoic Acid (Compound 1-6)

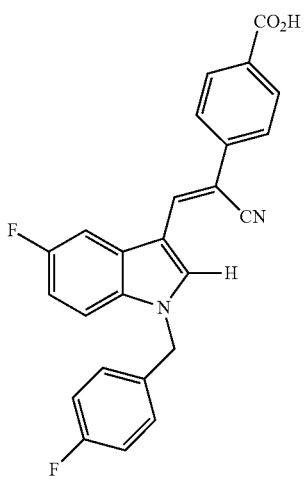 [SMILES: N#C/C(=C\c1cn(Cc2ccc(F)cc2)c2ccc(F)cc12)c1ccc(C(=O)O)cc1]

The title compound was prepared using the procedure for example 1 using 5-fluoro-1H-indole 3-carbaldehyde in step 2.

Example 7: 4-[(Z)-1-cyano-2-[6-fluoro-1-[(4-fluorophenyl)methyl]indol-3-yl]vinyl]benzoic Acid (Compound 1-7)

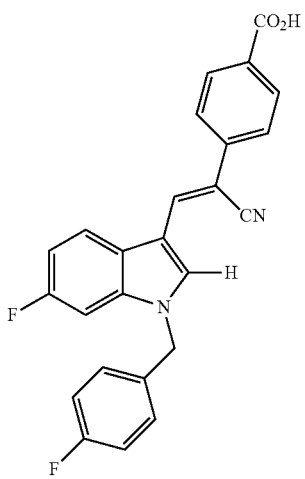 [SMILES: N#C/C(=C\c1cn(Cc2ccc(F)cc2)c2cc(F)ccc12)c1ccc(C(=O)O)cc1]

The title compound was prepared using the procedure for example 1 using 6-fluoro-1H-indole 3-carbaldehyde in step 2.

Example 8: 4-[(Z)-2-[6-bromo-1-[(4-fluorophenyl)methyl]indol-3-yl]-1-cyano-vinyl]benzoic Acid (Compound 1-8)

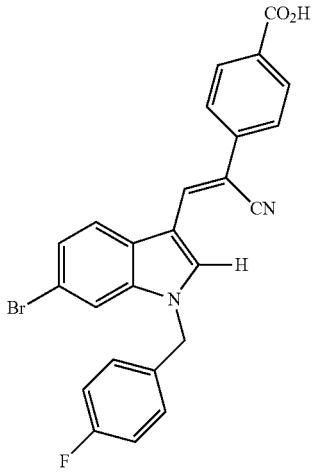

The title compound was prepared using the procedure for example 1 using 5-bromo-1H-indole 3-carbaldehyde in step 2.

Example 9: 4-[(Z)-1-cyano-2-[1-[(4-fluorophenyl)methyl]-6-(trifluoromethyl)indol-3-yl]vinyl]benzoic Acid (Compound 1-9)

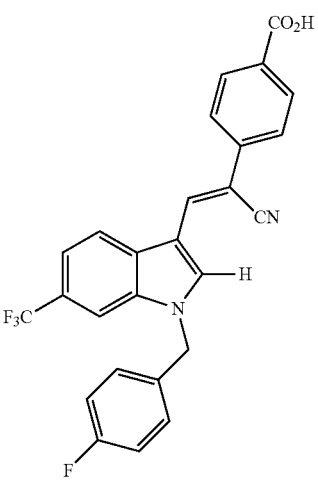 [SMILES: N#C/C(=C\c1cn(Cc2ccc(F)cc2)c2cc(C(F)(F)F)ccc12)c1ccc(C(=O)O)cc1]

The title compound was prepared using the procedure for example 1 using 6-(1,1,1-trifluoromethyl)-1H-indole 3-carbaldehyde in step 2.

Example 10: 4-[(Z)-1-cyano-2-[1-[(4-fluorophenyl)methyl]-6-methoxy-indol-3-yl]vinyl]benzoic Acid (Compound 1-10)

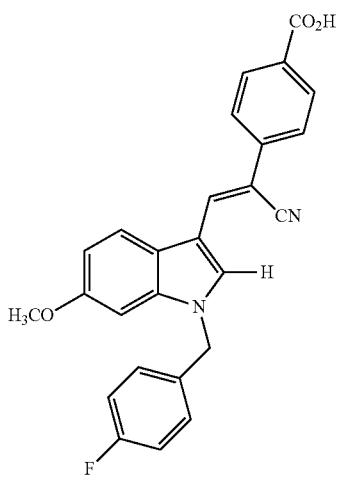

The title compound was prepared using the procedure for example 1 using 6-methoxy-1H-indole 3-carbaldehyde in step 2.

Example 11: 4-[(Z)-1-cyano-2-[4,6-difluoro-1-[(4-fluorophenyl)methyl]indol-3-yl]vinyl]benzoic Acid (Compound 1-11)

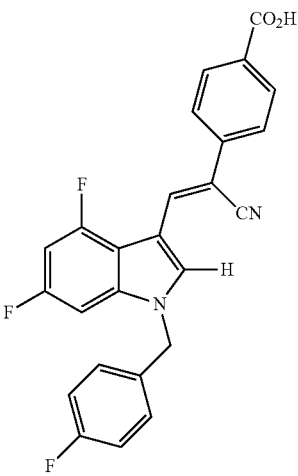 [SMILES: N#C/C(=C\c1cn(Cc2ccc(F)cc2)c2cc(F)cc(F)c12)c1ccc(C(=O)O)cc1]

The title compound was prepared using the procedure for example 1 using 4,6-difluoro-1H-indole 3-carbaldehyde in step 2.

Example 12: 4-[(Z)-2-[6-chloro-1-(1-propylpyrazol-4-yl)indol-3-yl]-1-cyano-vinyl]benzoic Acid (Compound 1-12)

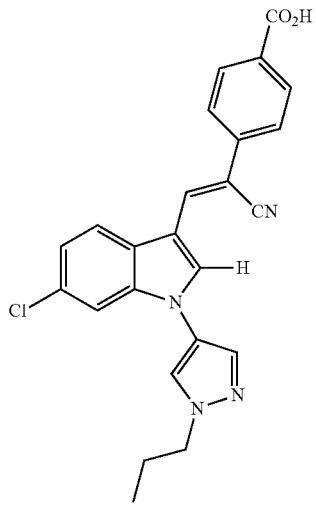 [SMILES: CCCn1cc(-n2cc(/C=C(\C#N)c3ccc(C(=O)O)cc3)c3ccc(Cl)cc32)cn1]

The title compound was prepared using the procedure for example 1 using 6-chloro-1-(1-propylpyrazol-4-yl)indole-3-carbaldehyde step 3.

Example 13: 4-[(Z)-2-(1-benzyl-6-chloro-indol-3-yl)-1-cyano-vinyl]benzoic Acid (Compound 1-13)

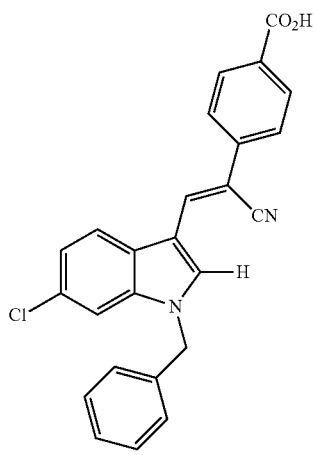 [SMILES: N#C/C(=C\c1cn(Cc2ccccc2)c2cc(Cl)ccc12)c1ccc(C(=O)O)cc1]

The title compound was prepared using the procedure for example 1 using benzyl bromide step 2.

Example 14: 4-[(Z)-2-[6-chloro-1-(4-pyridylmethyl)indol-3-yl]-1-cyano-vinyl]benzoic Acid (Compound 1-14)

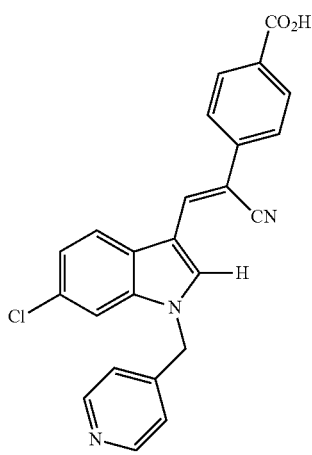 [SMILES: N#C/C(=C\c1cn(Cc2ccncc2)c2cc(Cl)ccc12)c1ccc(C(=O)O)cc1]

The title compound was prepared using the procedure for example 1 using 4-(chloromethyl)pyridine hydrochloride step 2.

Example 15: 4-[(Z)-2-[6-chloro-1-[[2-(trifluoromethyl)thiazol-5-yl]methyl]indol-3-yl]-1-cyano-vinyl]benzoic Acid (Compound 1-15)

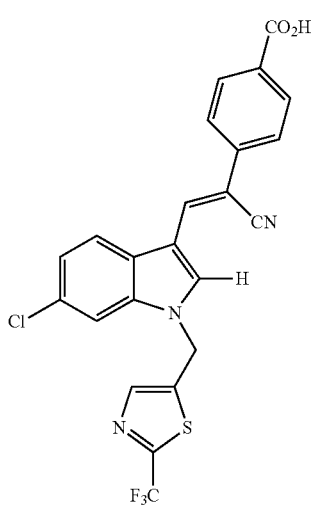 [SMILES: N#C/C(=C\c1cn(Cc2cnc(C(F)(F)F)s2)c2cc(Cl)ccc12)c1ccc(C(=O)O)cc1]

The title compound was prepared using the procedure for example 1 using 2-trifluoromethyl-5-(bromomethyl)thiazole step 2.

Example 16: 4-[(Z)-2-[6-chloro-1-[(6-chloro-3-pyridyl)methyl]indol-3-yl]-1-cyano-vinyl]benzoic Acid (Compound 1-16)

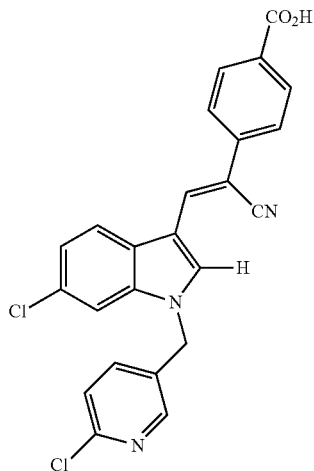 [SMILES: N#C/C(=C\c1cn(Cc2ccc(Cl)nc2)c2cc(Cl)ccc12)c1ccc(C(=O)O)cc1]

The title compound was prepared using the procedure for example 1 using 2-Chloro-5-(chloromethyl)pyridine Step 2.

Example 17: 4-[(Z)-2-[6-chloro-1-[(2-ethoxythiazol-5-yl)methyl]indol-3-yl]-1-cyano-vinyl]benzoic Acid (Compound 1-17)

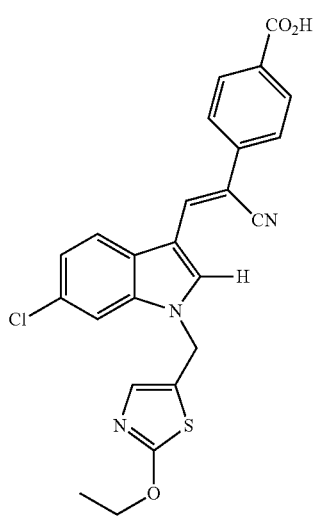 [SMILES: CCOc1ncc(Cn2cc(/C=C(\C#N)c3ccc(C(=O)O)cc3)c3ccc(Cl)cc32)s1]

The title compound was prepared using the procedure for example 1 using 2-Chloro-5-(chloromethyl)thiazole Step 2.

Example 18: 4-[(Z)-2-[6-chloro-1-[(3-propyl-1,2,4-oxadiazol-5-yl)methyl]indol-3-yl]-1-cyano-vinyl]benzoic Acid (Compound 1-18)

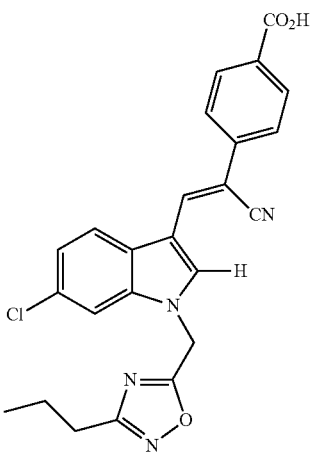 [SMILES: CCCc1noc(Cn2cc(/C=C(\C#N)c3ccc(C(=O)O)cc3)c3ccc(Cl)cc32)n1]

The title compound was prepared using the procedure for example 1 using 3-propyl-5-(chloromethyl)-1,2,4-oxadoazole Step 2.

Example 19: 4-[(Z)-2-[6-chloro-1-[(3,5-dichlorophenyl)methyl]indol-3-yl]-1-cyano-vinyl]benzoic Acid (Compound 1-19)

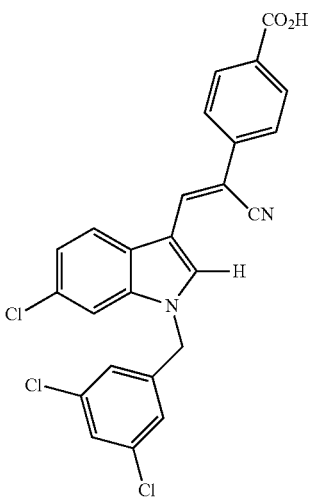 [SMILES: N#C/C(=C\c1cn(Cc2cc(Cl)cc(Cl)c2)c2cc(Cl)ccc12)c1ccc(C(=O)O)cc1]

The title compound was prepared using the procedure for example 1 using 3,5-dichlorobenzylchloride in step 2.

Example 20: 4-[(Z)-2-[1-[[3,5-bis(trifluoromethyl)phenyl]methyl]-6-chloro-indol-3-yl]-1-cyano-vinyl]benzoic Acid (Compound 1-20)

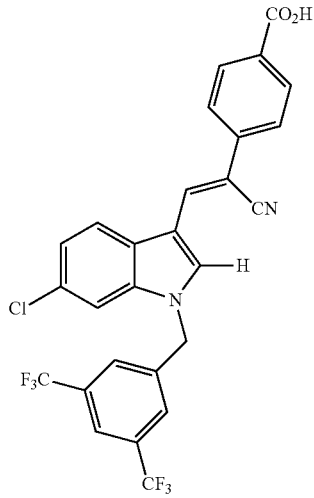 [SMILES: N#C/C(=C\c1cn(Cc2cc(C(F)(F)F)cc(C(F)(F)F)c2)c2cc(Cl)ccc12)c1ccc(C(=O)O)cc1]

The title compound was prepared using the procedure for example 1 using 3,5-Bis(trifluoromethyl)benzyl bromide in step 2.

Example 21: 4-[(Z)-2-[6-chloro-1-[[4-(trifluoromethyl)phenyl]methyl]indol-3-yl]-1-cyano-vinyl]benzoic Acid (Compound 1-21)

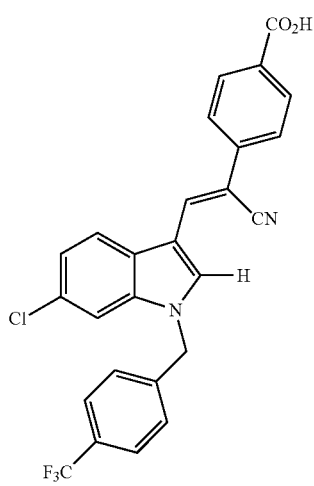 [SMILES: N#C/C(=C\c1cn(Cc2ccc(C(F)(F)F)cc2)c2cc(Cl)ccc12)c1ccc(C(=O)O)cc1]

The title compound was prepared using the procedure for example 1 using 4-(Trifluoromethyl)benzyl bromide in step 2.

Example 22: 4-[(Z)-2-[6-chloro-1-[2-(4-fluorophenyl)ethyl]indol-3-yl]-1-cyano-vinyl]benzoic Acid (Compound 1-22)

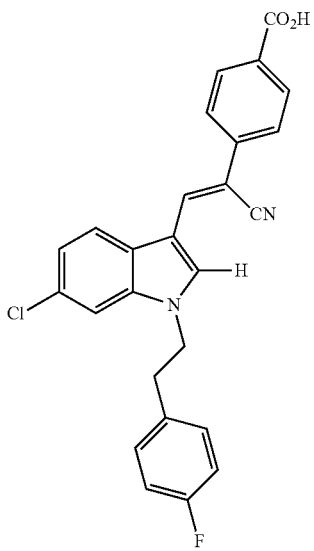 [SMILES: N#C/C(=C\c1cn(CCc2ccc(F)cc2)c2cc(Cl)ccc12)c1ccc(C(=O)O)cc1]

The title compound was prepared using the procedure for example 1 using 1-fluoro-4-(2-Bromoethyl)benzene in step 2.

Example 23: 4-[(Z)-2-[6-chloro-1-[3-(4-fluorophenyl)propyl]indol-3-yl]-1-cyano-vinyl]benzoic Acid (Compound 1-23)

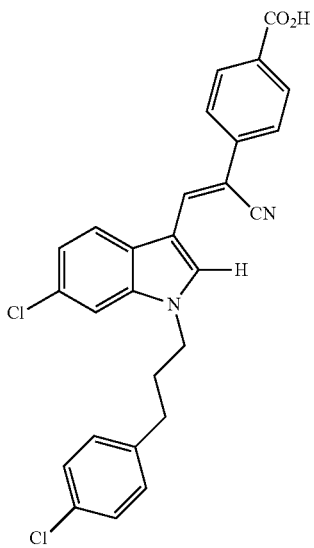 [SMILES: N#C/C(=C\c1cn(CCCc2ccc(Cl)cc2)c2cc(Cl)ccc12)c1ccc(C(=O)O)cc1]

The title compound was prepared using the procedure for example 1 using 1-(3-bromopropyl)-4-fluorobenzene in step 2.

Example 24: 4-[(Z)-2-[6-chloro-1-(3-phenylpropyl)indol-3-yl]-1-cyano-vinyl]benzoic Acid (Compound 1-24)

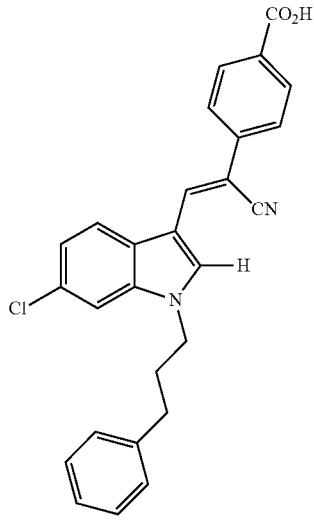 [SMILES: N#C/C(=C\c1cn(CCCc2ccccc2)c2cc(Cl)ccc12)c1ccc(C(=O)O)cc1]

The title compound was prepared using the procedure for example 1 using 3-phenylpropyl bromide in step 2.

Example 25: 4-[(Z)-2-[6-chloro-1-[(1-methylpyrazol-4-yl)methyl]indol-3-yl]-1-cyano-vinyl]benzoic Acid (Compound 1-25)

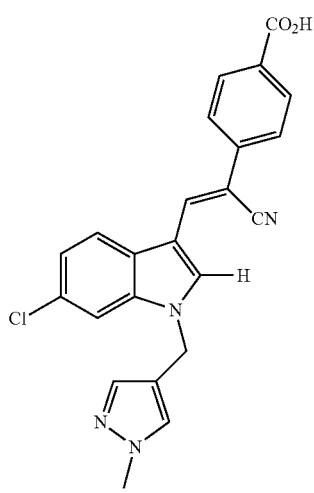 [SMILES: Cn1cc(Cn2cc(/C=C(\C#N)c3ccc(C(=O)O)cc3)c3ccc(Cl)cc32)cn1]

The title compound was prepared using the procedure for example 1 using 4-(Chloromethyl)-1-methyl-pyrazole hydrochloride in step 2.

Example 26: 4-[(Z)-2-[6-chloro-1-[(6-methoxy-3-pyridyl)methyl]indol-3-yl]-1-cyano-vinyl]benzoic Acid (Compound 1-26)

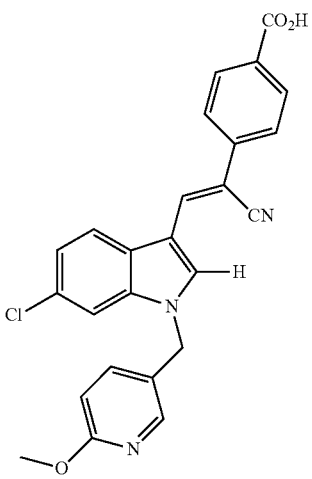 [SMILES: COc1ccc(Cn2cc(/C=C(\C#N)c3ccc(C(=O)O)cc3)c3ccc(Cl)cc32)cn1]

The title compound was prepared using the procedure for example 1 using 5-(chloromethyl)-2-methoxypyridine in step 2.

Example 27: 4-[(Z)-2-[6-chloro-1-[[6-(trifluoromethyl)-3-pyridyl]methyl]indol-3-yl]-1-cyano-vinyl]benzoic Acid (Compound 1-27)

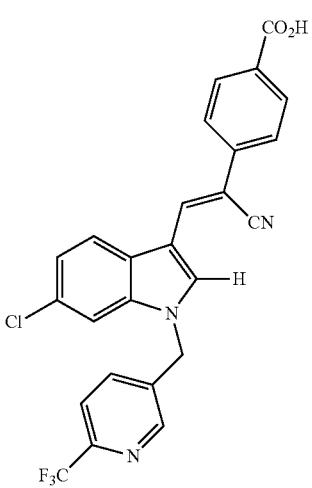

The title compound was prepared using the procedure for example 1 using 5-chloromethyl-2-(trifluoromethyl)pyridine in step 2.

Example 28: 4-[(Z)-1-cyano-2-[1-[(2-fluorophenyl)methyl]-2-methyl-indol-3-yl]vinyl]benzoic Acid (Compound 1-28)

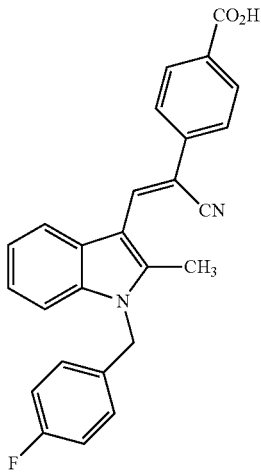 [SMILES: Cc1c(/C=C(\C#N)c2ccc(C(=O)O)cc2)c2ccccc2n1Cc1ccc(F)cc1]

The title compound was prepared using the procedure for example 1 using 1-(2-Fluorobenzyl)-2-methyl-3-carbaldehyde in step 2.

Example 29: 4-[(Z)-1-cyano-2-[6-methoxy-1-[(6-methoxy-3-pyridyl)methyl]indol-3-yl]vinyl]benzoic Acid (Compound 1-29)

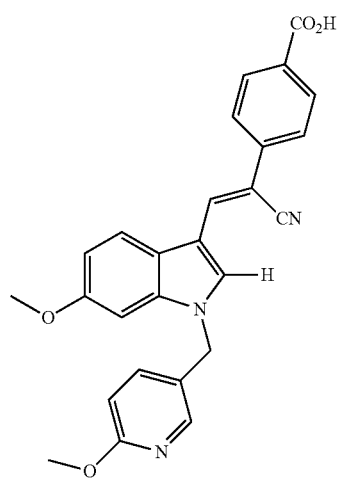 [SMILES: COc1ccc2c(/C=C(\C#N)c3ccc(C(=O)O)cc3)cn(Cc3ccc(OC)nc3)c2c1]

The title compound was prepared using the procedure for example 1 using 5-methoxy-1H-indole3-carbaldehyde in step 1 and 5-(chloromethyl)-2-methoxypyridine in step 2.

Example 30: 4-[(E)-2-(1-benzyl-6-chloro-indol-3-yl)vinyl]benzoic Acid (Compound 2-1)

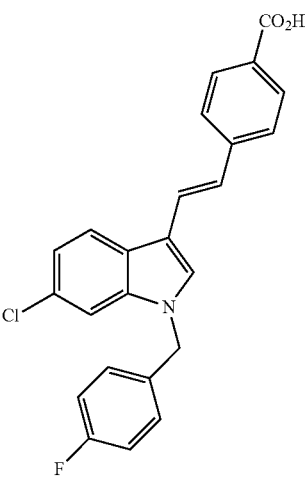 [SMILES: O=C(O)c1ccc(/C=C/c2cn(Cc3ccc(F)cc3)c3cc(Cl)ccc23)cc1]

The title compound was prepared using the procedure for example 1 using (4-methoxycarbonylbenzyl)triphenylphosphonium chloride and sodium hydride in step 3.

Example 31: 5-[(Z)-2-[6-chloro-1-[(4-fluorophenyl)methyl]indol-3-yl]-1-cyano-vinyl]pyridine-2-carboxylic Acid (Compound 2-2)

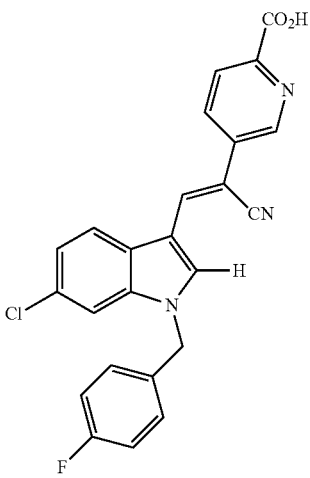 [SMILES: N#C/C(=C\c1cn(Cc2ccc(F)cc2)c2cc(Cl)ccc12)c1ccc(C(=O)O)nc1]

The title compound was prepared using the procedure for example 1 using methyl 5-(cyanomethyl)pyridine-2-carboxylate in step 3.

Example 32: 5-[(Z)-2-[6-chloro-1-[(6-methoxy-3-pyridyl)methyl]indol-3-yl]-1-cyano-vinyl]pyridine-2-carboxylic Acid (Compound 2-3)

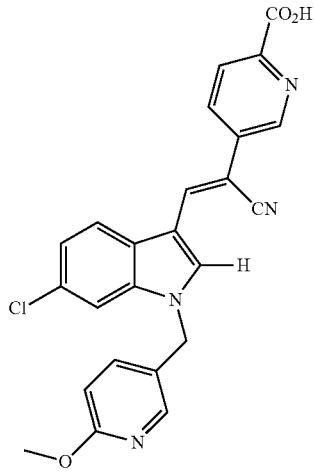

The title compound was prepared using the procedure for example 1 using 5-(chloromethyl)-2-methoxy-pyridine in step 2 and methyl 5-(cyanomethyl)pyridine-2-carboxylate in step 3.

Example 33: 3-[(Z)-2-(1-benzyl-6-chloro-indol-3-yl)-1-cyano-vinyl]benzoic Acid (Compound 2-4)

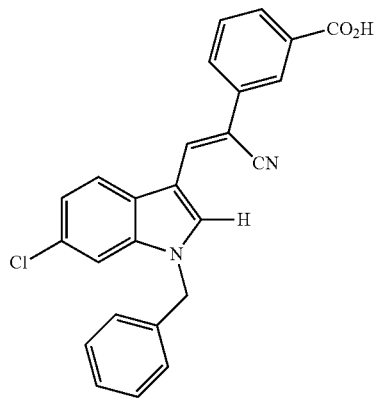 [SMILES: N#C/C(=C\c1cn(Cc2ccccc2)c2cc(Cl)ccc12)c1cccc(C(=O)O)c1]

The title compound was prepared using the procedure for example 1 using benzyl bromide in step 2 and methyl 3-(cyanomethyl)benzoate in step 3.

Example 34: 4-[(Z)-2-[6-chloro-1-[(4-fluorophenyl)methyl]indol-3-yl]-1-cyano-vinyl]benzenecarbohydroxamic Acid (Compound 2-5)

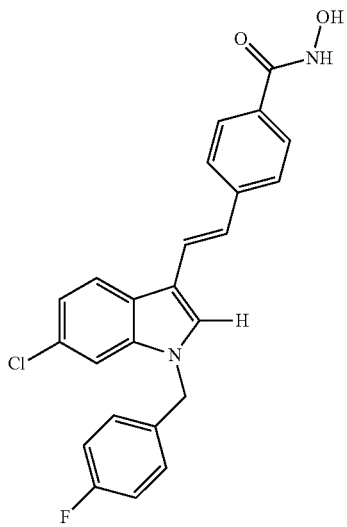 [SMILES: O=C(NO)c1ccc(/C=C/c2cn(Cc3ccc(F)cc3)c3cc(Cl)ccc23)cc1]

The title compound was prepared using the procedure for example 1 using oxalyl chloride and hydroxylamine hydrochloride after step 4.

Example 35: (Z)-4-(2-(6-chloro-1-(4-(trifluoromethoxy)benzyl)-1H-indol-3-yl)-1-cyanovinyl)benzoic Acid (Compound 1-45)

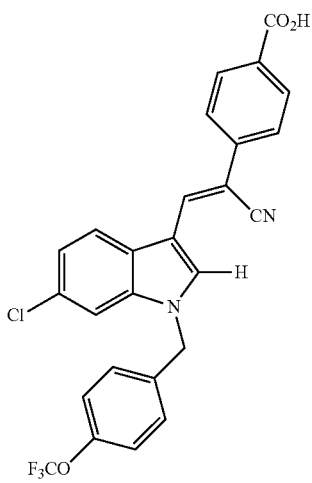 [SMILES: N#C/C(=C\c1cn(Cc2ccc(OC(F)(F)F)cc2)c2cc(Cl)ccc12)c1ccc(C(=O)O)cc1]

The title compound was prepared using the procedure for example 1 using 4-(trifluoromethoxy) benzylbromide in step 2.

117

Example 36: (Z)-4-(2-(6-chloro-1-(4-fluoro-2-(trifluoromethyl)benzyl)-1H-indol-3-yl)-1-cyanovinyl)benzoic Acid (Compound 1-46)

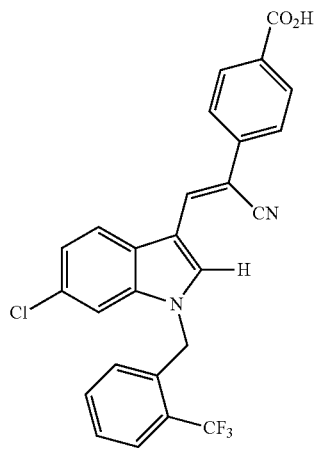 [SMILES: N#C/C(=C\c1cn(Cc2ccccc2C(F)(F)F)c2cc(Cl)ccc12)c1ccc(C(=O)O)cc1]

The title compound was prepared using the procedure for example 1 using 4-fluoro-2-(trifluoromethyl)benzylbromide in step 2.

Example 37: (Z)-4-(2-(6-chloro-1-(4-(difluoromethoxy)-2-fluorobenzyl)-1H-indol-3-yl)-1-cyanovinyl)benzoic Acid (Compound 1-47)

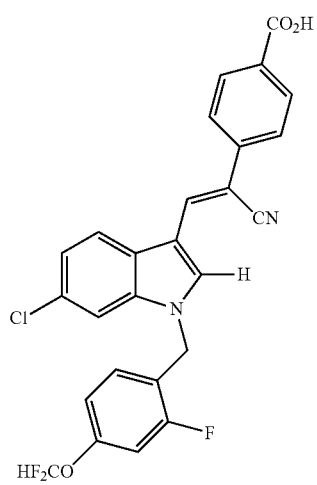

The title compound was prepared using the procedure for example 1 using 4-(difluoromethoxy)-2-fluorobenzylbromide in step 2.

118

Example 38: (Z)-4-(2-(6-chloro-1-((6-(2,2,2-trifluoroethoxy)pyridin-3-yl)methyl)-1H-indol-3-yl)-1-cyanovinyl)benzoic Acid (Compound 1-48)

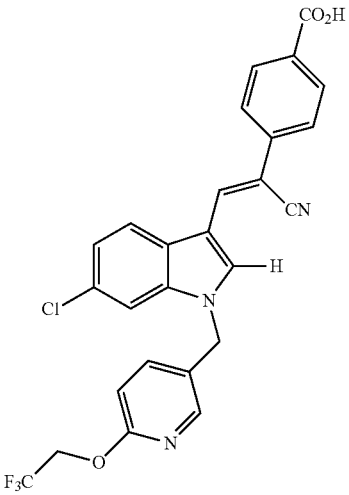 [SMILES: N#C/C(=C\c1cn(Cc2ccc(OCC(F)(F)F)nc2)c2cc(Cl)ccc12)c1ccc(C(=O)O)cc1]

The title compound was prepared using the procedure for example 1 using (2,2,2-trifluoroethoxy)pyridin-3-yl)methylchloride in step 2.

Example 39: (Z)-4-(1-cyano-2-(6-ethoxy-1-(4-fluorobenzyl)-1H-indol-3-yl)vinyl)benzoic Acid (Compound 1-65)

The title compound was prepared using the procedure for example 1 using 6-ethoxy-1H-indole in step 1.

119

Example 40: (Z)-4-(1-cyano-2-(1-(4-fluorobenzyl)-6-nitro-1H-indol-3-yl)vinyl)benzoic Acid (Compound 1-66)

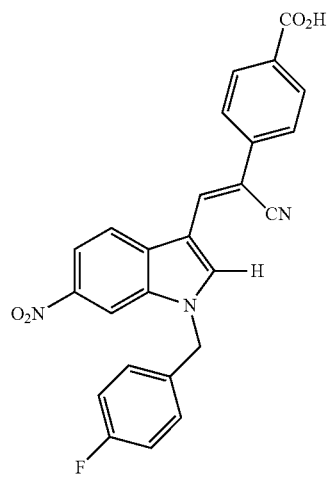 [SMILES: N#C/C(=C\c1cn(Cc2ccc(F)cc2)c2cc([N+](=O)[O-])ccc12)c1ccc(C(=O)O)cc1]

The title compound was prepared using the procedure for example 1 using 6-nitro-1H-indole in step 1.

Example 41: (Z)-4-(1-cyano-2-(1-(4-fluorobenzyl)-6-(methylsulfonyl)-1H-indol-3-yl)vinyl)benzoic Acid (Compound 1-67)

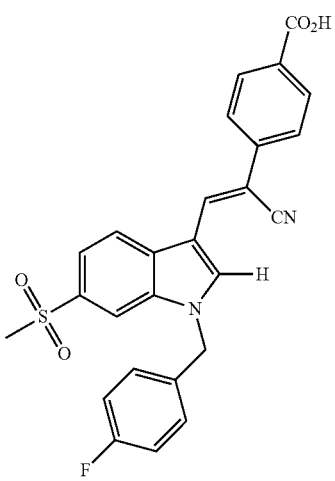 [SMILES: CS(=O)(=O)c1ccc2c(/C=C(\C#N)c3ccc(C(=O)O)cc3)cn(Cc3ccc(F)cc3)c2c1]

The title compound was prepared using the procedure for example 1 using 6-methylsulfonyl-1H-indole in step 1.

120

Example 42: (Z)-4-(2-(6-chloro-7-fluoro-1-(4-fluorobenzyl)-1H-indol-3-yl)-1-cyanovinyl)benzoic Acid (Compound 1-49)

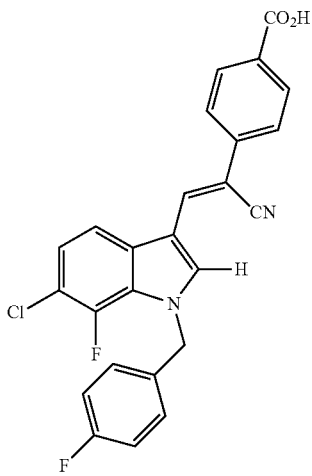 [SMILES: N#C/C(=C\c1cn(Cc2ccc(F)cc2)c2c(F)c(Cl)ccc12)c1ccc(C(=O)O)cc1]

Following the procedure of Example 1 but using 6-chloro-7-fluoro-1H-indole instead of 6-chloro-1H-indole as starting material, the title compound 1-49 was prepared as a yellow solid. LCMS [M+H]: 449

Example 43: (Z)-4-(1-cyano-2-(1-(6-methoxy-3-pyridyl)methyl)-6-chloro-7-fluoro-1H-indol-3-yl)vinyl)benzoic Acid (Compound 1-50)

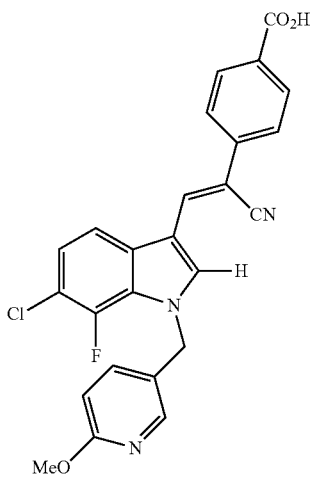 [SMILES: COc1ccc(Cn2cc(/C=C(\C#N)c3ccc(C(=O)O)cc3)c3ccc(Cl)c(F)c32)cn1]

Following the procedure of Example 1 but using 6-chloro-7-fluoro-1H-indole instead of 6-chloro-1H-indole and 5-(chloromethyl)-2-methoxypyridine instead 4-fluorobenzyl bromide the title compound 1-50 was prepared as a yellow solid. LCMS [M+H]: 462

Example 44: (Z)-4-(2-(6-chloro-7-fluoro-1-((6-methoxypyridin-3-yl)methyl)-1H-indol-3-yl)-1-cyanovinyl)benzoic Acid (Compound 1-52)

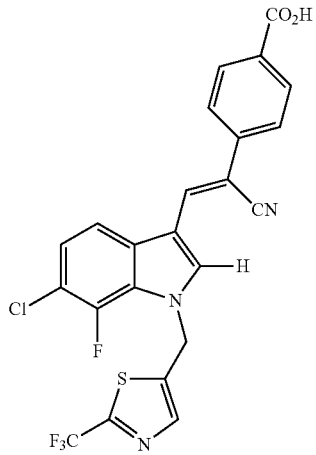 [SMILES: N#C/C(=C\c1cn(Cc2cnc(C(F)(F)F)s2)c2c(F)c(Cl)ccc12)c1ccc(C(=O)O)cc1]

Following the procedure of Example 1 but using 6-chloro-7-fluoro-1H-indole instead of 6-chloro-1H-indole and 2-trifluoromethyl-5-(bromomethyl)thiazole instead of 4-fluorobenzyl bromide the title compound 1-52 was prepared as a yellow solid. LCMS [M+H]: 506

Example 45: (Z)-4-(1-cyano-2-(1-(4-fluorobenzyl)-6-trifluoromethoxy-1H-indol-3-yl)vinyl)benzoic Acid (Compound 1-75)

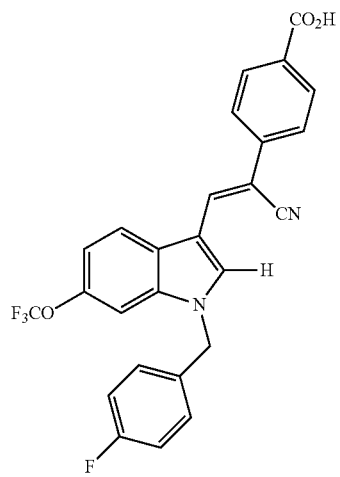 [SMILES: N#C/C(=C\c1cn(Cc2ccc(F)cc2)c2cc(OC(F)(F)F)ccc12)c1ccc(C(=O)O)cc1]

Following the procedure of Example 1 but using 6-(trifluoromethoxy)-1H-indole instead of 6-chloro-1H-indole as starting material, the title compound 1-75 was prepared as a yellow solid. LCMS [M+H]: 481.

Example 46: (Z)-4-(1-cyano-2-(1-(4-fluorobenzyl)-6-(trifluoromethoxy)-1H-indol-3-yl)vinyl)benzoic Acid (Compound 1-76)

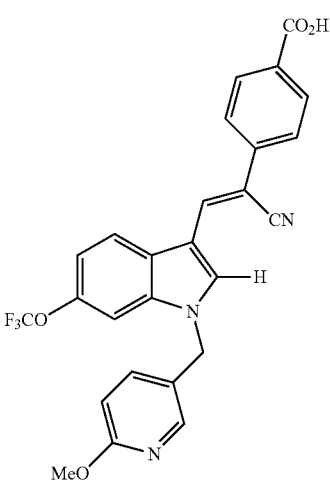 [SMILES: COc1ccc(Cn2cc(/C=C(\C#N)c3ccc(C(=O)O)cc3)c3ccc(OC(F)(F)F)cc32)cn1]

Following the procedure of Example 1 but using 6-(trifluoromethoxy)-1H-indole instead of 6-chloro-1H-indole as starting material, using 5-(chloromethyl)-2-methoxypyridine instead of 4-fluorobenzyl bromide, the title compound 1-76 was prepared as a yellow solid. LCMS [M+H]: 494.

Example 47: (Z)-4-(1-cyano-2-(6-(trifluoromethoxy)-1-((2-(trifluoromethyl)thiazol-5-yl)methyl)-1H-indol-3-yl)vinyl)benzoic Acid (Compound 1-77)

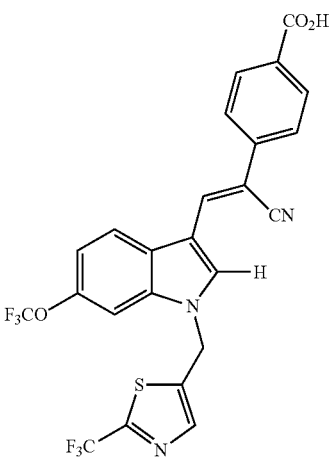 [SMILES: N#C/C(=C\c1cn(Cc2cnc(C(F)(F)F)s2)c2cc(OC(F)(F)F)ccc12)c1ccc(C(=O)O)cc1]

Following the procedure of Example 1 but using 6-(trifluoromethoxy)-1H-indole instead of 6-chloro-1H-indole as starting material, using 2-trifluoromethyl-5-(bromomethyl)thiazole instead of 4-fluorobenzyl bromide the title compound 1-77 was prepared as a yellow solid. LCMS [M+H]: 538.

Example 48: (Z)-2-(4-(2-(6-chloro-1-(4-fluorobenzyl)-1H-indol-3-yl)-1-cyanovinyl)phenyl)acetic Acid (Compound 2-25)

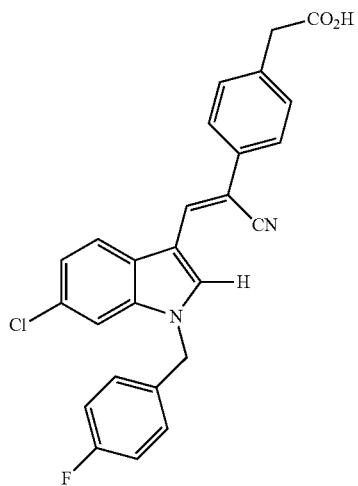 [SMILES: N#C/C(=C\c1cn(Cc2ccc(F)cc2)c2cc(Cl)ccc12)c1ccc(CC(=O)O)cc1]

The title compound was prepared using the procedure of Example 1 but using 4-(cyanomethyl)phenylacetic acid in place of methyl 4-(cyanomethyl)benzoate in step 3. LCMS: 446 ($M^+$+1).

Example 49: (Z)-(3-(2-(6-chloro-1-(4-fluorobenzyl)-1H-indol-3-yl)-1-cyanovinyl)benzoic Acid (Compound 2-26)

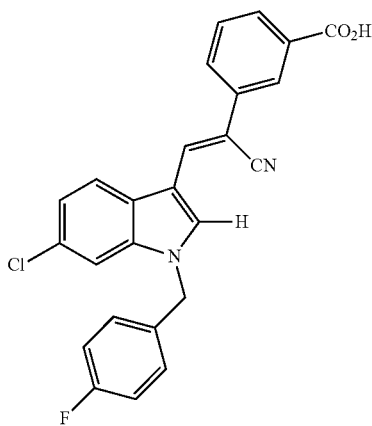 [SMILES: N#C/C(=C\c1cn(Cc2ccc(F)cc2)c2cc(Cl)ccc12)c1cccc(C(=O)O)c1]

The title compound was prepared using the procedure of Example 1 but using 3-(cyanomethyl)benzoic acid in place of methyl 4-(cyanomethyl)benzoate in step 3. LCMS: 446 ($M^+$+1).

Example 50: Parenteral Pharmaceutical Composition

To prepare a parenteral pharmaceutical composition suitable for administration by injection (subcutaneous, intravenous), 1-100 mg of a water-soluble salt of a compound Formula (I), Formula (II), Formula (III), Formula (IV), Formula (V), Formula (VI), or Formula (VII), or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example 51: Oral Solution

To prepare a pharmaceutical composition for oral delivery, a sufficient amount of a compound of Formula (I), Formula (II), Formula (III), Formula (IV), Formula (V), Formula (VI), or Formula (VII), or a pharmaceutically acceptable salt thereof, is added to water (with optional solubilizer(s), optional buffer(s) and taste masking excipients) to provide a 20 mg/mL solution.

Example 52: Oral Tablet

A tablet is prepared by mixing 20-50% by weight of a compound of Formula (I), Formula (II), Formula (III), Formula (IV), Formula (V), Formula (VI), or Formula (VII), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example 53: Oral Capsule

To prepare a pharmaceutical composition for oral delivery, 10-500 mg of a compound of Formula (I), Formula (II), Formula (III), Formula (IV), Formula (V), Formula (VI), or Formula (VII), or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound of Formula (I), Formula (II), Formula (III), Formula (IV), Formula (V), Formula (VI), or Formula (VII), or a pharmaceutically acceptable salt thereof, is placed into Size 4 capsule, or size 1 capsule (hypromellose or hard gelatin) and the capsule is closed.

Example 54: Topical Gel Composition

To prepare a pharmaceutical topical gel composition, a compound of Formula (I), Formula (II), Formula (III), Formula (IV), Formula (V), Formula (VI), or Formula (VII), or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example 55: Human Autotaxin Assay

ATX activity is assayed in concentrated conditioned media from Hep3B human hepatocellular carcinoma cells by measuring the amount of choline released from the substrate, lysophosphatidylcholine (LPC) as it is cleaved to LPA. Conditioned media is collected from confluent Hep3B cells and concentrated 20-fold using Centriprep-30 filter devices (Millipore). To assay for autotaxin inhibition, 10-20

µL of the concentrated conditioned media is incubated with 2.5 µL of a test compound in DMSO and 72.5-82.5 µL lyso-PLD buffer (100 mM Tris pH 9, 500 mM NaCl, 5 mM $MgCl_2$, 5 mM $CaCl_2$, 0.05% Triton X-100 in the presence or absence of 0.2% fatty-acid-free human serum albumin) for 15 min at 37° C. After the 15 min incubation, 5 ul of 2 mM LPC (14:0; Avanti Polar Lipids Cat#855575C) diluted in lyso-PLD buffer is added for a final concentration of 100 uM and the incubation continues for 1.5-3 hours at 37° C. 100 µl of a color mix containing 4.5 mM 4-aminoantipyrine, 2.7 mM N-ethyl-N-(2-hydroxy-3-sulfopropyl)-m-toluidine, 21 units/ml horseradish peroxidase and 3 units/ml choline oxidase in 50 mM Tris, pH 8, 4.5 mM $MgCl_2$ is added and the incubation continued for 15 minutes at room temperature before reading the absorbance at 555 nm.

Illustrative biological activity of representative compounds in the human autotaxin assay described herein is presented in the following table:

| Compound number | $IC_{50}$ (µM) |
| --- | --- |
| 1-1 | B |
| 1-2 | B |
| 1-3 | C |
| 1-4 | A |
| 1-5 | B |
| 1-6 | B |
| 1-7 | A |
| 1-8 | B |
| 1-9 | B |
| 1-10 | A |
| 1-11 | A |
| 1-12 | C |
| 1-13 | B |
| 1-14 | B |
| 1-15 | A |
| 1-16 | A |
| 1-17 | B |
| 1-18 | B |
| 1-19 | B |
| 1-20 | C |
| 1-21 | B |
| 1-22 | C |
| 1-23 | C |
| 1-24 | B |
| 1-25 | B |
| 1-26 | A |
| 1-27 | A |
| 1-28 | C |
| 1-29 | A |
| 1-45 | B |
| 1-46 | C |
| 1-47 | B |
| 1-48 | C |
| 1-49 | B |
| 1-50 | A |
| 1-52 | A |
| 1-65 | A |
| 1-66 | A |
| 1-67 | B |
| 1-75 | A |
| 1-76 | A |
| 1-77 | A |
| 2-1 | C |
| 2-2 | A |
| 2-3 | A |
| 2-4 | B |
| 2-5 | B |
| 2-25 | A |
| 2-26 | B |

A is ≤0.5 µM;
B is >0.5 µM but ≤10 µM;
C >10 µM.

Example 56: Human Whole Blood Autotaxin Assay

Inhibition of ATX activity in human whole blood is assayed by measuring the concentration of 20:4 LPA in plasma after a prolonged incubation at 37° C. Blood is drawn from consenting human volunteers into heparin vacutainer tubes and 200 µl aliquots are added to 2 µl test compound in DMSO or DMSO alone. Several of the vehicle tubes are centrifuged immediately at 800×g for 10 minutes at 4° C. and the plasma removed for processing to determine the baseline concentration of 20:4 LPA. The remaining blood samples containing vehicle or test compound are incubated at 37° C. for 4 hours before centrifuging at 800×g for 10 minutes at 4° C. to obtain plasma. Plasma is processed for LCMS as follows: 40 ul plasma is removed and 5 volumes of methanol containing 125 ng/ml 17:0 LPA as an internal standard are added and the mixture incubated at −20° C. for 10 min before centrifuging at 4000×g for 10 minutes at 4° C. 150 µl of the supernatant is transferred to a 96-well plate and diluted with 100 µl of an organic solution (90:10:0.1 of water/acetonitrile/ammonium hydroxide) for analysis of 20:4 LPA concentrations by LCMS. LPA 20:4 and the internal standard (LPA 17:0) were analyzed on a quadrupole mass spectrometer (ABI Sciex 4000QTrap) in the negative ion mode (ESI) by multiple reaction monitoring (MRM). The mobile phases contain 0.1% ammonium hydroxide in 90% water/10% acetonitrile (solvent A) and 0.1% ammonium hydroxide in 90% acetonitrile/10% water (solvent B). The flow rate was maintained at 0.8 mL/min and the total run time was 3 min. Analytes were separated using a linear gradient as follows: 1) mobile phase was held for 0.5 min at 10% B; 2) B was increased from 10% to 90% over the next 1 min; 3) B was held constant for 0.5 min at 90%; and 4) B was returned to the initial gradient conditions.

Example 57: Mouse Air Pouch Assay

LPA and ATX activity are induced by carrageenan injection into a mouse air pouch. A mouse air pouch assay was utilized to determine pharmacodynamic activity of autotaxin inhibitors in reducing carrageenan-induced ATX activity and LPA biosynthesis. An air pouch was formed in female balb/c mice by instilling 5 ml of 0.2 µm filtered air into the subcutaneous space in the scapular region on Day 1. On Day 3, 3 ml of air was instilled into the pouch and on Day 6, another 3 ml air was instilled into the pouch. On Day 7, test compounds were administered by oral gavage. At the appropriate time (0-24 hr) after compound administration, carrageenan dissolved in sterile saline was injected into the air pouch. Two hours following carrageenan challenge, mice were sacrificed and blood obtained via cardiac puncture. A 0.5-1 ml bolus of bolus of ice-cold phosphate buffered saline solution was instilled into the air pouch and after 20 seconds of gentle massaging, the pouch was opened and the fluid removed. An aliquot of the air pouch fluid was analyzed for LPA concentrations by LC-MS as described in the Human Whole Blood Autotaxin Assay (Example 47). A separate aliquot of the air pouch fluid was taken, centrifuged (800×g, 10 min) and assayed for choline content using a TOOS method or for drug concentrations by LCMS. Plasma prepared from blood was assayed for drug concentrations by LCMS. Drug concentrations to achieve 50% inhibition of ATX activity or carrageenan-induced pouch LPA could be calculated by nonlinear regression (Graphpad Prism) of % inhibition versus log drug concentration.

Example 58: MDA-MB-435 Melanoma Cell Migration Assay

Cells from the MDA-MB-435S human melanoma line are maintained in subconfluent culture in media containing FBS and penicillin/streptomycin. The day before the assay, cells are serum-starved overnight in media containing 0.1-0.2% fatty-acid-free BSA. On the day of the assay, the conditioned media is removed from the cells and set aside. The cells are then harvested by scraping, counted, and pelleted by centrifugation. The cells are resuspended at 1.05× the final desired density in the conditioned media. The assays are performed in duplicate using the Neuroprobe 96-well chemotaxis system with 8 µm pore size and fibronectin-coated filters. 152 µl cells are added to 8 µl test compound and incubated for 15 min at 37° C. The lower chamber is loaded with 2-10 µM LPC and then 50 µl of the cell/test compound suspension is added to the top of each filter well site. The filters are incubated at 37° C. for 1-24 hours and non-migrated cells removed from the top of the filter by rinsing with PBS and scraping. The filter is air dried then stained before reading the absorbance at 580 nm.

Example 59: Spontaneous Metastasis Mouse Model

A syngeneic mouse model is used to test efficacy of compounds in inhibiting tumor metastases. 4T1 cells are injected into the #7 mammary fat pad of female Balb/c mice while the mice are anesthetized. The primary tumors are measured by caliper twice weekly until they are resected under isofluorane anesthesia (between days 10-14). Test compound is administered orally daily at various times after the injection of the 4T1 cells. At 8-11 weeks after the 4T1 injection, lymph nodes, lungs, liver and any other organs suspected of harboring metastases are collected for histological analysis.

Example 60: Lung Metastases Model

An experimental lung metastasis model is used to test efficacy of compounds in reducing the number of metastases of injected B16-F 10 mouse melanoma cells to the lung. Briefly, female C57BL/6J mice, female (BALB/cByJ× C57BL/6J)Fi, mice (CByB6Fi/J), athymic nude female and male CByB6Fi/J mice (nu/nu), and control littermates (nu/nu) are used at ages 7-18 weeks, when they weighed between 18 and 28 g. A single-cell suspension of B16F10 cells, harvested in log phase (approx. $5\text{-}10\times10^4$ cells) in 0.2 mL of Hanks' balanced salt solution are injected intravenously into the lateral tail vein of the mice. Test compound or vehicle is delivered daily. After 21 days, the mice are sacrificed, and the lungs are removed. Lungs are fixed in 10% buffered formalin overnight and weighed, and tumor colonies at the surface are scored with the aid of a dissecting microscope.

Example 61: Mouse Carbon Tetrachloride ($CCl_4$)-Induced Liver Fibrosis Model Female balb/c mice receive $CCl_4$ (1.0 ml/kg body weight) diluted in olive oil via intraperitoneal injection twice a week for 8 weeks. (Higazi, A. A. et al, Clin Exp Immunol. 2008 April; 152(1):163-73). Control mice receive an equivalent volume of olive oil only. Test compound or vehicle is delivered orally daily. At the end of the study (8 weeks after first i.p. injection of $CCl_4$), mice are sacrificed using inhaled isoflurane and blood is drawn via cardiac puncture for subsequent analysis of ALT/AST levels. The liver is harvested and frozen at −80° C. for the biochemical analysis of liver fibrosis or fixed in 10% neutral buffered formalin for histological assessment of liver fibrosis. For the biochemical assessment of liver fibrosis, liver tissue homogenates are analyzed for collagen concentration using a hydroxyproline assay. For the histological assessment of liver fibrosis, fixed liver tissue is Masson's trichrome stained and liver fibrosis is determined by quantitative, computer-assisted densitometry using light microscopy.

Example 62: Rat Diethylnitrosamine (DEN)-Induced Liver Fibrosis and Hepatocellular Carcinoma Male Wistar rats receive weekly intraperitoneal injections of 35-100 mg/kg diethylnitrosamine (DEN) for 5-18 weeks in a total volume of 1.5 ml phosphate-buffered saline (PBS) to induce cirrhosis and hepatocellular carcinoma (HCC). Control rats receive weekly injections of an equivalent volume of PBS. Test compound or vehicle is delivered orally daily. At the end of the study, rats are sacrificed using inhaled isoflurane and blood is drawn via cardiac puncture for subsequent analysis of ALT/AST levels and drug concentrations. The liver is harvested and frozen at −80° C. for biochemical analysis of fibrosis or fixed in 10% neutral buffered formalin for histological assessment of liver fibrosis. For biochemical assessment of fibrosis, liver tissue homogenates are analyzed for collagen concentration using a hydroxyproline assay. For histological assessment of liver fibrosis and HCC, fixed liver tissue is hematoxylin and eosin stained and Masson's trichrome stained and liver fibrosis and HCC is determined by quantitative, computer-assisted densitometry using light microscopy.

Example 63: Clinical Trial for Pulmonary Fibrosis

A non-limiting example of a pulmonary fibrosis clinical trial in humans is described below.

Purpose:

The purposes of this study are to assess the efficacy of a compound of Formula (I), Formula (II), Formula (III), Formula (IV), Formula (V), Formula (VI), or Formula (VII), or a pharmaceutically acceptable salt thereof, as single agent or in combination, in the treatment of patients with pulmonary fibrosis, collect information on any side effects the compound may cause as single agent or in combination, and evaluate the pharmacokinetic properties of the compound as single agent or in combination.

Intervention:

Patients are administered 0.1-100 mg/kg of a compound of Formula (I), Formula (II), Formula (III), Formula (IV), Formula (V), Formula (VI), or Formula (VII), or a pharmaceutically acceptable salt thereof, per day as single agent or in combination.

Detailed Description:

Patients will be given a compound of Formula (I), Formula (II), Formula (III), Formula (IV), Formula (V), Formula (VI), or Formula (VII), or a pharmaceutically acceptable salt thereof, orally once or twice a day as single agent or in combination. Prior to each dosing cycle, a physical exam, blood work and assessment of any side effects will be performed.

Primary Outcome Measures:

Progression-free survival, defined as free of death or a decrease from baseline in the FVC of at least 10%.

Secondary Outcome Measures:

Number of Acute Exacerbations of IPF; health related quality of life; PO$_2$ at rest and at exercise from baseline; P(A-a)O$_2$ at rest and at exercise from baseline; Predicted FEV1 from baseline; forced expiratory volume in one second (FEV1) to FVC from baseline; plethysmographic lung volumes from baseline; diffusion capacity for carbon monoxide (DLco) from baseline; Six-Minute Walk test, from baseline: resting and 6 minute SpO2, presence or absence of desaturation to 88% or lower at the end of the six minute walk, walked distance; Pre and post modified Borg dyspnea scores; scoring of extent of lung fibrosis on HRCT, according to two independent chest radiologists, form baseline; number and severity of adverse effects.

Eligibility:

Male and female subjects that are 40 years to 80 years.

Inclusion Criteria:

Clinical symptoms of IPF for at least 3 months; forced vital capacity (FVC) between 50 to 90% of the predicted value; DLco at least 35% of the predicted value; PaO2>55 mm Hg while breathing ambient air at rest; High-resolution computed tomography (HRCT) showing definite or probable criteria of IPF.

Exclusion Criteria:

Clinically significant exposure to known fibrogenic agents (birds, molds, asbestos, radiation and drugs known to cause pulmonary fibrosis (amiodarone, nitrofurantoin, bleomicin, etc)); history of neurofibromatosis, Hermansky-Pudlak syndrome, metabolic storage disorders, etc.; history of fever, weight loss, myalgias, arthralgias, skin rash, arthritis; active infection within one week before enrollment; alternative cause of interstitial lung disease; ratio of the forced expiratory volume in one second (VEF1) to FVC of less than 0.6 after the use of a bronchodilator; residual volume more than 120% of the predicted value (when available); more than 20% of lymphocytes or eosinophils in bronchoalveolar lavage (BAL) (when available); granulomas, infection or malignancy in the transbronchial or surgical biopsy (when available); previous therapy with azathioprine, prednisolone (>0.5 mg/kg/day or more for at least 3 months), cyclophosphamide or novel biotech drugs; unstable cardiovascular or neurologic disease; uncontrolled diabetes; pregnancy; lactation; likelihood of death, as predicted by the investigator, within the next year; white cell blood count <4000/mm3; platelet count <100000/mm3; Hematocrit <30% or >59%; liver enzymes more than 3 times the upper limit of the normal range; creatinine level >1.5 mg/dL; albumin level <3 g/dL; refusal to sign informed consent by patient or guardian.

Example 64: Clinical Trial for Liver Fibrosis

A non-limiting example of a liver fibrosis clinical trial in humans is described below.

Purpose:

The purposes of this study are to assess the efficacy of a compound of Formula (I), Formula (II), Formula (III), Formula (IV), Formula (V), Formula (VI), or Formula (VII), or a pharmaceutically acceptable salt thereof, as single agent or in combination, in the treatment of patients with liver fibrosis, collect information on any side effects the compound may cause as single agent or in combination, and evaluate the pharmacokinetic properties of the compound as single agent or in combination.

Intervention:

Patients are administered 1-100 mg/kg of a compound of Formula (I), Formula (II), Formula (III), Formula (IV), Formula (V), Formula (VI), or Formula (VII), or a pharmaceutically acceptable salt thereof, per day as single agent or in combination.

Detailed Description:

Patients will be given a compound of Formula (I), Formula (II), Formula (III), Formula (IV), Formula (V), Formula (VI), or Formula (VII), or a pharmaceutically acceptable salt thereof, orally once or twice a day as single agent or in combination. Prior to each dosing cycle, a physical exam, blood work and assessment of any side effects will be performed.

Primary Outcome Measures:

Liver enzymes (ALT, AST, ALP), liver biopsy

Secondary Outcome Measures:

Pharmacodynamic markers may include: Tissue PD markers through mRNA expression, ATX, LOXL2, LOX, Other LOXL proteins, αSMA, Collagen 1A1, NF-κB1, Caspase 1, SMAD, and NOD; Serum and plasma PD markers include: AST-to-platelet ratio index (APRI), ATX activity, LOXL2, Osteopontin, Hyaluronic Acid, CXCL 9, 10 and 11, MMP1, MMP3, MMP9, TIMP1, CD40L, TGF-β1, ET-1, VEGF, GAL3, IL-6/IL-8/TNFα/IFNγ, α2-macroglobulin, Apolipoprotein A1, PINP, PIIINP, PVCP-1230, PDGF; Assessing the effects of chronic dosing on liver structure (using, for example, ultrasound and/or MRI) and fibrotic markers; incidence of adverse events resulting from the administration of multiple doses of compound.

Eligibility:

Male and female subjects that are 18 to 60 years old.

Inclusion Criteria:

Stage 1-3 fibrosis by Metavir score on a liver biopsy; Body mass index <36 kg/m2.

Exclusion Criteria:

Any evidence of hepatic decompensation past or present; subjects currently abusing amphetamines, cocaine, opiates, or alcohol; clinically significant cardiac disease; history of cancer, other than non-melanomatous skin cancer, within 5 years prior to screening; systemic fungal, bacterial, viral, or other infection that is not controlled; use of systemic immunosuppressants within 28 days of the Pre-treatment Phase; use of approved therapy for hepatitis C or hepatitis B virus within 28 days of the Pre-treatment Phase; pregnant or lactating; history of bleeding diathesis within the last 6 months of study Day 1.

Example 65: Clinical Trial for Cholestatic Pruritus

A non-limiting example of a cholestatic pruritus clinical trial in humans is described below.

Purpose:

The purposes of this study are to assess the efficacy of a compound of Formula (I), Formula (II), Formula (III), Formula (IV), Formula (V), Formula (VI), or Formula (VII), or a pharmaceutically acceptable salt thereof in the treatment of patients with cholestatic pruritus, collect information on any side effects the compound may cause and evaluate the pharmacokinetic properties of the compound as single agent or in combination.

Intervention:

Patients are administered 0.1-100 mg/kg of a compound of Formula (I), Formula (II), Formula (III), Formula (IV), Formula (V), Formula (VI), or Formula (VII), or a pharmaceutically acceptable salt thereof, per day.

Detailed Description:

Patients will be given a compound of Formula (I), Formula (II), Formula (III), Formula (IV), Formula (V), Formula (VI), or Formula (VII), or a pharmaceutically acceptable salt thereof, orally once or twice a day. Prior to each dosing cycle, a physical exam, blood work and assessment of any side effects will be performed.

Eligibility:

Male and female subjects that are 21 to 80 years old.

Inclusion Criteria:

Patients with pruritus as a result of a cholestatic disorder.

Exclusion Criteria:

Use of cholestyramine; pregnancy; malignancy/life expectancy <6 months.

Primary Outcome Measures:

Normalization of liver enzymes (ALT, AST, ALP), Reduction of pruritus according to visual analogue scores.

Secondary Outcome Measures:

Improvement in quality of life scores; reduction in pruritus score/scratch lesions.

Example 66: Clinical Trial for Pancreatic Cancer

A non-limiting example of a pancreatic cancer clinical trial in humans is described below.

Purpose:

The purposes of this study are to assess the efficacy of a compound of Formula (I), Formula (II), Formula (III), Formula (IV), Formula (V), Formula (VI), or Formula (VII), or a pharmaceutically acceptable salt thereof, as single agent or in combination, in the treatment of patients with pancreatic cancer, collect information on any side effects the compound may cause as single agent or in combination, and evaluate the pharmacokinetic properties of the compound as single agent or in combination.

Intervention:

Patients are administered 0.1-100 mg/kg of a compound of Formula (I), Formula (II), Formula (III), Formula (IV), Formula (V), Formula (VI), or Formula (VII), or a pharmaceutically acceptable salt thereof, per day as single agent or in combination.

Detailed Description:

Patients will be given a compound of Formula (I), Formula (II), Formula (III), Formula (IV), Formula (V), Formula (VI), or Formula (VII), or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old with advanced pancreatic cancer.

Inclusion Criteria:

Radiographic or clinical evidence of measurable advanced pancreatic carcinoma (Stage II, III, IV). Subjects must have measurable disease at least 2 cm in diameter. ECOG performance status of 0 or 1.

Exclusion Criteria:

Prior history of malignancy (except basal cell or squamous cell carcinoma or carcinoma in situ of the breast) unless the subject has been free of disease for > or = to 1 year. Moderate or severe cardiac disease; Active infection; Not pregnant or nursing; Negative pregnancy test; Fertile patients must use effective contraception during and for ≥3 months after completion of study treatment; Able to swallow oral medication; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures:

Progression free survival, overall survival, worsening of pain, onset of pain

Secondary Outcome Measures:

tumor size/response (RECIST)

Example 67: Clinical Trial for Hepatocellular Carcinoma (HCC)

A non-limiting example of a hepatocellular carcinoma clinical trial in humans is described below.

Purpose:

The purposes of this study are to assess the efficacy of a compound of Formula (I), Formula (II), Formula (III), Formula (IV), Formula (V), Formula (VI), or Formula (VII), or a pharmaceutically acceptable salt thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention:

Patients are administered 0.1-100 mg/kg of a compound of Formula (I), Formula (II), Formula (III), Formula (IV), Formula (V), Formula (VI), or Formula (VII), or a pharmaceutically acceptable salt thereof, per day as single agent or in combination.

Detailed Description:

Patients will be given a compound of Formula (I), Formula (II), Formula (III), Formula (IV), Formula (V), Formula (VI), or Formula (VII), or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old.

Inclusion Criteria:

Patients with histopathologically or clinically confirmed diagnosis of hepatocellular carcinoma; unresponsive to standard therapy or for whom standard therapy is intolerable, or for whom there is no appropriate therapy; ECOG performance status score of 0-2.

Exclusion Criteria:

Patients with a primary malignant tumor; history of liver transplant; brain metastases; psychiatric disorder that might cause difficulty in obtaining informed consent or in conducting the trial; Not pregnant or nursing; Fertile patients must use effective contraception during and for ≥3 months after completion of study treatment; No other malignancy within the past 5 years except for in situ cancers or basal cell or squamous cell carcinoma of the skin; No hypersensitivity or intolerance to statins; no other non-malignant systemic disease that would preclude rosuvastatin administration or prolonged follow-up.

Primary Outcome Measures:

time to progression, progression free survival, overall response (RECIST)

Secondary Outcome Measures:

liver function tests, tumor biomarkers, liver imaging (Ultrasound, MRI, PET).

Example 68: Clinical Trial for Fatty Liver Disease/Steatosis (NAFLD, NASH)

A non-limiting example of a fatty liver disease/steatosis clinical trial in humans is described below.

Purpose:

The purposes of this study are to assess the efficacy of a compound of Formula (I), Formula (II), Formula (III), Formula (IV), Formula (V), Formula (VI), or Formula (VII), or a pharmaceutically acceptable salt thereof, as single agent or in combination, in the treatment of patients with hepatocellular carcinoma, collect information on any side effects the compound may cause as single agent or in combination, and evaluate the pharmacokinetic properties of the compound as single agent or in combination.

Intervention:

Patients are administered 0.1-100 mg/kg of a compound of Formula (I), Formula (II), Formula (III), Formula (IV), Formula (V), Formula (VI), or Formula (VII), or a pharmaceutically acceptable salt thereof, per day as single agent or in combination.

Detailed Description:

Patients will be given a compound of Formula (I), Formula (II), Formula (III), Formula (IV), Formula (V), Formula (VI), or Formula (VII), or a pharmaceutically acceptable salt thereof, orally once or twice a day as single agent or in combination. Prior to each dosing cycle, a physical exam, blood work and assessment of any side effects will be performed.

Eligibility:

Male and female subjects that are 21 to 80 years old.

Inclusion Criteria:

Patients with clinically confirmed diagnosis of non-alcohol fatty liver disease or non-alcohol steatohepatitis; histologic evidence of definite or probable nonalcoholic steatohepatitis (NASH) based upon a liver biopsy obtained no more than 90 days prior to randomization and a nonalcoholic fatty liver disease activity score (NAS) of 4 or greater.

Exclusion Criteria:

Current or history of significant alcohol consumption, use of drugs historically associated with nonalcoholic fatty liver disease (NAFLD) (amiodarone, methotrexate, systemic glucocorticoids, tetracyclines, tamoxifen, estrogens at doses greater than those used for hormone replacement, anabolic steroids, valproic acid, and other known hepatotoxins) for more than 2 weeks in the year prior to randomization, prior or planned (during the study period) bariatric surgery (eg, gastroplasty, roux-en-Y gastric bypass), uncontrolled diabetes defined as Hemoglobin A1c 9.5% or higher within 60 days prior to enrollment, presence of cirrhosis on liver biopsy, platelet count below 100,000/mm3; Clinical evidence of hepatic decompensation as defined by the presence of any of the following abnormalities: serum albumin less than 3.2 grams/deciliter (g/dL), INR (international normalized ratio) greater than 1.3, direct bilirubin greater than 1.3 milligrams per deciliter (mg/dL), history of esophageal varices, ascites or hepatic encephalopathy; Evidence of other forms of chronic liver disease: hepatitis B as defined by presence of hepatitis B surface antigen (HBsAg), hepatitis C as defined by presence of hepatitis C virus (HCV) ribonucleic acid (RNA) or positive hepatitis C antibody (anti-HCV), evidence of ongoing autoimmune liver disease as defined by compatible liver histology, primary biliary cirrhosis, primary sclerosing cholangitis, Wilson's disease, Alpha-1-antitrypsin (A1AT) deficiency, history of hemochromatosis or iron overload, drug-induced liver disease as defined on the basis of typical exposure and history, known bile duct obstruction, suspected or proven liver cancer, any other type of liver disease other than nonalcoholic steatohepatitis (NASH); serum alanine aminotransferase (ALT) greater than 300 units per liter (U/L); serum creatinine of 2.0 mg/dL or greater; use of ursodeoxycholic acid (Ursodiol, Urso) within 90 days prior to enrollment; inability to safely obtain a liver biopsy, history of biliary diversion, known positivity for Human Immunodeficiency Virus (HIV) infection; pregnancy, planned pregnancy, potential for pregnancy and unwillingness to use effective birth control during the trial, breast feeding Primary Outcome Measures:

liver function tests, liver biopsy, NAS score

Secondary Outcome Measures:

fibrotic biomarkers, liver imaging (ultrasound, MRI), insulin resistance as measure by HOMA-IR, lipid panel, glucose homeostasis (OGTT).

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt, or solvate thereof:

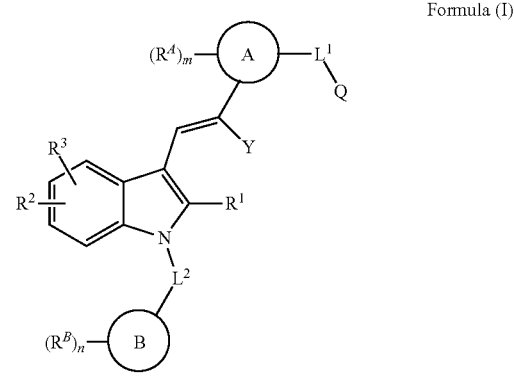

Formula (I)

wherein, $R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl;

$R^2$ is halogen, —CN, —OH, —OR$^9$, —NO$_2$, —NH$_2$, —N(R$^{10}$)$_2$, —OC(=O)N(R$^{10}$)$_2$, —C(=O)N(R$^{10}$)$_2$, —NHC(=O)R$^9$, —NHC(=O)OR$^9$, substituted or unsubstituted $C_1$-$C_4$alkyl, $C_1$-$C_4$fluoroalkyl, $C_1$-$C_4$deuteroalkyl, substituted or unsubstituted $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, $C_1$-$C_4$hydroxyalkyl or substituted or unsubstituted phenyl, or monocyclic heteroaryl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each $R^4$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;

m is 0, 1, or 2;

$L^1$ is absent, $C_1$-$C_6$alkylene, $C_1$-$C_6$fluoroalkylene, $C_3$-$C_6$cycloalkylene, $(C_1$-$C_6$alkylene$)_p$-$C_3$-$C_6$cycloalkylene-$(C_1$-$C_6$alkylene$)_q$, or —$(C_1$-$C_6$alkylene$)_p$-X—$(C_1$-$C_6$alkylene$)_q$;

X is O, S, S(=O), S(=O)$_2$, C(=O)NH, NHC(=O), NH, OC(=O)NH, NHC(=O)O, or NHC(=O)O;

p is 0 or 1;

q is 0 or 1;

Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;

$L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent;

Y is H, $C_1$-$C_6$alkyl, halogen, or CN;

Ring B is a monocyclic aryl, bicyclic aryl, monocyclic heteroaryl or bicyclic heteroaryl;

each R$^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl;

n is 0, 1, or 2;

each R$^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, —$C_1$-$C_4$alkylene-(substituted or unsubstituted monocyclic heteroaryl), a substituted or unsubstituted bicyclic heteroaryl and —$C_1$-$C_4$alkylene-(substituted or unsubstituted bicyclic heteroaryl);

each R$^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, and —$C_1$-$C_4$alkylene-(substituted or unsubstituted monocyclic heteroaryl); or two R$^{10}$ groups attached to the same N atom are taken together with the N atom to which they are attached to form a substituted or unsubstituted heterocycle.

2. The compound of claim 1, or a pharmaceutically acceptable salt, or solvate thereof, wherein:

R$^1$ is H, halogen, —CN, —C(=O)H, $C_1$-$C_4$alkyl, $C_1$-$C_4$fluoroalkyl, or $C_1$-$C_4$deuteroalkyl;

R$^2$ is halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

R$^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each R$^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;

m is 0, 1, or 2;

$L^1$ is absent, $C_1$-$C_6$alkylene, $C_1$-$C_6$fluoroalkylene, $C_3$-$C_6$cycloalkylene, $(C_1$-$C_6$alkylene$)_p$-$C_3$-$C_6$cycloalkylene-$(C_1$-$C_6$alkylene$)_q$, or —$(C_1$-$C_6$alkylene$)_p$-X—$(C_1$-$C_6$alkylene$)_q$;

X is O, S, S(=O), S(=O)$_2$, C(=O)NH, NHC(=O), NH, OC(=O)NH, NHC(=O)O, or NHC(=O)O;

p is 0 or 1;

q is 0 or 1;

Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;

$L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent;

Y is H, $C_1$-$C_6$alkyl, halogen, or CN;

Ring B is a monocyclic aryl, bicyclic aryl, monocyclic heteroaryl or bicyclic heteroaryl;

each R$^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl;

n is 0, 1, or 2;

each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, a substituted or unsubstituted monocyclic heteroaryl, and a substituted or unsubstituted bicyclic heteroaryl;

each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, and a substituted or unsubstituted monocyclic heteroaryl; or two $R^{10}$ groups attached to the same N atom are taken together with the N atom to which they are attached to form a substituted or unsubstituted heterocycle.

3. The compound of claim 1, or a pharmaceutically acceptable salt, or solvate thereof, wherein:
$R^1$ is H, F, Cl, —CN, —C(=O)H, —CH$_3$, —CF$_3$, or —CD$_3$;
$L^1$ is absent, —CH$_2$—, —CH$_2$CH$_2$—, —CH$_2$CH$_2$CH$_2$—, —CH(CH$_3$)—, —CH(CH$_2$CH$_3$)—, —C(CH$_3$)$_2$—, —C(CH$_2$CH$_3$)$_2$—, cyclopropyl-1,1-diyl, cyclobutyl-1,1-diyl, cyclopentyl-1,1-diyl or cyclohexyl-1,1-diyl;
Q is —CO$_2$H, —CO$_2$(C$_1$-C$_6$alkyl), —C(=O)NHSO$_2$R$^9$ or tetrazolyl;
$L^2$ is —C$_1$-C$_6$alkylene-;
Y is H, —CH$_3$, F, Cl, Br, or CN.

4. The compound of claim 3, wherein the compound of Formula (I) has the following structure of Formula (II):

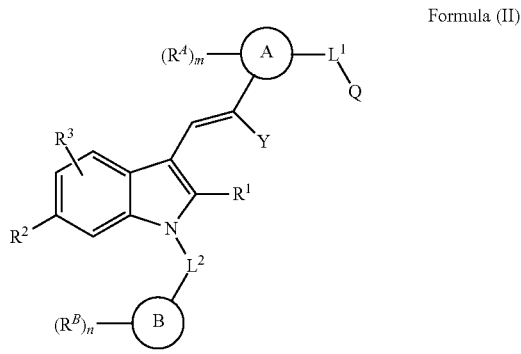

Formula (II)

wherein,
$L^2$ is —CH$_2$—, —CH$_2$CH$_2$—, —CH$_2$CH$_2$CH$_2$—, or —CH(CH$_3$)—;

or is a pharmaceutically acceptable salt, or solvate thereof.

5. The compound of claim 4, or a pharmaceutically acceptable salt, or solvate thereof, wherein:
Ring A is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic heteroaryl containing 0-4 N atoms and 1 O or S atoms;
Ring B is phenyl, naphthyl, monocyclic heteroaryl containing 1-4 N atoms and 0 or 1 O or S atoms, monocyclic heteroaryl containing 0-4 N atoms and 1 O or S atoms, bicyclic heteroaryl containing 1-4 N atoms and 0 or 1 O or S atoms, or bicyclic 6 heteroaryl containing 0-4 N atoms and 1 O or S atoms.

6. The compound of claim 4, or a pharmaceutically acceptable salt, or solvate thereof, wherein:
Ring A is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl;
Ring B is phenyl, naphthyl, furanyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, pyridazinyl, triazinyl, quinolinyl, isoquinolinyl, quinazolinyl, quinoxalinyl, naphthyridinyl, indolyl, indazolyl, benzoxazolyl, benzisoxazolyl, benzofuranyl, benzothienyl, benzothiazolyl, benzimidazolyl, purinyl, cinnolinyl, phthalazinyl, pteridinyl, pyridopyrimidinyl, pyrazolopyrimidinyl, or azaindolyl.

7. The compound of claim 3, wherein the compound of Formula (I) has the following structure of Formula (VI):

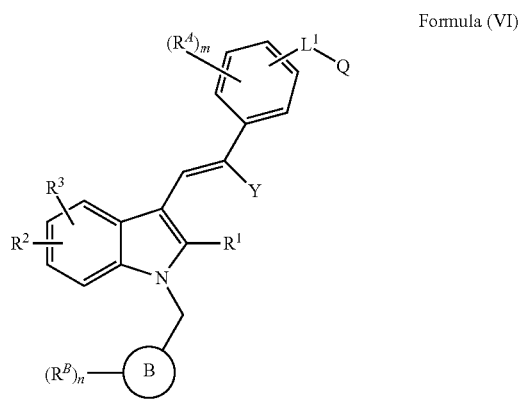

Formula (VI)

or is a pharmaceutically acceptable salt, or solvate thereof.

8. The compound of claim 7, or a pharmaceutically acceptable salt, or solvate thereof, wherein:
$L^1$ is absent, —CH$_2$—, —CH$_2$CH$_2$—, or —CH$_2$CH$_2$CH$_2$—;
Q is —CO$_2$H, or —CO$_2$(C$_1$-C$_6$alkyl);
$R^2$ is halogen, —CN, —OH, C$_1$-C$_4$alkyl, C$_1$-C$_4$fluoroalkyl, C$_1$-C$_4$deuteroalkyl, C$_1$-C$_4$alkoxy, C$_1$-C$_4$fluoroalkoxy, or C$_1$-C$_4$hydroxyalkyl;
$R^3$ is H, halogen, —CN, —OH, C$_1$-C$_4$alkyl, C$_1$-C$_4$fluoroalkyl, C$_1$-C$_4$deuteroalkyl, C$_1$-C$_4$alkoxy, C$_1$-C$_4$fluoroalkoxy, or C$_1$-C$_4$hydroxyalkyl.

9. The compound of claim 8, or a pharmaceutically acceptable salt, or solvate thereof, wherein:
$R^2$ is F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH;
$R^3$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH.

10. The compound of claim 9, or a pharmaceutically acceptable salt, or solvate thereof, wherein:
$R^2$ is Cl;
$R^3$ is H, F, or Cl.

11. The compound of claim 1, or a pharmaceutically acceptable salt, or solvate thereof, wherein the compound has one of the following structures:
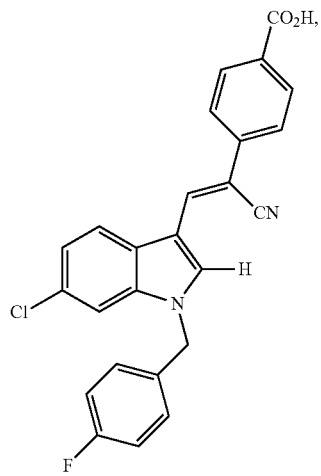
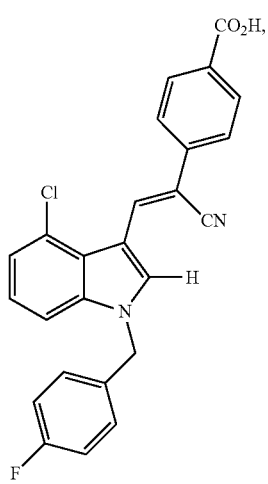
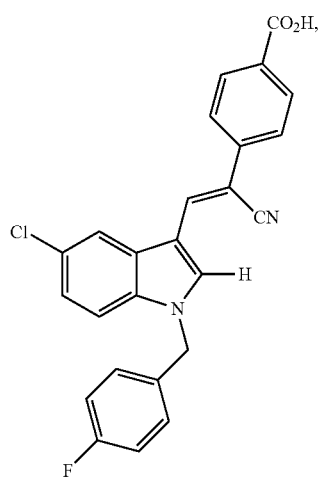
-continued
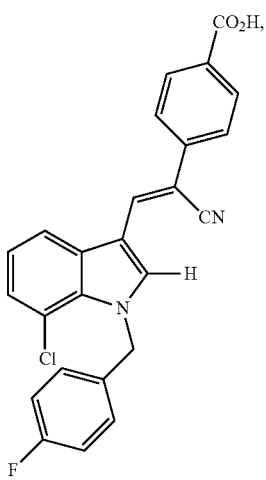
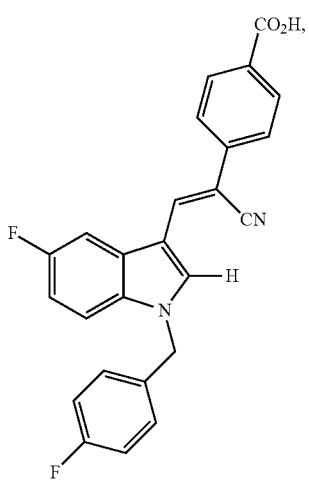
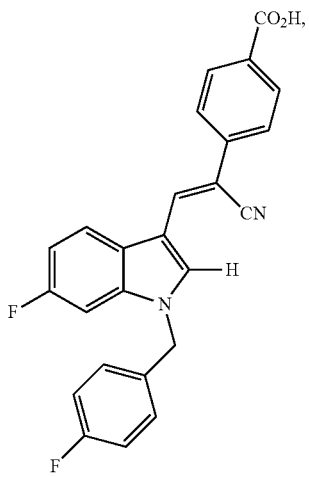

141
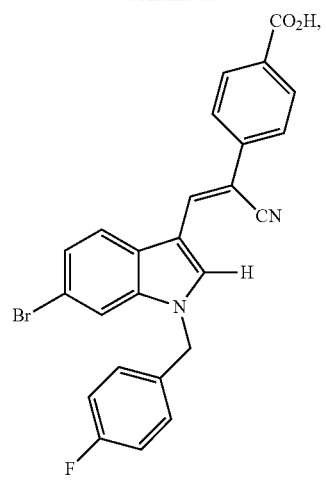
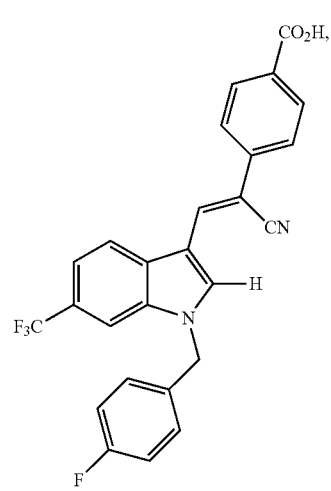
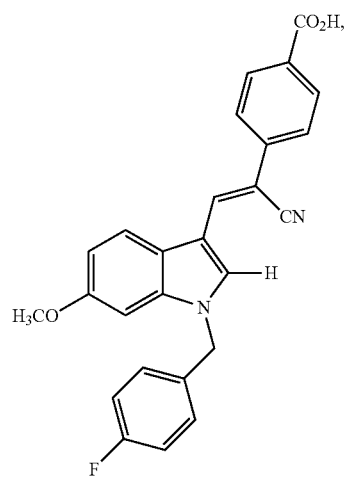
142
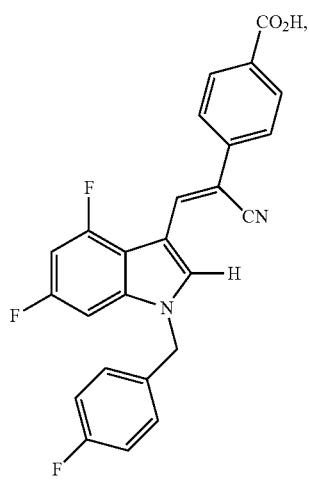
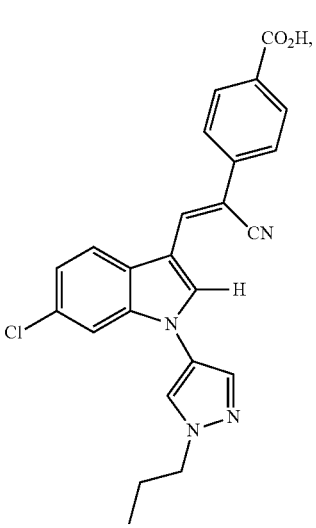
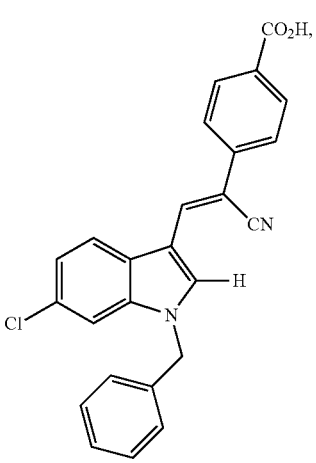

143
-continued
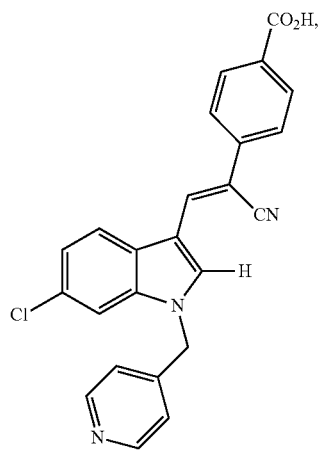
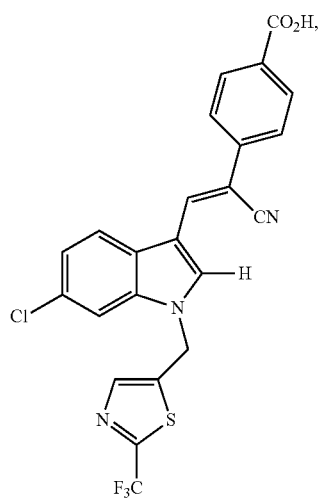
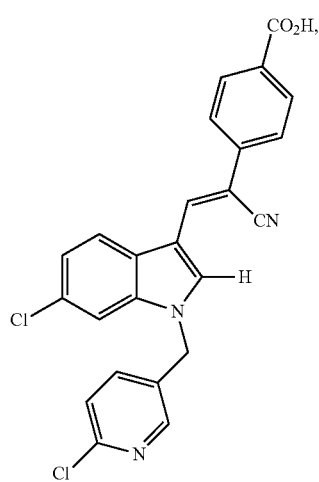
144
-continued
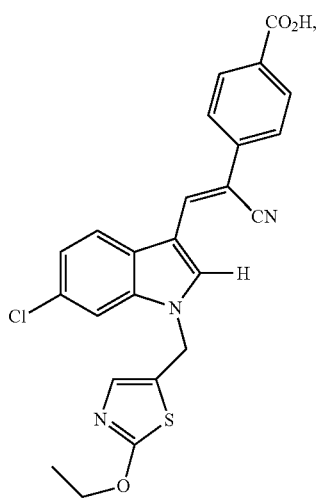
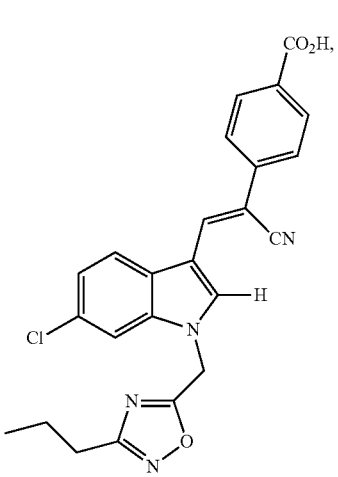
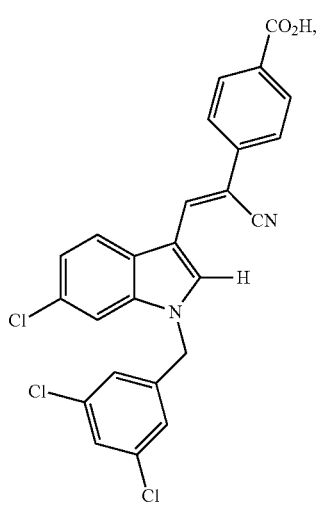

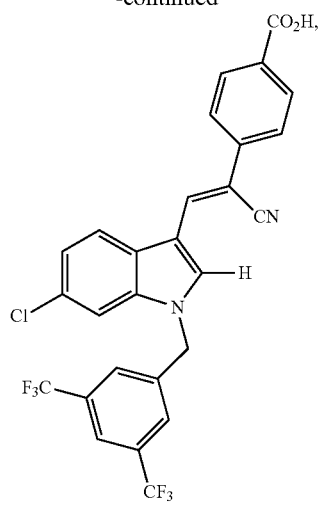
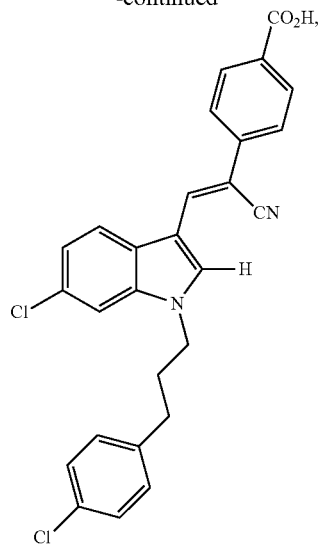

147
-continued
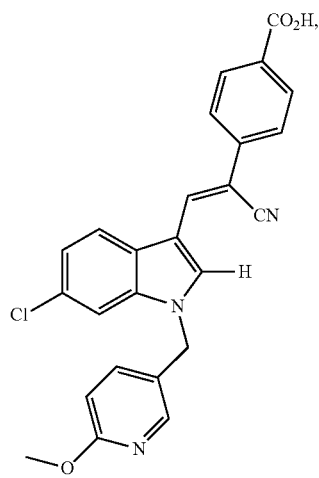
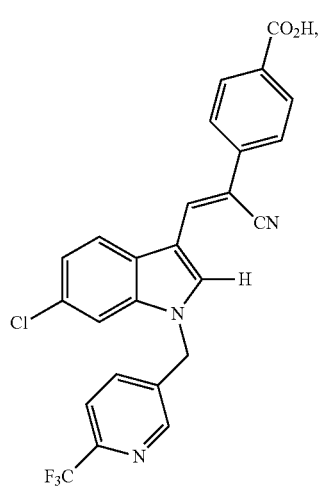
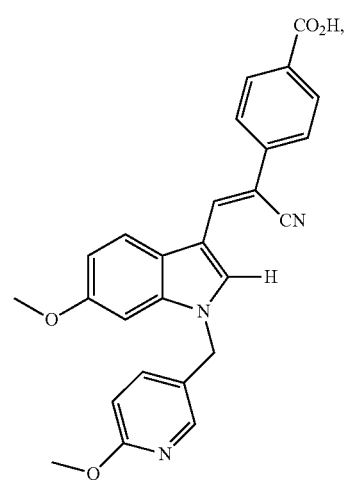
148
-continued
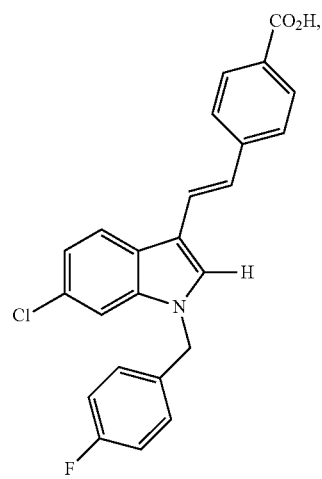
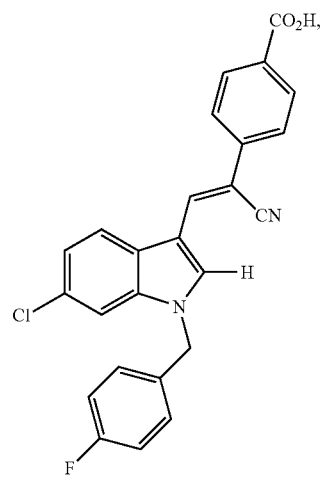
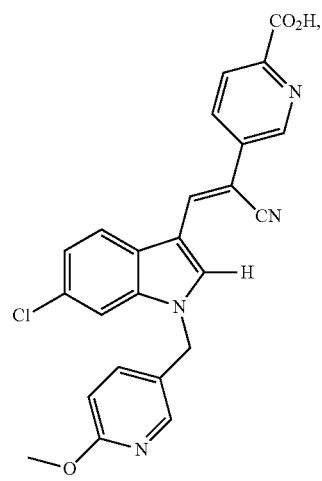

149
-continued
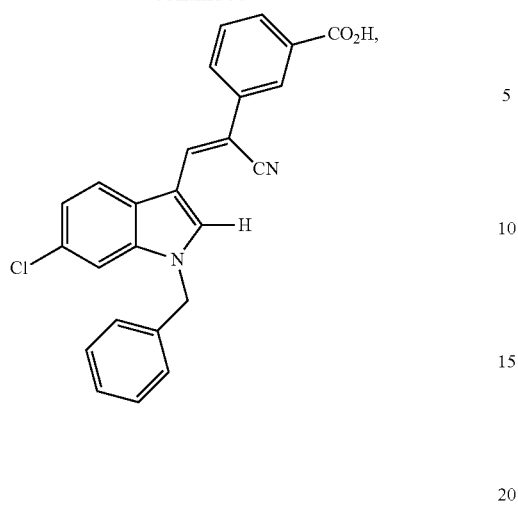
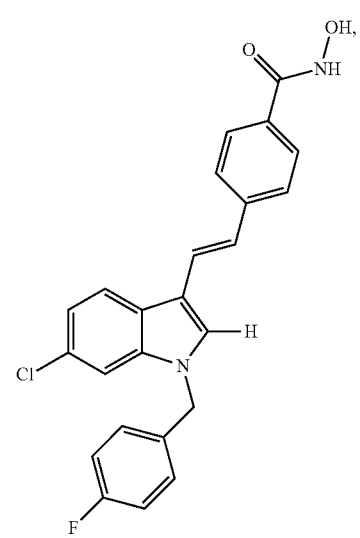
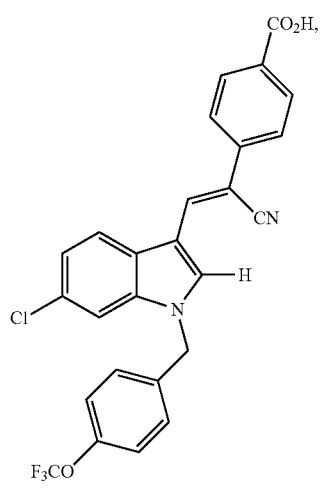
150
-continued
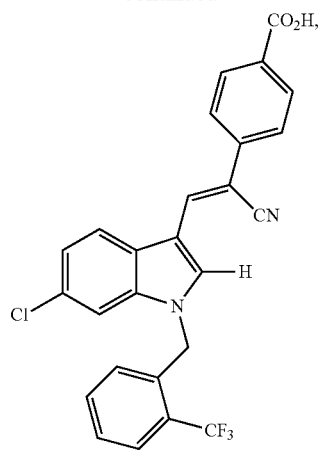
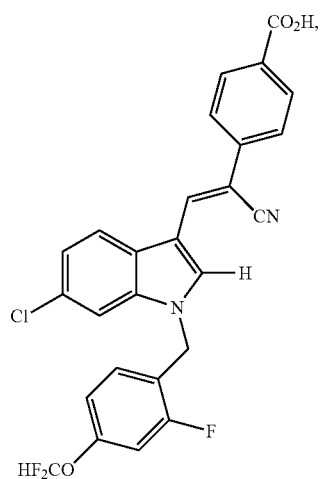
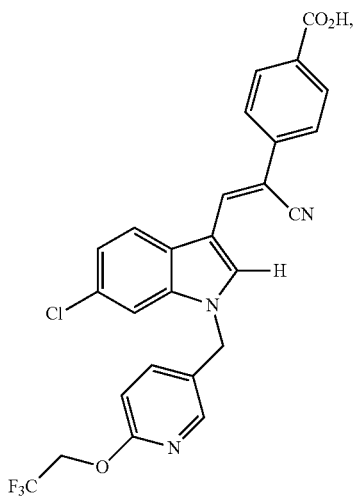

-continued

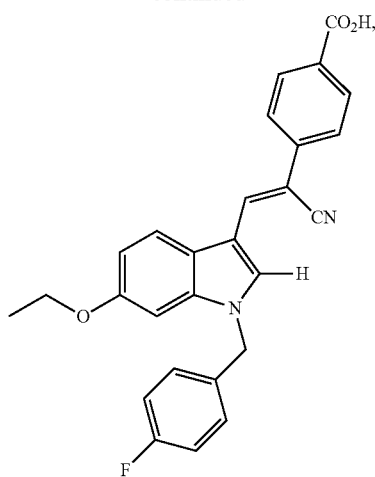

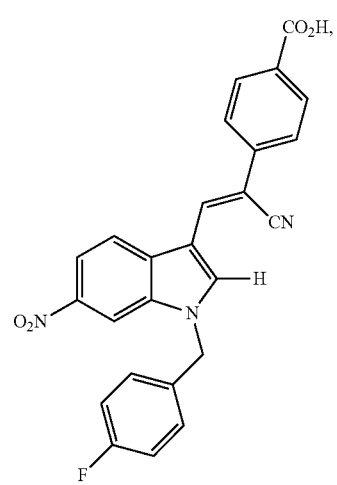

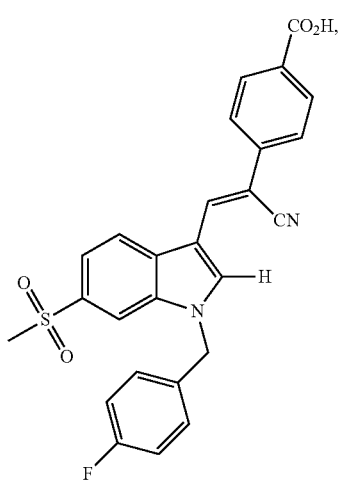

-continued

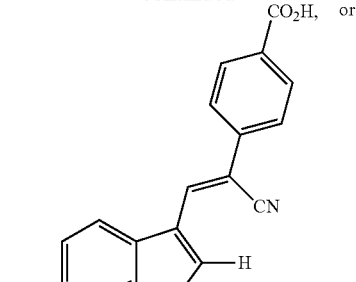

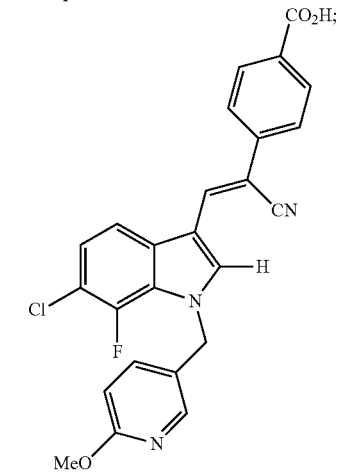

or a pharmaceutically acceptable salt, or solvate thereof.

12. A pharmaceutical composition comprising a compound of Formula (I), or a pharmaceutically acceptable salt, or solvate thereof, and at least one pharmaceutically acceptable excipient:

Formula (I)

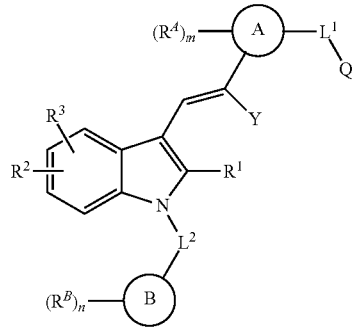

wherein,
$R^1$ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl;
$R^2$ is H, halogen, —CN, —OH, —$OR^9$, —$NO_2$, —$NH_2$, —$N(R^{10})_2$, —OC(=O)$N(R^{10})_2$, —C(=O)$N(R^{10})_2$, —NHC(=O)$R^9$, —NHC(=O)$OR^9$, substituted or unsubstituted $C_1$-$C_4$alkyl, $C_1$-$C_4$fluoroalkyl, $C_1$-$C_4$deuteroalkyl, substituted or unsubstituted $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, $C_1$-$C_4$hydroxyalkyl or substituted or unsubstituted phenyl, or monocyclic heteroaryl;

$R^3$ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)$_2$—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each $R^A$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;

m is 0, 1, or 2;

$L^1$ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$;

X is O, S, S(=O), S(=O)$_2$, C(=O)NH, NHC(=O), NH, OC(=O)NH, NHC(=O)O, or NHC(=O)O;

p is 0 or 1;

q is 0 or 1;

Q is —CO$_2$H, —CO$_2$($C_1$-$C_6$alkyl), —OH, —CN, —B(OH)$_2$, —C(=O)NHSO$_2$R$^9$, —C(=O)N(R$^{10}$)$_2$, —SO$_2$NHC(=O)R$^9$, —CN, tetrazolyl, —OP(=O)(OH)$_2$, —P(=O)(OH)$_2$ or carboxylic acid bioisostere;

$L^2$ is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$-$C_6$alkylene-C(=O)NH—, —$C_1$-$C_6$alkylene-NHC(=O)—, —$C_1$-$C_6$alkylene-C(=O)O—, —$C_1$-$C_6$alkylene-OC(=O)—, —$C_1$-$C_6$alkylene-OC(=O)NH—, —$C_1$-$C_6$alkylene-NHC(=O)NH—, or absent;

Y is H, $C_1$-$C_6$alkyl, halogen, or CN;

Ring B is a monocyclic aryl, bicyclic aryl, monocyclic heteroaryl or bicyclic heteroaryl;

each $R^B$ is independently selected from the group consisting of H, halogen, —CN, —NO$_2$, —OH, —OR$^9$, —SR$^9$, —S(=O)R$^9$, —S(=O)$_2$R$^9$, —S(=O)$_2$N(R$^{10}$)$_2$, —NR$^{10}$S(=O)$_2$R$^9$, —C(=O)R$^9$, —OC(=O)R$^9$, —CO$_2$R$^{10}$, —OCO$_2$R$^9$, —N(R$^{10}$)$_2$, —C(=O)N(R$^{10}$)$_2$, —OC(=O)N(R$^{10}$)$_2$, —NHC(=O)R$^9$, —NHC(=O)OR$^9$, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, substituted or unsubstituted monocyclic heteroaryl, and a substituted or unsubstituted bicyclic heteroaryl;

n is 0, 1, or 2;

each $R^9$ is independently selected from the group consisting of $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, —$C_1$-$C_4$alkylene-(substituted or unsubstituted monocyclic heteroaryl), a substituted or unsubstituted bicyclic heteroaryl and —$C_1$-$C_4$alkylene-(substituted or unsubstituted bicyclic heteroaryl);

each $R^{10}$ is independently selected from the group consisting of H, $C_1$-$C_6$alkyl, $C_1$-$C_6$fluoroalkyl, $C_1$-$C_6$deuteroalkyl, $C_3$-$C_6$cycloalkyl, a substituted or unsubstituted phenyl, —$C_1$-$C_4$alkylene-(substituted or unsubstituted phenyl), a substituted or unsubstituted monocyclic heteroaryl, and —$C_1$-$C_4$alkylene-(substituted or unsubstituted monocyclic heteroaryl); or two $R^{10}$ groups attached to the same N atom are taken together with the N atom to which they are attached to form a substituted or unsubstituted heterocycle.

13. The pharmaceutical composition of claim 12, wherein the pharmaceutical composition is formulated for administration to a mammal by intravenous administration, subcutaneous administration, oral administration, inhalation, nasal administration, dermal administration, or ophthalmic administration.

14. The pharmaceutical composition of claim 12, wherein the pharmaceutical composition is in the form of a tablet, a pill, a capsule, a liquid, a suspension, a gel, a dispersion, a solution, an emulsion, an ointment, or a lotion.

15. The pharmaceutical composition of claim 12, wherein:

$R^1$ is H, F, Cl, —CN, —C(=O)H, —CH$_3$, —CF$_3$, or —CD$_3$;

$R^2$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH;

Ring A is phenyl, monocyclic heteroaryl containing 1-4 N atoms and 0 or 1 O or S atoms, or monocyclic heteroaryl containing 0-4 N atoms and 1 O or S atoms;

$L^1$ is absent, —CH$_2$—, —CH$_2$CH$_2$—, —CH$_2$CH$_2$CH$_2$—, —CH(CH$_3$)—, —CH(CH$_2$CH$_3$)—, —C(CH$_3$)$_2$—, —C(CH$_2$CH$_3$)$_2$—, cyclopropyl-1,1-diyl, cyclobutyl-1,1-diyl, cyclopentyl-1,1-diyl or cyclohexyl-1,1-diyl;

Q is —CO$_2$H, —CO$_2$($C_1$-$C_6$alkyl), —C(=O)NHSO$_2$R$^9$ or tetrazolyl;

$L^2$ is —$C_1$-$C_6$alkylene-;

Y is H, —CH$_3$, F, Cl, Br, or CN;

Ring B is phenyl, monocyclic heteroaryl containing 1-4 N atoms and 0 or 1 O or S atoms, or monocyclic heteroaryl containing 0-4 N atoms and 1 O or S atoms.

16. The pharmaceutical composition of claim 15, wherein the compound has the following structure of Formula (VII):

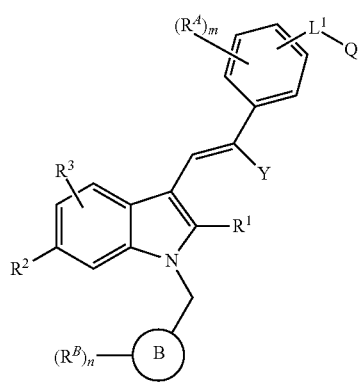

Formula (VII)

wherein, each $R^A$ is independently selected from the group consisting of H, halogen, —CN, —OH, —OR$^9$, $C_1$-$C_6$alkyl, and $C_1$-$C_6$fluoroalkyl;

Ring B is phenyl, thiazolyl, pyridinyl, pyrimidinyl, pyrazinyl, or pyridazinyl;

$R^3$ is H, F, Cl, Br, I, —CN, —OH, —CH$_3$, —CF$_3$, —CD$_3$, —OCH$_3$, —OCH$_2$CH$_3$, —OCF$_3$, —OCH$_2$CF$_3$, or —CH$_2$OH;

$L^1$ is absent, —CH$_2$—, —CH$_2$CH$_2$—, or —CH$_2$CH$_2$CH$_2$—;

Q is —CO$_2$H, or —CO$_2$(C$_1$-C$_6$alkyl);

or is a pharmaceutically acceptable salt, or solvate thereof.

17. The pharmaceutical composition of claim 12 wherein the compound has one of the following structures:

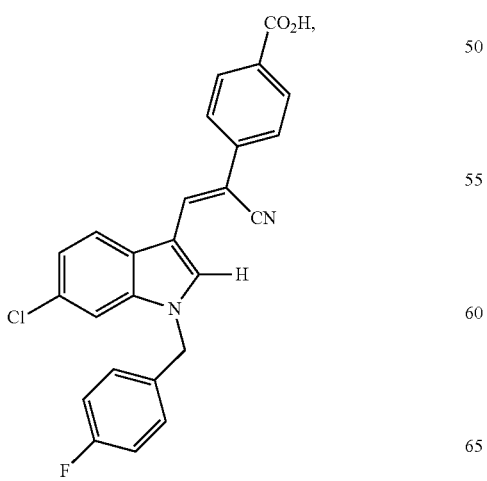

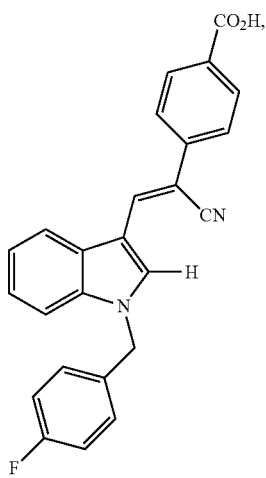

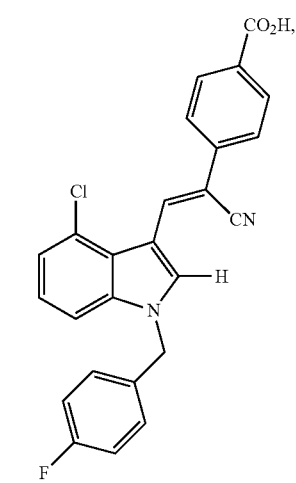

157
-continued
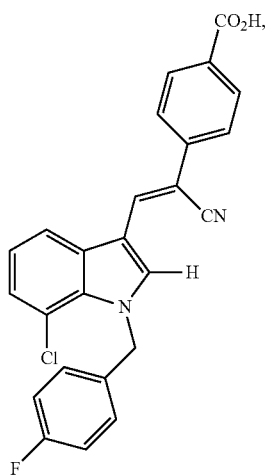
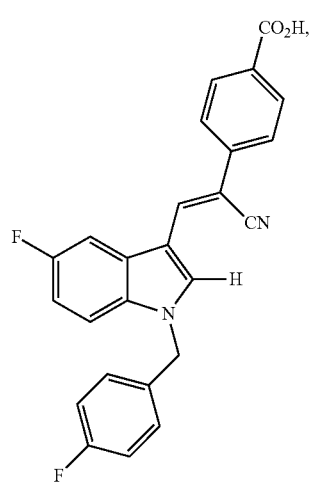
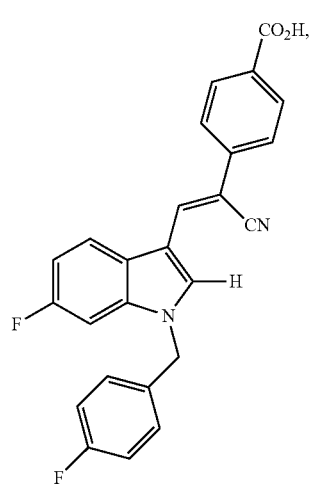
158
-continued
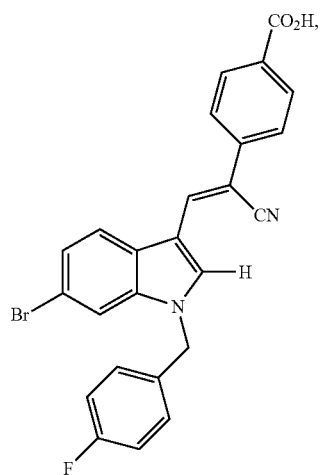
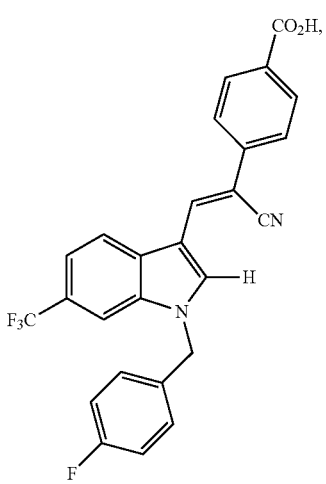
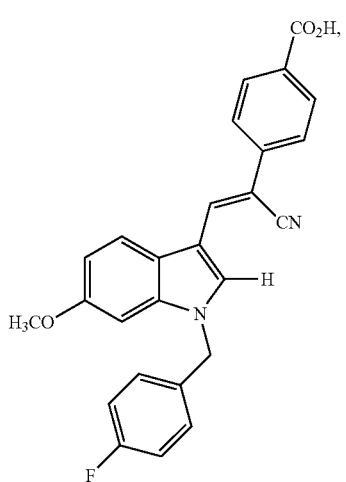

159
-continued
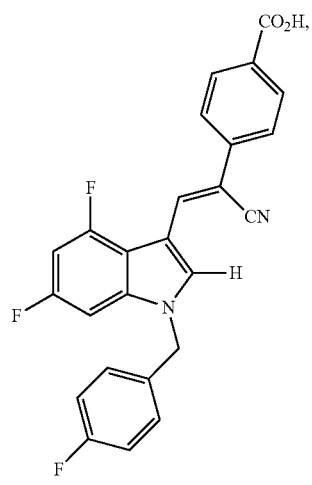
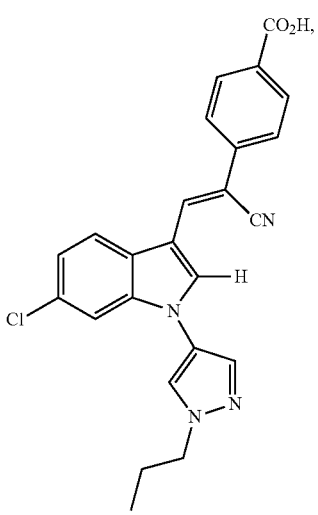
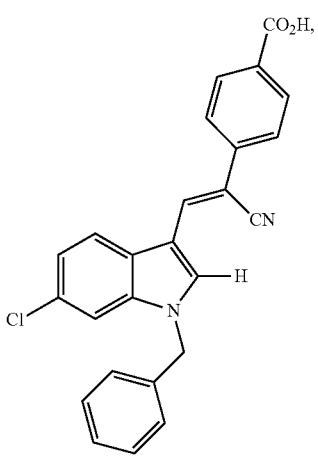
160
-continued
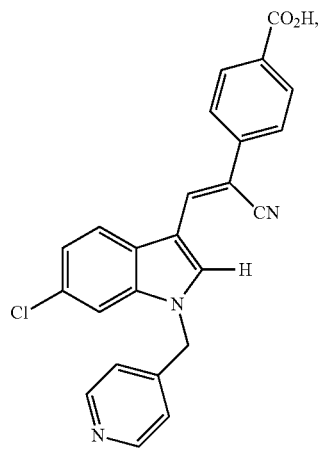 [SMILES: N#C/C(=C\c1cn(Cc2ccncc2)c2cc(Cl)ccc12)c1ccc(C(=O)O)cc1]
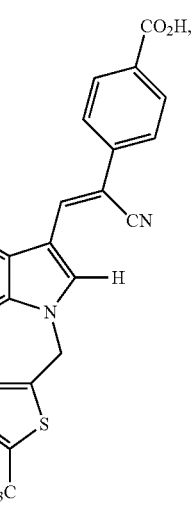
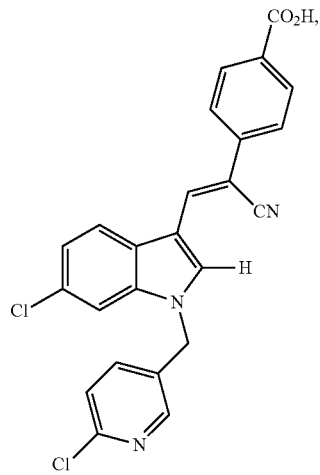

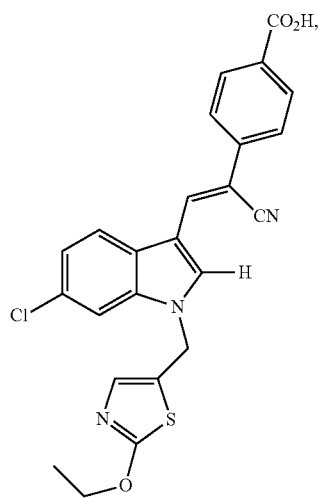
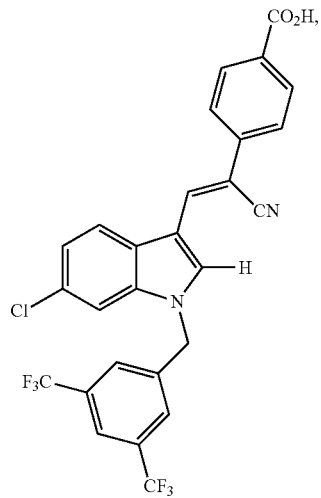
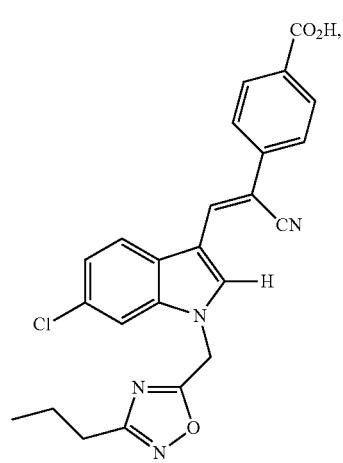
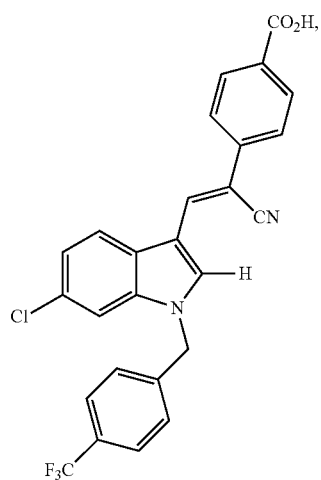
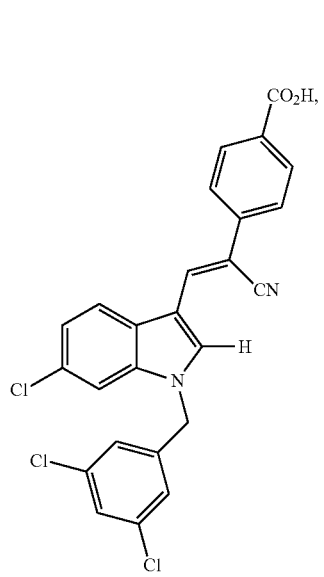
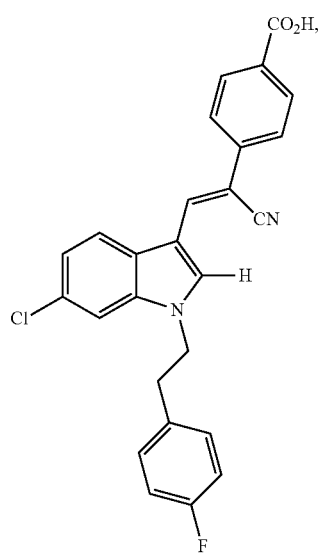

163
-continued
164
-continued
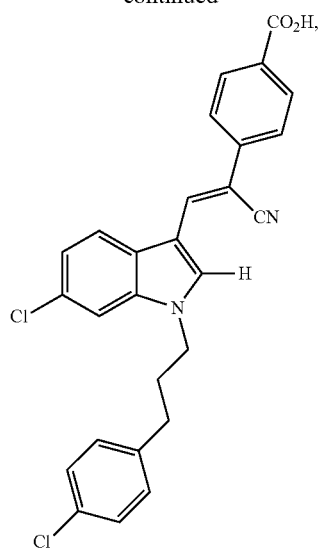
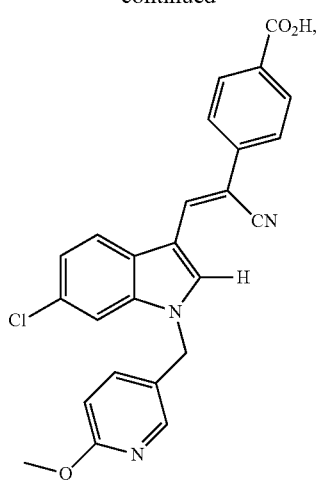
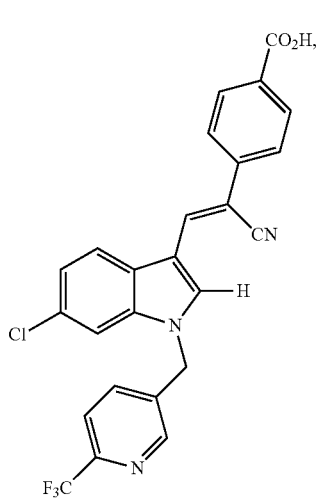

-continued
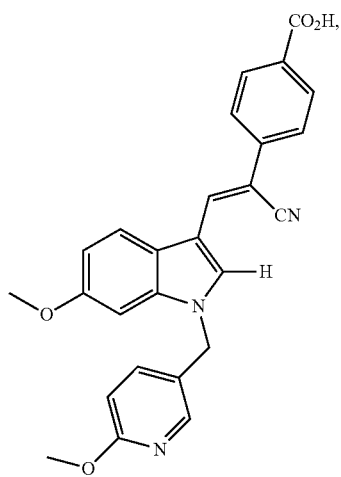
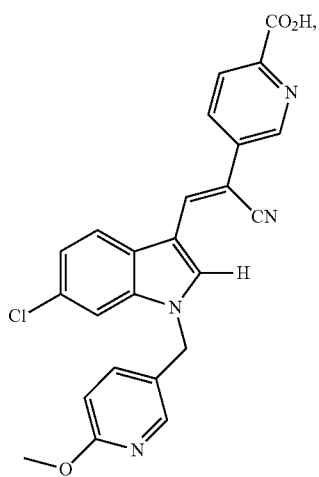
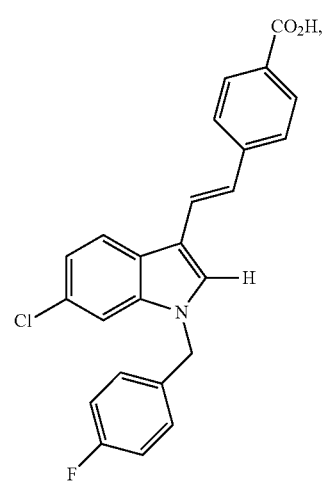
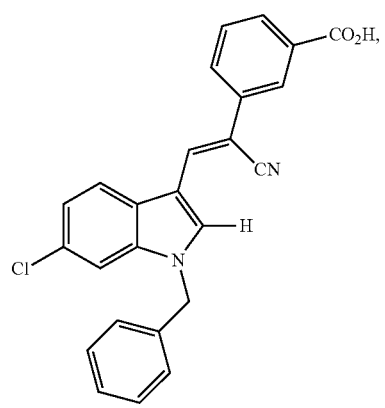
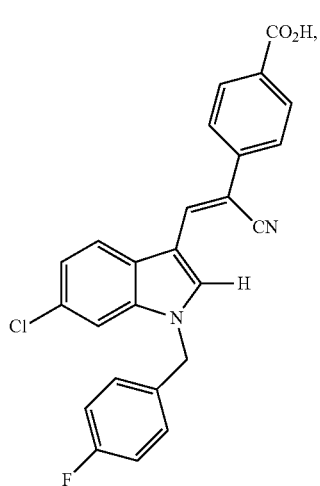
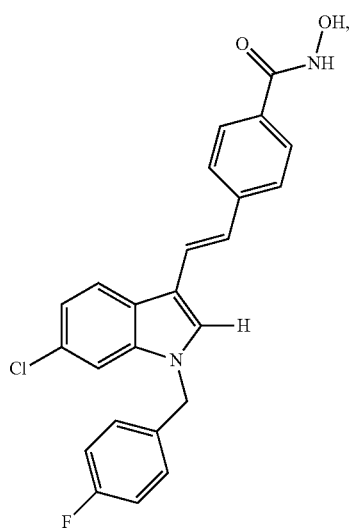

167
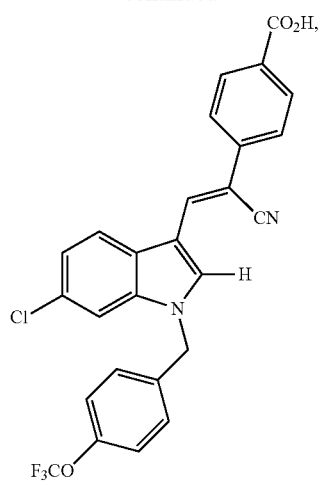
168
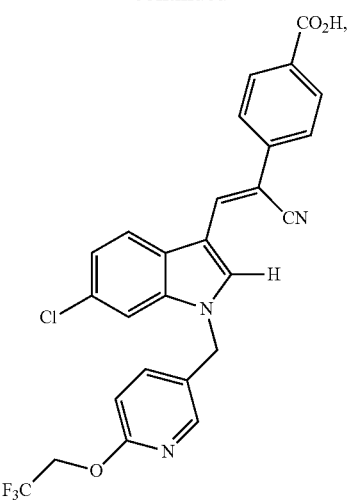
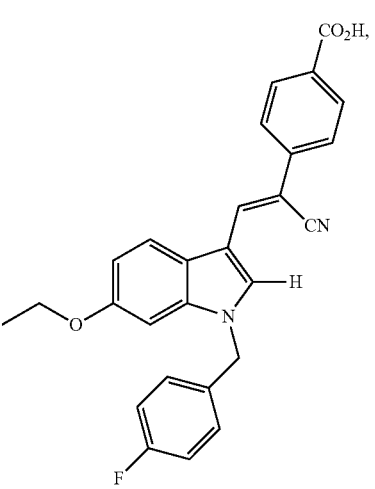
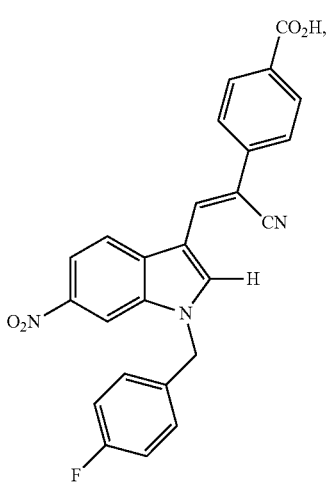

-continued

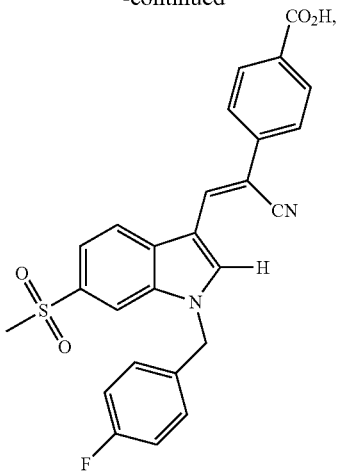

or

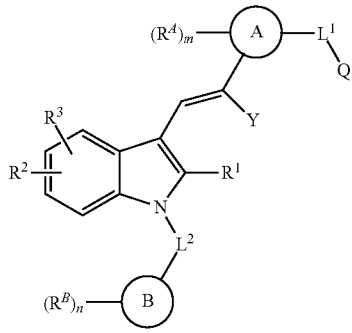

Formula (I)

wherein,
R¹ is H, D, halogen, —CN, —C(=O)H, $C_1$-$C_4$alkyl, $C_3$-$C_6$cycloalkyl, $C_1$-$C_4$fluoroalkyl, or $C_1$-$C_4$deuteroalkyl;

R² is H, halogen, —CN, —OH, —OR⁹, —NO₂, —NH₂, —N(R¹⁰)₂, —OC(=O)N(R¹⁰)₂, —C(=O)N(R¹⁰)₂, —NHC(=O)R⁹, —NHC(=O)OR⁹, substituted or unsubstituted $C_1$-$C_4$alkyl, $C_1$-$C_4$fluoroalkyl, $C_1$-$C_4$deuteroalkyl, substituted or unsubstituted $C_1$-$C_4$alkoxy, $C_1$-$C_4$fluoroalkoxy, —S—$C_1$-$C_4$alkyl, —S(=O)—$C_1$-$C_4$alkyl, —S(=O)₂—$C_1$-$C_4$alkyl, $C_1$-$C_4$hydroxyalkyl or substituted or unsubstituted phenyl, or monocyclic heteroaryl;

R³ is H, halogen, —CN, —OH, $C_1$-$C_4$alkyl, $C_1$-$C_4$fluoroalkyl, $C_1$-$C_4$deuteroalkyl, $C_1$-$C_4$alkoxy, $C_1$-$C_4$fluoroalkoxy, —S—$C_1$-$C_4$alkyl, —S(=O)—$C_1$-$C_4$alkyl, —S(=O)₂—$C_1$-$C_4$alkyl, or $C_1$-$C_4$hydroxyalkyl;

Ring A is a monocyclic aryl, bicyclic aryl, monocyclic heteroaryl or bicyclic heteroaryl;

each R$^A$ is independently selected from the group consisting of H, halogen, —CN, —NO₂, —OH, —OR⁹, —SR⁹, —S(=O)R⁹, —S(=O)₂R⁹, —S(=O)₂N(R¹⁰)₂, —NR¹⁰S(=O)₂R⁹, —C(=O)R⁹, —OC(=O)R⁹, —CO₂R¹⁰, —OCO₂R⁹, —N(R¹⁰)₂, —C(=O)N(R¹⁰)₂, —OC(=O)N(R¹⁰)₂, —NHC(=O)R⁹, —NHC(=O)OR⁹, substituted or unsubstituted $C_1$-$C_6$alkyl, $C_1$-$C_6$fluoroalkyl, $C_1$-$C_6$deuteroalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted phenyl, and substituted or unsubstituted monocyclic heteroaryl;

m is 0, 1, or 2;

L¹ is absent, $C_1$-$C_6$alkylene, $C_1$-$C_6$fluoroalkylene, $C_3$-$C_6$cycloalkylene, ($C_1$-$C_6$alkylene)$_p$-$C_3$-$C_6$cycloalkylene-($C_1$-$C_6$alkylene)$_q$, or —($C_1$-$C_6$alkylene)$_p$-X—($C_1$-$C_6$alkylene)$_q$;

X is O, S, S(=O), S(=O)₂, C(=O)NH, NHC(=O), NH, OC(=O)NH, NHC(=O)O, or NHC(=O)O;

p is 0 or 1;
q is 0 or 1;

Q is —CO₂H, —CO₂($C_1$-$C_6$alkyl), —OH, —CN, —B(OH)₂, —C(=O)NHSO₂R⁹, —C(=O)N(R¹⁰)₂, —SO₂NHC(=O)R⁹, —CN, tetrazolyl, —OP(=O)(OH)₂, —P(=O)(OH)₂ or carboxylic acid bioisostere;

L² is —$C_1$-$C_6$alkylene-, —C(=O)—, —C(=O)—$C_1$-$C_6$alkylene-, —C(=O)NH—, —C(=O)NH—$C_1$-$C_6$alkylene-, —C(=O)O—, —C(=O)O—$C_1$-$C_6$alkylene-, —$C_1$-$C_6$alkylene-C(=O)—, —$C_1$- or a pharmaceutically acceptable salt, or solvate thereof.

18. A method of treating a disease or condition in a mammal in which autotaxin activity contributes to the symptomology or progression of the disease or condition comprising administering a compound of Formula (I), or a pharmaceutically acceptable salt, or solvate thereof, to the mammal in need thereof:

C₆alkylene-C(=O)NH—, —C₁-C₆alkylene-NHC(=O)—, —C₁-C₆alkylene-C(=O)O—, —C₁-C₆alkylene-OC(=O)—, —C₁-C₆alkylene-OC(=O)NH—, —C₁-C₆alkylene-NHC(=O)NH—, or absent;

Y is H, C₁-C₆alkyl, halogen, or CN;

Ring B is a monocyclic aryl, bicyclic aryl, monocyclic heteroaryl or bicyclic heteroaryl;

each R$^B$ is independently selected from the group consisting of H, halogen, —CN, —NO₂, —OH, —OR⁹, —SR⁹, —S(=O)R⁹, —S(=O)₂R⁹, —S(=O)₂N(R¹⁰)₂, —NR¹⁰S(=O)₂R⁹, —C(=O)R⁹, —OC(=O)R⁹, —CO₂R¹⁰, —OCO₂R⁹, —N(R¹⁰)₂, —C(=O)N(R¹⁰)₂, —OC(=O)N(R¹⁰)₂, —NHC(=O)R⁹, —NHC(=O)OR⁹, substituted or unsubstituted C₁-C₆alkyl, C₁-C₆fluoroalkyl, C₁-C₆deuteroalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted phenyl, substituted or unsubstituted monocyclic heteroaryl, and a substituted or unsubstituted bicyclic heteroaryl;

n is 0, 1, or 2;

each R⁹ is independently selected from the group consisting of C₁-C₆alkyl, C₁-C₆fluoroalkyl, C₁-C₆deuteroalkyl, C₃-C₆cycloalkyl, a substituted or unsubstituted phenyl, —C₁-C₄alkylene-(substituted or unsubstituted phenyl), a substituted or unsubstituted monocyclic heteroaryl, —C₁-C₄alkylene-(substituted or unsubstituted monocyclic heteroaryl), a substituted or unsubstituted bicyclic heteroaryl and —C₁-C₄alkylene-(substituted or unsubstituted bicyclic heteroaryl);

each R¹⁰ is independently selected from the group consisting of H, C₁-C₆alkyl, C₁-C₆fluoroalkyl, C₁-C₆deuteroalkyl, C₃-C₆cycloalkyl, a substituted or unsubstituted phenyl, —C₁-C₄alkylene-(substituted or unsubstituted phenyl), a substituted or unsubstituted monocyclic heteroaryl, and —C₁-C₄alkylene-(substituted or unsubstituted monocyclic heteroaryl); or two R¹⁰ groups attached to the same N atom are taken together with the N atom to which they are attached to form a substituted or unsubstituted heterocycle.

19. The method of claim 18, wherein the disease or condition is cancer, fibrosis, pruritus, an inflammatory disease or condition, an airway disease or condition, an autoimmune disease or condition, obesity, intraocular pressure, neuropathic pain, or combinations thereof.

20. The method of claim 18, wherein:

R¹ is H, F, Cl, —CN, —C(=O)H, —CH₃, —CF₃, or —CD₃;

R² is F, Cl, Br, I, —CN, —OH, —CH₃, —CF₃, —CD₃, —OCH₃, —OCH₂CH₃, —OCF₃, —OCH₂CF₃, or —CH₂OH;

Ring A is phenyl, naphthyl, monocyclic heteroaryl containing 1-4 N atoms and 0 or 1 O or S atoms, or monocyclic heteroaryl containing 0-4 N atoms and 1 O or S atoms;

L² is —C₁-C₆alkylene-;

Y is H, —CH₃, F, Cl, Br, or CN;

L¹ is absent, —CH₂—, —CH₂CH₂—, —CH₂CH₂CH₂—, —CH(CH₃)—, —CH(CH₂CH₃)—, —C(CH₃)₂—, —C(CH₂CH₃)₂—, cyclopropyl-1,1-diyl, cyclobutyl-1,1-diyl, cyclopentyl-1,1-diyl or cyclohexyl-1,1-diyl;

Q is —CO₂H, —CO₂(C₁-C₆alkyl), —C(=O)NHSO₂R⁹ or tetrazolyl;

Ring B is phenyl, naphthyl, monocyclic heteroaryl containing 1-4 N atoms and 0 or 1 O or S atoms, or monocyclic heteroaryl containing 0-4 N atoms and 1 O or S atoms.

21. The method of claim 20, wherein the compound has the following structure of Formula (VII):

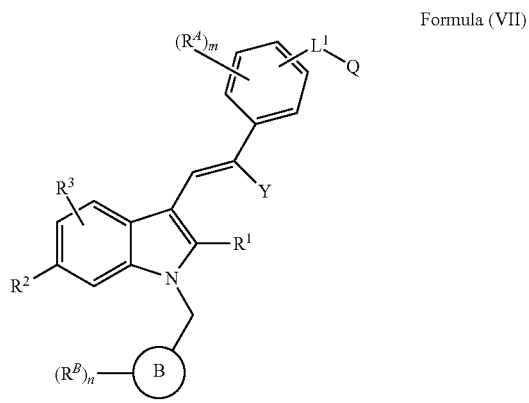

Formula (VII)

wherein, each R$^A$ is independently selected from the group consisting of H, halogen, —CN, —OH, —OR⁹, C₁-C₆alkyl, and C₁-C₆fluoroalkyl;

Ring B is phenyl, thiazolyl, pyridinyl, pyrimidinyl, pyrazinyl, or pyridazinyl;

R³ is H, F, Cl, Br, I, —CN, —OH, —CH₃, —CF₃, —CD₃, —OCH₃, —OCH₂CH₃, —OCF₃, —OCH₂CF₃, or —CH₂OH;

L¹ is absent, —CH₂—, —CH₂CH₂—, or —CH₂CH₂CH₂—;

Q is —CO₂H, or —CO₂(C₁-C₆alkyl);

or is a pharmaceutically acceptable salt or solvate thereof.

22. The method of claim 18, wherein the compound of Formula (I) has one of the following structures:

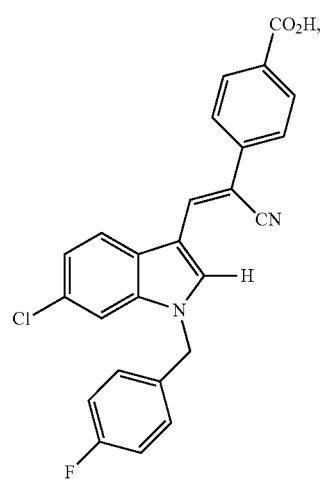

173
-continued
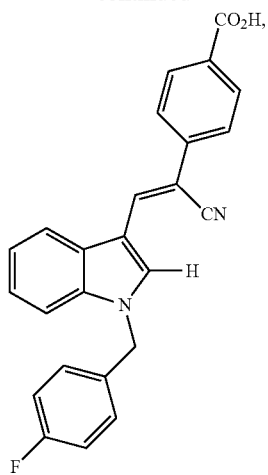
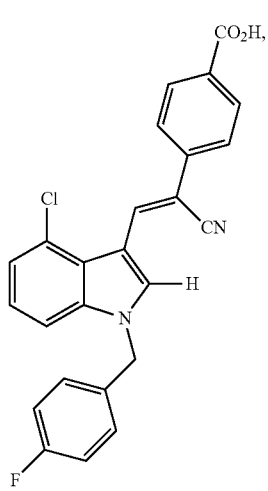
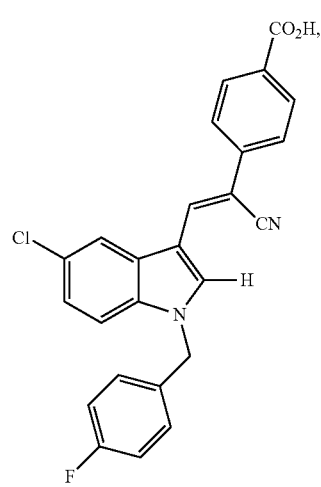
174
-continued
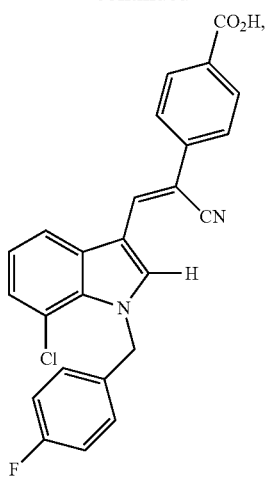
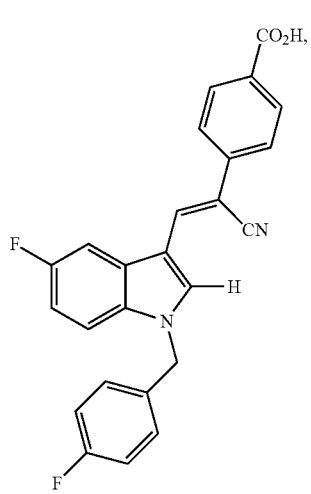
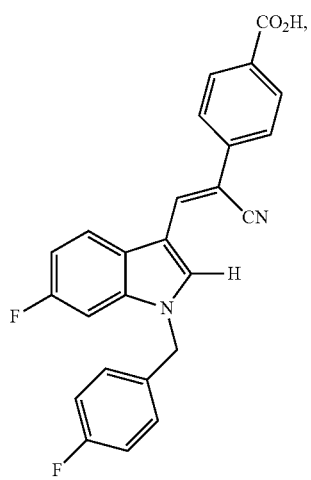

175
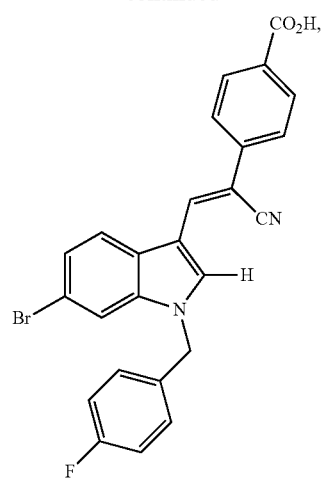
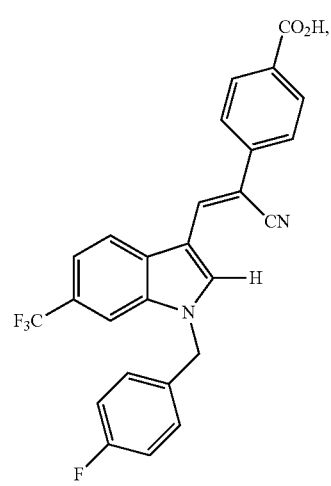
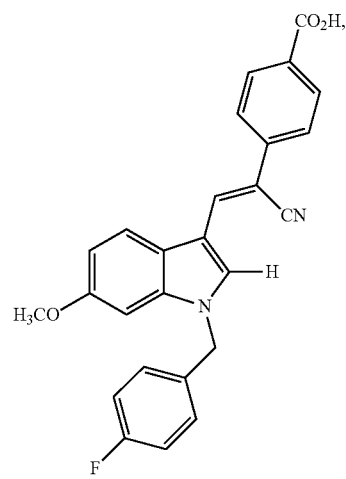
176
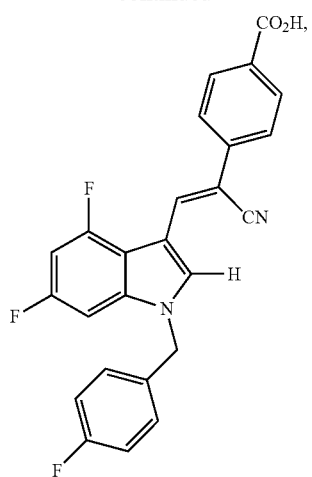
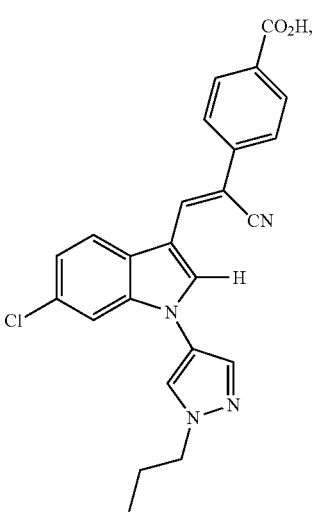
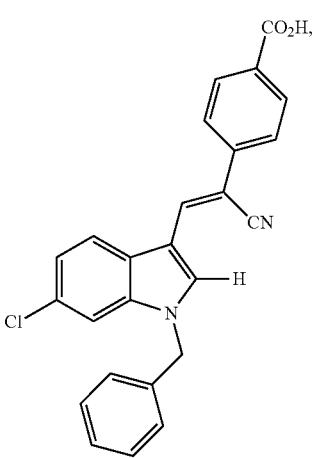 [SMILES: N#C/C(=C\c1cn(Cc2ccncc2)c2cc(Cl)ccc12)c1ccc(C(=O)O)cc1]

177
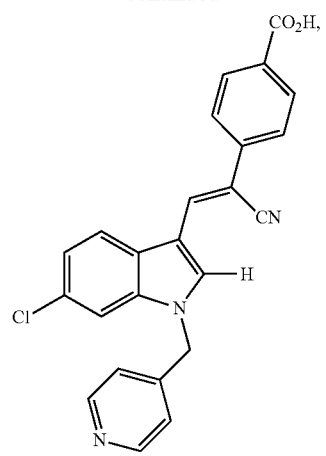
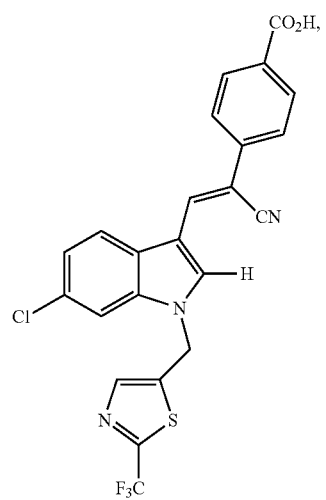
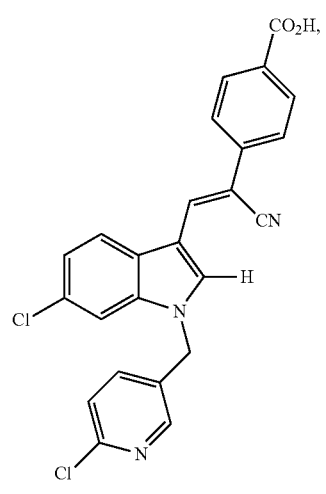
178
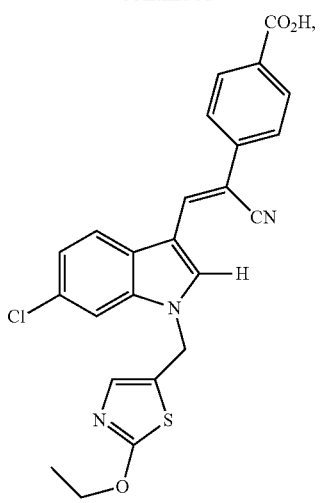
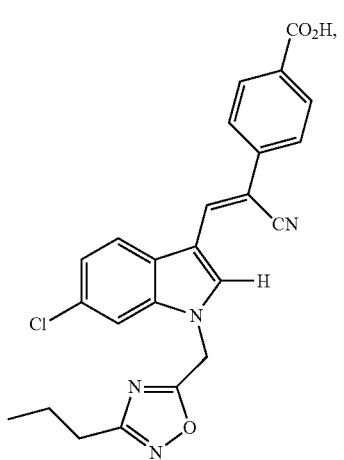

179 -continued
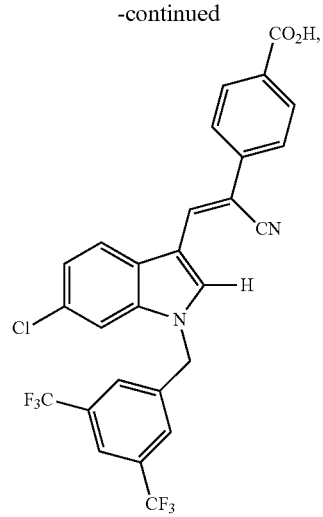
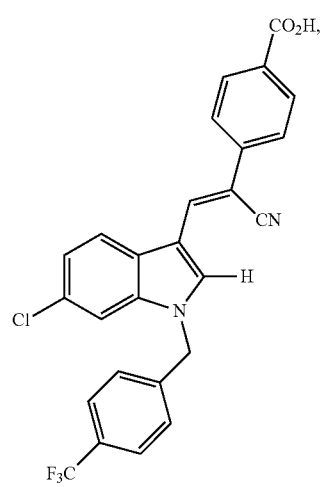
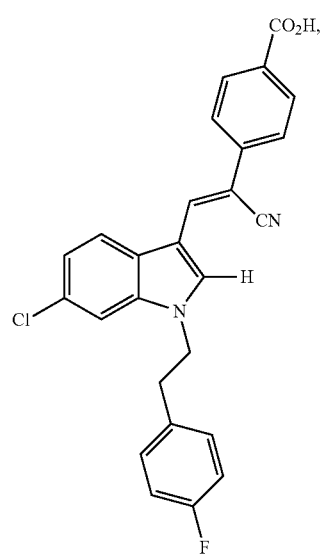
180 -continued
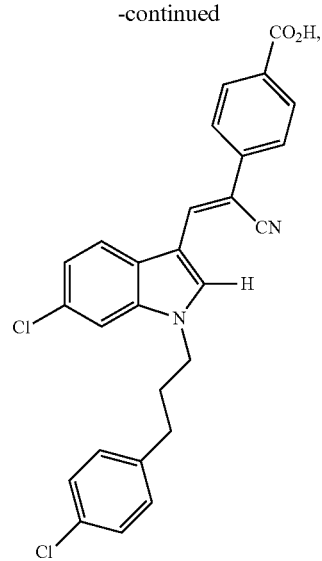
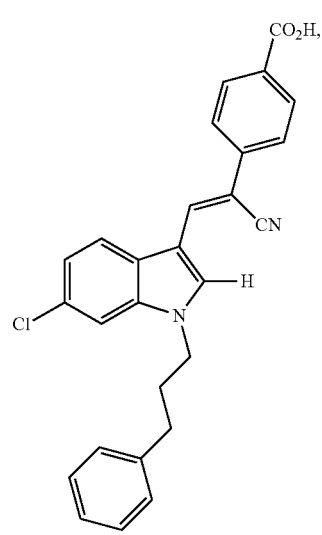
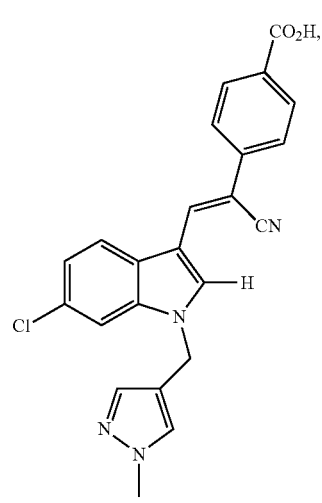

181
-continued
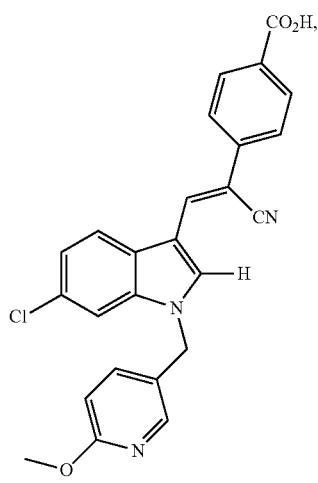
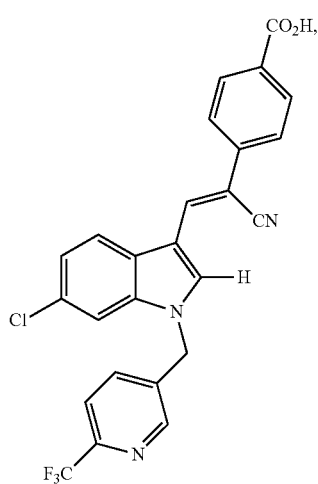
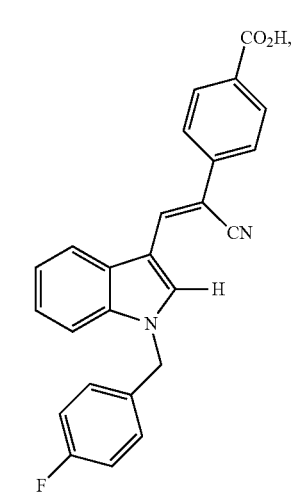
182
-continued
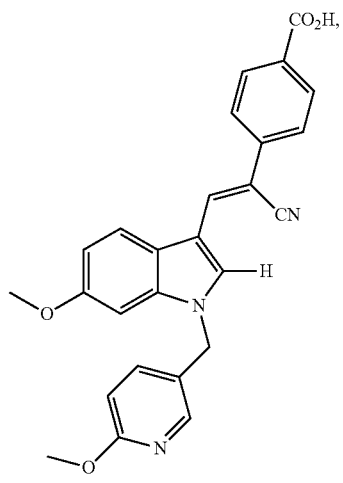
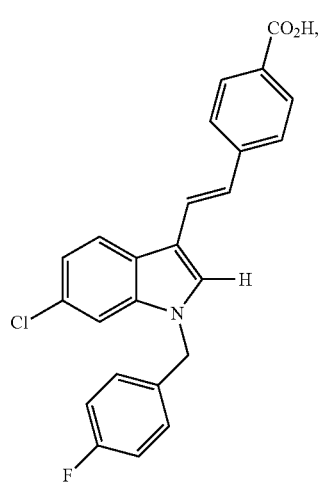
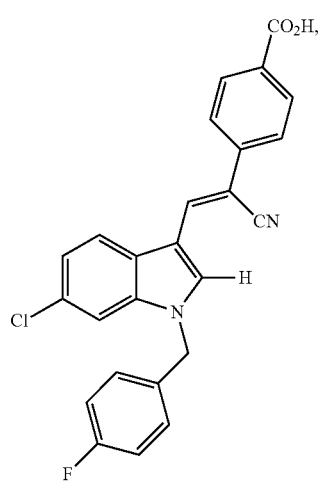

-continued
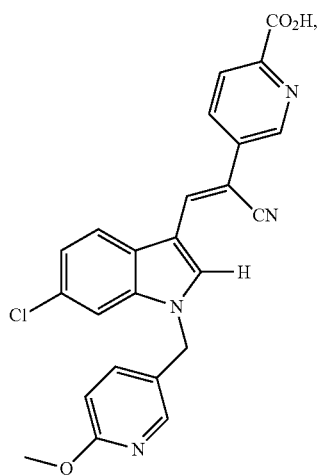
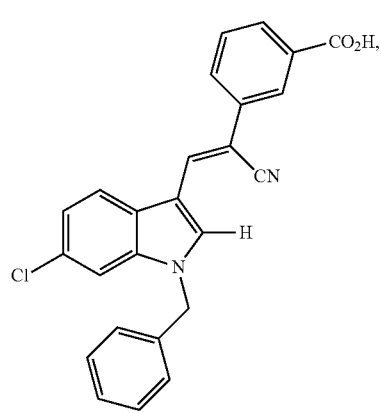
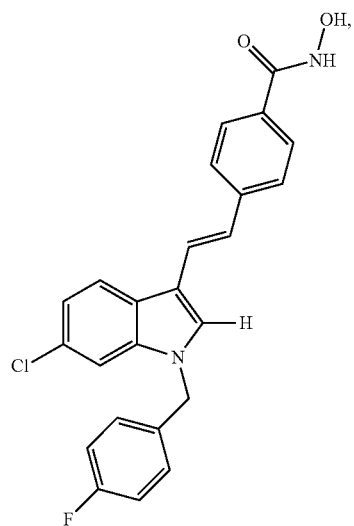
-continued
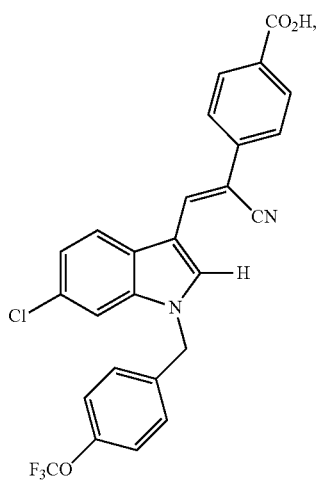
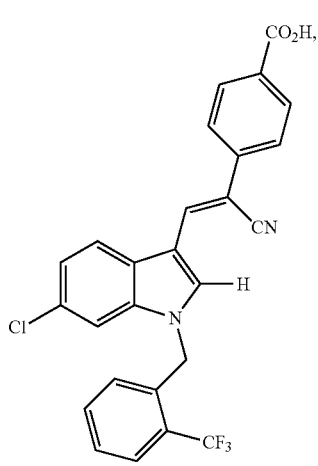
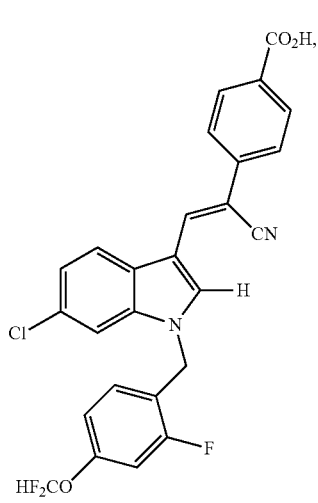

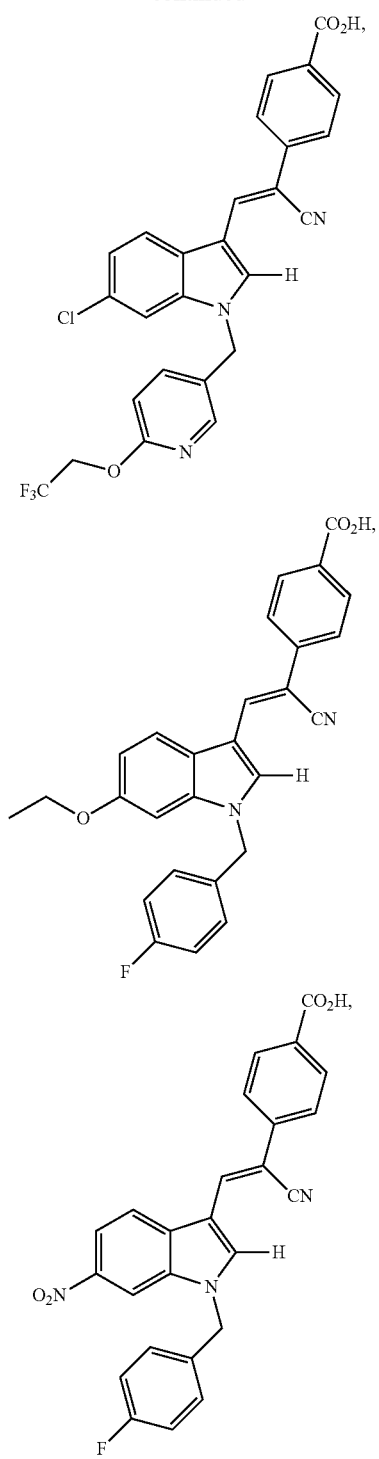
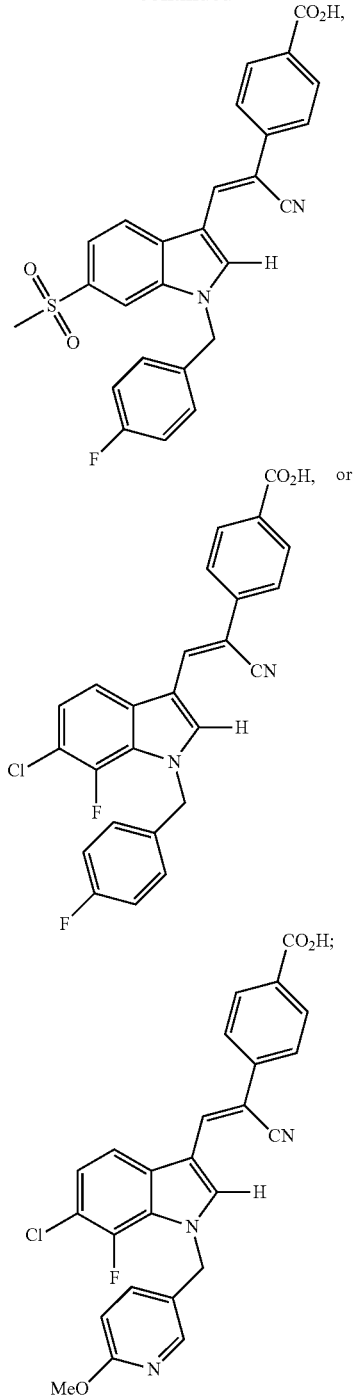
or a pharmaceutically acceptable salt, or solvate thereof.
* * * * *